US011518975B2

(12) United States Patent
Johnson et al.

(10) Patent No.: US 11,518,975 B2
(45) Date of Patent: Dec. 6, 2022

(54) ENGINEERED MICROORGANISMS FOR THE PRODUCTION OF INTERMEDIATES AND FINAL PRODUCTS

(71) Applicants: Alliance for Sustainable Energy, LLC, Golden, CO (US); UT-Battelle, LLC, Oak Ridge, TN (US); TRIAD National Security, LLC, Los Alamos, NM (US)

(72) Inventors: Christopher W. Johnson, Denver, CO (US); Peter Corbin St. John, Westminster, CO (US); Gregg Tyler Beckham, Golden, CO (US); Joshua Ryan Elmore, Richland, WA (US); Adam Michael Guss, Knoxville, TN (US); Davinia Salvachua Rodriguez, Golden, CO (US); Gayle Joann Bentley, Edgewater, CO (US); George Lee Peabody, V, Oak Ridge, TN (US); Taraka Dale, Los Alamos, NM (US); Ramesh K. Jha, Los Alamos, NM (US); Niju Narayanan, Los Alamos, NM (US)

(73) Assignees: Alliance for Sustainable Energy, LLC, Golden, CO (US); UT-Battelle, LLC, Oak Ridge, TN (US); TRIAD National Security, LLC, Los Alamos, NM (US)

( * ) Notice: Subject to any disclaimer, the term of this patent is extended or adjusted under 35 U.S.C. 154(b) by 412 days.

(21) Appl. No.: 16/399,597

(22) Filed: Apr. 30, 2019

(65) Prior Publication Data
US 2019/0367865 A1 Dec. 5, 2019

Related U.S. Application Data

(60) Provisional application No. 62/664,445, filed on Apr. 30, 2018.

(51) Int. Cl.
*C12N 1/20* (2006.01)
*C12N 9/10* (2006.01)
*C12P 9/00* (2006.01)

(52) U.S. Cl.
CPC ............ *C12N 1/20* (2013.01); *C12N 9/1085* (2013.01); *C12P 9/00* (2013.01); *C12Y 205/01054* (2013.01)

(58) Field of Classification Search
CPC ........................... C12P 9/00; C12Y 205/01054
See application file for complete search history.

(56) References Cited

U.S. PATENT DOCUMENTS 4,952,501 A 8/1990 Jasin et al.
2005/0221455 A1* 10/2005 McFarlan ................ C12N 9/88
435/121

FOREIGN PATENT DOCUMENTS

WO 2017151811 A1 9/2017

OTHER PUBLICATIONS

Kikuchi et al., "Mutational Analysis of the Feedback Sites of Phenylalanine-Sensitive 3-Deoxy-D-arabino-Heptulosonate-7-Phosphate Synthase of *Escherichia coli*", Applied and Environmental Microbiology, Feb. 1997, vol. 63, No. 2, pp. 761-762.
Nikel et al., "Pseudomonas putida KT2440 Strain Metabolizes Glucose through a Cycle Formed by Enzymes of the Entner-Doudoroff, Embden-Meyerhof-Parnas, and Pentose Phosphate Pathways", The Journal of Biological Chemistry, Oct. 2015, vol. 290, No. 43, pp. 25920-25932.
Poblete-Castro et al., "Improved Production of Medium-Chain-Length Polyhydroxyalkanoates in Glucose-Based Fed-Batch Cultivations of Metabolically Engineered Pseudomonas putida Strains", Journal of Microbiology and Biotechnology, Jan. 2014, vol. 24, No. 1, pp. 59-69.
Thompson et al., "Muconic Acid Production via Alternative Pathways and a Synthetic 'Metabolic Funnel'", ACS Synthetic Biology, 2018, vol. 7, pp. 565-575.

* cited by examiner

*Primary Examiner* — Maryam Monshipouri
(74) *Attorney, Agent, or Firm* — Sam J. Barkley; Michael A. McIntyre

(57) ABSTRACT

The present disclosure relates to a non-naturally occurring microorganism that includes an endogenous genetic deletion that eliminates the expression of at least a pyruvate kinase, where the genetically modified prokaryotic microorganism is capable of producing 3-deoxy-D-arabino-heptulosonate-7-phosphate.

6 Claims, 25 Drawing Sheets
Specification includes a Sequence Listing.

SEQUENCE LISTING

<160> NUMBER OF SEQ ID NOS: 44

<210> SEQ ID NO 1
<211> LENGTH: 31
<212> TYPE: DNA
<213> ORGANISM: Artificial Sequence
<220> FEATURE:
<223> OTHER INFORMATION: pK18mobsacB around the world R

<400> SEQUENCE: 1
ctaactcaca ttaattgcgt tgcgctcact g                                    31

<210> SEQ ID NO 2
<211> LENGTH: 45
<212> TYPE: DNA
<213> ORGANISM: Artificial Sequence
<220> FEATURE:
<223> OTHER INFORMATION: pK18mobsacB around the world F with EcoRI, XbaI, PstI, and BamHI sites

<400> SEQUENCE: 2
gaattcctgc agtctagagg atccctagct tcacgctgcc gcaag            45

<210> SEQ ID NO 3
<211> LENGTH: 60
<212> TYPE: DNA
<213> ORGANISM: Artificial Sequence
<220> FEATURE:
<223> OTHER INFORMATION: pykA upstream targeting F with pK18mobsacB overlap

<400> SEQUENCE: 3
gtgagcgcaa cgcaattaat gtgagttagg aattcaccgg taaagcggtt gaacaccttg            60

<210> SEQ ID NO 4
<211> LENGTH: 43
<212> TYPE: DNA
<213> ORGANISM: Artificial Sequence
<220> FEATURE:
<223> OTHER INFORMATION: pykA upstream targeting R with downstream targeting overlap

<400> SEQUENCE: 4
aacgagtgga gcggccgcat agtgaagcgc agcgaaaggc tac            43

<210> SEQ ID NO 5
<211> LENGTH: 44
<212> TYPE: DNA
<213> ORGANISM: Artificial Sequence
<220> FEATURE:
<223> OTHER INFORMATION: pykA downstream targeting F with upstream targeting overlap

<400> SEQUENCE: 5
gcgcttcact atgcggccgc tccactcgtt tcacagcaca aggc            44

<210> SEQ ID NO 6
<211> LENGTH: 56
<212> TYPE: DNA
<213> ORGANISM: Artificial Sequence
<220> FEATURE:
<223> OTHER INFORMATION: pykA downstream targeting R with pK18mobsacB targeting overlap

<400> SEQUENCE: 6
ccctgagtgc ttgcggcagc gtgaagctag ggatcccacc gagatcgaag cacgcg            56

<210> SEQ ID NO 7
<211> LENGTH: 18
<212> TYPE: DNA
<213> ORGANISM: Artificial Sequence
<220> FEATURE:
<223> OTHER INFORMATION: Diagnostic: outside pykA upstream targeting region F

<400> SEQUENCE: 7
caacccattt tcagaggc            18

-continued

```
<210> SEQ ID NO 8
<211> LENGTH: 18
<212> TYPE: DNA
<213> ORGANISM: Artificial Sequence
<220> FEATURE:
<223> OTHER INFORMATION: Diagnostic: outside pykA downstream targeting
      region R

<400> SEQUENCE: 8
aacaccacca tcatcgac                                                 18

<210> SEQ ID NO 9
<211> LENGTH: 57
<212> TYPE: DNA
<213> ORGANISM: Artificial Sequence
<220> FEATURE:
<223> OTHER INFORMATION: pykF upstream targeting F with pK18mobsacB
      overlap

<400> SEQUENCE: 9
agtgagcgca acgcaattaa tgtgagttag gaattcgcca cggtctacac ctatgcc      57

<210> SEQ ID NO 10
<211> LENGTH: 40
<212> TYPE: DNA
<213> ORGANISM: Artificial Sequence
<220> FEATURE:
<223> OTHER INFORMATION: pykF upstream targeting R with downstream
      targeting overlap

<400> SEQUENCE: 10
aatcgcggcc gctcatgatt gggcagtctc aaggatcagg                         40

<210> SEQ ID NO 11
<211> LENGTH: 41
<212> TYPE: DNA
<213> ORGANISM: Artificial Sequence
<220> FEATURE:
<223> OTHER INFORMATION: pykF downstream targeting F with upstream
      targeting overlap

<400> SEQUENCE: 11
gagactgccc aatcatgagc ggccgcgatt gccggggggcg c                      41

<210> SEQ ID NO 12
<211> LENGTH: 59
<212> TYPE: DNA
<213> ORGANISM: Artificial Sequence
<220> FEATURE:
<223> OTHER INFORMATION: pykF downstream targeting R with pK18mobsacB
      targeting overlap

<400> SEQUENCE: 12
ccctgagtgc ttgcggcagc gtgaagctag ggatcccatg ccgacgatga tcagcaacc    59

<210> SEQ ID NO 13
<211> LENGTH: 19
<212> TYPE: DNA
<213> ORGANISM: Artificial Sequence
<220> FEATURE:
<223> OTHER INFORMATION: Diagnostic: outside pykF downstream targeting
      region F

<400> SEQUENCE: 13
acaaggcgct gctgaaatc                                                19

<210> SEQ ID NO 14
```

```
<211> LENGTH: 18
<212> TYPE: DNA
<213> ORGANISM: Artificial Sequence
<220> FEATURE:
<223> OTHER INFORMATION: Diagnostic: outside pykF downstream targeting
      region R

<400> SEQUENCE: 14
cgcataggga ttgacgat                                                 18

<210> SEQ ID NO 15
<211> LENGTH: 60
<212> TYPE: DNA
<213> ORGANISM: Artificial Sequence
<220> FEATURE:
<223> OTHER INFORMATION: ppc upstream targeting F with pK18mobsacB
      overlap

<400> SEQUENCE: 15
agtgagcgca acgcaattaa tgtgagttag gaattctcgc tcaatccctg acataaccgc   60

<210> SEQ ID NO 16
<211> LENGTH: 39
<212> TYPE: DNA
<213> ORGANISM: Artificial Sequence
<220> FEATURE:
<223> OTHER INFORMATION: ppc upstream targeting R with downstream
      targeting overlap

<400> SEQUENCE: 16
gcttgcccgc ggccgcgttg catccctatc agcctcagc                          39

<210> SEQ ID NO 17
<211> LENGTH: 40
<212> TYPE: DNA
<213> ORGANISM: Artificial Sequence
<220> FEATURE:
<223> OTHER INFORMATION: ppc downstream targeting F with upstream
      targeting overlap

<400> SEQUENCE: 17
gatagggatg caacgcggcc gcgggcaagc ccgggtcatg                          40

<210> SEQ ID NO 18
<211> LENGTH: 60
<212> TYPE: DNA
<213> ORGANISM: Artificial Sequence
<220> FEATURE:
<223> OTHER INFORMATION: ppc downstream targeting R with pK18mobsacB
      targeting overlap

<400> SEQUENCE: 18
tgagtgcttg cggcagcgtg aagctaggga tccgaacggt ttcttccttg tcgtcgtcac   60

<210> SEQ ID NO 19
<211> LENGTH: 18
<212> TYPE: DNA
<213> ORGANISM: Artificial Sequence
<220> FEATURE:
<223> OTHER INFORMATION: Diagnostic: outside ppc downstream targeting
      region F

<400> SEQUENCE: 19
ctcctgataa cgacgatg                                                 18

<210> SEQ ID NO 20
<211> LENGTH: 18
```

```
<212> TYPE: DNA
<213> ORGANISM: Artificial Sequence
<220> FEATURE:
<223> OTHER INFORMATION: Diagnostic: outside ppc downstream targeting
      region R

<400> SEQUENCE: 20
cttggtctgg ctgtggta                                                  18

<210> SEQ ID NO 21
<211> LENGTH: 60
<212> TYPE: DNA
<213> ORGANISM: Artificial Sequence
<220> FEATURE:
<223> OTHER INFORMATION: pgi-1 upstream targeting F with pK18mobsacB
      overlap

<400> SEQUENCE: 21
gtgagcgcaa cgcaattaat gtgagttagg aattctcaca cttggcctga tcagggtttg    60

<210> SEQ ID NO 22
<211> LENGTH: 44
<212> TYPE: DNA
<213> ORGANISM: Artificial Sequence
<220> FEATURE:
<223> OTHER INFORMATION: pgi-1 upstream targeting R with NotI and
      downstream targeting overlap

<400> SEQUENCE: 22 gcagggggcgg ccgcgatacg ggtaaagcca gaacctatca atcg                    44

<210> SEQ ID NO 23
<211> LENGTH: 44
<212> TYPE: DNA
<213> ORGANISM: Artificial Sequence
<220> FEATURE:
<223> OTHER INFORMATION: pgi-1 downstream targeting F with NotI and
      upstream targeting overlap

<400> SEQUENCE: 23
tggctttacc cgtatcgcgg ccgcccctgc ttgatactgg cccg                     44

<210> SEQ ID NO 24
<211> LENGTH: 57
<212> TYPE: DNA
<213> ORGANISM: Artificial Sequence
<220> FEATURE:
<223> OTHER INFORMATION: pgi-1 downstream targeting R with pK18mobsacB
      targeting overlap

<400> SEQUENCE: 24
ccctgagtgc ttgcggcagc gtgaagctag ggatcctctg tggtaaggga gcgctcc       57

<210> SEQ ID NO 25
<211> LENGTH: 18
<212> TYPE: DNA
<213> ORGANISM: Artificial Sequence
<220> FEATURE:
<223> OTHER INFORMATION: Colony PCR: outside pgi-1 upstream targeting
      region F

<400> SEQUENCE: 25
gcttgtccaa tggcagtg                                                  18

<210> SEQ ID NO 26
<211> LENGTH: 19
<212> TYPE: DNA
```

<213> ORGANISM: Artificial Sequence
<220> FEATURE:
<223> OTHER INFORMATION: Colony PCR: outside pgi-1 downstream targeting
    region R

<400> SEQUENCE: 26
cgcagccagc aagatatag                                             19

<210> SEQ ID NO 27
<211> LENGTH: 56
<212> TYPE: DNA
<213> ORGANISM: Artificial Sequence
<220> FEATURE:
<223> OTHER INFORMATION: pgi-2 upstream targeting F with pK18mobsacB
    overlap

<400> SEQUENCE: 27
agtgagcgca acgcaattaa tgtgagttag gaattcggtg agggcaaacg catcgg     56

<210> SEQ ID NO 28
<211> LENGTH: 37
<212> TYPE: DNA
<213> ORGANISM: Artificial Sequence
<220> FEATURE:
<223> OTHER INFORMATION: pgi-2 upstream targeting R with NotI and
    downstream targeting overlap

<400> SEQUENCE: 28
caagctcgga gcggccgcgg tgcgtggtga gggcttg                         37

<210> SEQ ID NO 29
<211> LENGTH: 37
<212> TYPE: DNA
<213> ORGANISM: Artificial Sequence
<220> FEATURE:
<223> OTHER INFORMATION: pgi-2 downstream targeting F with NotI and
    upstream targeting overlap

<400> SEQUENCE: 29
tcaccacgca ccgcggccgc tccgagcttg tgccggc                         37

<210> SEQ ID NO 30
<211> LENGTH: 55
<212> TYPE: DNA
<213> ORGANISM: Artificial Sequence
<220> FEATURE:
<223> OTHER INFORMATION: pgi-2 downstream targeting R with pK18mobsacB
    targeting overlap

<400> SEQUENCE: 30
ccctgagtgc ttgcggcagc gtgaagctag ggatcccggt ggtatgcagc acccc      55

<210> SEQ ID NO 31
<211> LENGTH: 18
<212> TYPE: DNA
<213> ORGANISM: Artificial Sequence
<220> FEATURE:
<223> OTHER INFORMATION: Diagnostic: outside pgi-2 upstream targeting
    region F

<400> SEQUENCE: 31
acacgggttc agtgcatg                                              18

<210> SEQ ID NO 32
<211> LENGTH: 18
<212> TYPE: DNA
<213> ORGANISM: Artificial Sequence

```
<220> FEATURE:
<223> OTHER INFORMATION: Diagnostic: outside pgi-2 downstream targeting
      region R

<400> SEQUENCE: 32
gaaggtcatc gttgcctg                                                  18

<210> SEQ ID NO 33
<211> LENGTH: 53
<212> TYPE: DNA
<213> ORGANISM: Artificial Sequence
<220> FEATURE:
<223> OTHER INFORMATION: aroY F with aroG-D146N overlap

<400> SEQUENCE: 33
gctaatgcgg tcaaggcgcg tcggggctga agaggaggga gaatgcagaa ccc           53

<210> SEQ ID NO 34
<211> LENGTH: 143
<212> TYPE: DNA
<213> ORGANISM: Artificial Sequence
<220> FEATURE:
<223> OTHER INFORMATION: aroG-D146N opt P.p. F with synthetic RBS, Ptac,
      and upstream ?pykA overlap

<400> SEQUENCE: 34
caggagtagc ctttcgctgc gcttcactat gagctgttga caattaatca tcggctcgta    60
taatgtgtgg aattgtgagc ggataacaat ttcacacagg aggacttaca tgaactatca   120
gaatgatgac ttgcgcatca agg                                           143

<210> SEQ ID NO 35
<211> LENGTH: 60
<212> TYPE: DNA
<213> ORGANISM: Artificial Sequence
<220> FEATURE:
<223> OTHER INFORMATION: asbF opt P.p. R with PmeI and downstream ?pykA
      overlap

<400> SEQUENCE: 35
gcttgagcct tgtgctgtga acgagtgga gtttaaactc aggaggttac gacctccagc     60

<210> SEQ ID NO 36
<211> LENGTH: 18
<212> TYPE: DNA
<213> ORGANISM: Artificial Sequence
<220> FEATURE:
<223> OTHER INFORMATION: Diagnostic: outside gcd upstream targeting
      region F

<400> SEQUENCE: 36
tgcgctacaa ccttaccc                                                  18

<210> SEQ ID NO 37
<211> LENGTH: 18
<212> TYPE: DNA
<213> ORGANISM: Artificial Sequence
<220> FEATURE:
<223> OTHER INFORMATION: Diagnostic: outside gcd upstream targeting
      region R

<400> SEQUENCE: 37
taggctttga cctcgtcg                                                  18

<210> SEQ ID NO 38
<211> LENGTH: 46
```

```
<212> TYPE: DNA
<213> ORGANISM: Artificial Sequence
<220> FEATURE:
<223> OTHER INFORMATION: gcd upstream targeting F with pK18mobsacB
      overlap

<400> SEQUENCE: 38
agctcggtac ccggggatcc tctagagaac ccttccaacc tcgaat                    46

<210> SEQ ID NO 39
<211> LENGTH: 36
<212> TYPE: DNA
<213> ORGANISM: Artificial Sequence
<220> FEATURE:
<223> OTHER INFORMATION: gcd upstream targeting R with NotI and
      downstream targeting overlap

<400> SEQUENCE: 39
atcttggtgc ccagcgaatc gtaggttctc cgtcag                               36

<210> SEQ ID NO 40
<211> LENGTH: 36
<212> TYPE: DNA
<213> ORGANISM: Artificial Sequence
<220> FEATURE:
<223> OTHER INFORMATION: gcd downstream targeting F with NotI and
      upstream targeting overlap

<400> SEQUENCE: 40
ctgacggaga acctacgatt cgctgggcac caagat                               36

<210> SEQ ID NO 41
<211> LENGTH: 46
<212> TYPE: DNA
<213> ORGANISM: Artificial Sequence
<220> FEATURE:
<223> OTHER INFORMATION: gcd downstream targeting R with pK18mobsacB
      targeting overlap

<400> SEQUENCE: 41
gtaaaacgac ggccagtgcc aagcttgggt attcgacttc gaccag                    46

<210> SEQ ID NO 42
<211> LENGTH: 33
<212> TYPE: DNA
<213> ORGANISM: Artificial Sequence
<220> FEATURE:
<223> OTHER INFORMATION: asbF with synthetic RBS for KLD rxn F

<400> SEQUENCE: 42
gcccaaaatg aagtacagcc tgtgcaccat cag                                  33

<210> SEQ ID NO 43
<211> LENGTH: 33
<212> TYPE: DNA
<213> ORGANISM: Artificial Sequence
<220> FEATURE:
<223> OTHER INFORMATION: aroG-D146N with synthetic RBS for KLD rxn R

<400> SEQUENCE: 43
tcctctacgt gggtggcgtc agccccgacg cgc                                  33

<210> SEQ ID NO 44
<211> LENGTH: 1053
<212> TYPE: DNA
<213> ORGANISM: Artificial Sequence
<220> FEATURE:
```

<223> OTHER INFORMATION: The aroG gene from E. coli K-12 MG1655
      incorporating the D146N mutation was optimized for expression in
      P. putida KT2440

<400> SEQUENCE: 44

```
atgaactatc agaatgatga cttgcgcatc aaggaaatca aggagctgct gccgccggtg      60
gccctgttgg aaaagtttcc ggctaccgag aacgctgcca ataccgtcgc ccacgcacgc     120
aaggccatcc ataaaatcct gaagggcaac gatgatcgcc tgctggtggt gatcggtcct     180
tgtagcatcc acgacccggt ggcggccaaa gagtacgcca cccggttgct ggcattgcgc     240
gaggaactga aggacgagct ggaaatcgtc atgcgggtgt acttcgagaa gccacggacc     300
accgtcggct ggaagggcct gatcaacgac ccgcacatgg acaactcgtt ccagatcaac     360
gacggcctgc gtatcgcccg caagttgttg ctggacatca acgacagcgg cctgccggca     420
gccggcgagt tcttgaacat gatcacgccg cagtacctgg cggatctgat gtcgtggggc     480
gccatcggcg cacgcaccac cgagagccag gtgcatcgtg aactggcctc ggggctgtcc     540
tgccccgtgg gctttaagaa cggcaccgac gggaccatta aagtcgcaat cgatgcgatc     600
aatgcggcgg gcgccccgca ctgcttcctg tccgtgacca agtggggcca cagcgccatc     660
gtaaacacct cgggtaacgg ggactgccac atcatcctgc gtggtggcaa agagccgaac     720
tacagcgcca agcacgtggc ggaggtgaag gaaggcctga acaaagccgg cctgccggcg     780
caggtgatga tcgatttcag ccatgccaac tccagcaagc aattcaaaaa gcagatggat     840
gtgtcgcccg acgtgtgcca gcagatcgcc ggtggcgaaa aagccatcat cggggtaatg     900
gtggaatcgc atctggtgga gggcaatcaa tccctggaat cgggcgaacc cctggcctac     960
ggcaaaagca tcaccgatgc ctgcatcggc tgggaggaca ccgacgccct gctgcgccaa    1020
ctcgctaatg cggtcaaggc gcgtcggggc tga                                 1053
```

ENGINEERED MICROORGANISMS FOR THE PRODUCTION OF INTERMEDIATES AND FINAL PRODUCTS

CROSS-REFERENCE TO RELATED APPLICATIONS

This application claims priority under 35 U.S.C. 119(e) to U.S. Provisional Application No. 62/664,445 filed 30 Apr. 2018, the contents of which are incorporated herein by reference.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy as filed herewith was originally created on Aug. 27, 2019. The ASCII copy as filed herewith is named NREL 17-47_ST25.txt, is 12 kilobytes in size and is submitted with the instant application.

BACKGROUND

In order to drive innovation in chemical and material applications beyond what has been afforded by the now mature petrochemical industry, new molecules that possess diverse chemical moieties not readily accessed from petroleum are needed. One source of such molecules lies in the varied pathways soil microbes utilize to degrade the abundant aromatic compounds generated during plant decomposition. These pathways may converge at (or "funnel to") central aromatic intermediates including catechol, protocatechuate, and gallate. The aromatic rings of these compounds may be cleaved by ring-opening dioxygenase enzymes and their products may be metabolized through pathways that eventually enter central carbon metabolism for energy and growth. Intermediate compounds in these pathways provide significant and potentially enabling chemical functionality for biopolymer applications. Thus, there remains a need for improved compositions and methods that more effectively funnel biomass degradation products through pathways to produce intermediate molecules at higher yields, titers, growth rates, and/or efficiencies.

SUMMARY

An aspect of the present disclosure is a non-naturally occurring microorganism that includes an endogenous genetic deletion that eliminates the expression of at least a pyruvate kinase, where the genetically modified prokaryotic microorganism is capable of producing 3-deoxy-D-arabino-heptulosonate-7-phosphate. In some embodiments of the present disclosure, the pyruvate kinase includes at least one of PykA and/or PykF. In some embodiments of the present disclosure, the endogenous genetic deletion may further eliminate the expression of a glucose-6-phosphate isomerase. In some embodiments of the present disclosure, the glucose-6-phosphate isomerase may include at least one of Pgi-1 and/or Pgi-2.

In some embodiments of the present disclosure, the endogenous genetic deletion may further eliminate the expression of a glucose dehydrogenase. In some embodiments of the present disclosure, the glucose dehydrogenase may include Gcd. In some embodiments of the present disclosure, the endogenous genetic deletion may further eliminate the expression of a phosphoenolpyruvate carboxylase. In some embodiments of the present disclosure, the phosphoenolpyruvate carboxylase may include Ppc. In some embodiments of the present disclosure, the endogenous genetic deletion may further eliminate the expression of a transcriptional repressor. In some embodiments of the present disclosure, the transcriptional repressor may include HexR.

In some embodiments of the present disclosure, the genetically modified prokaryotic microorganism may further include an exogenous genetic addition encoding at least one of a DHAP synthase, a decarboxylase, and/or a dehydratase. In some embodiments of the present disclosure, the DHAP synthase may include AroG$^{D146N}$.

In some embodiments of the present disclosure, the genetically modified prokaryotic microorganism may be from the genus *Pseudomonas*. In some embodiments of the present disclosure, the genetically modified prokaryotic microorganism may be at least one of *P. putida*, *P. fluorescens*, and/or *P. stutzeri*. In some embodiments of the present disclosure, the genetically modified prokaryotic microorganism may be *P. putida* KT2440. In some embodiments of the present disclosure, the genetically modified prokaryotic microorganism may be capable of catabolizing at least one of a lignin depolymerization product, a cellulose depolymerization product, and/or a hemicellulose depolymerization product. In some embodiments of the present disclosure, the lignin depolymerization product may include an aromatic compound. In some embodiments of the present disclosure, the cellulose depolymerization product may include glucose.

In an aspect, disclosed herein is a non-naturally occurring microorganism comprising an endogenous genetic deletion that eliminates the expression of at least a pyruvate kinase, wherein the microorganism is capable of producing 3-deoxy-D-arabino-heptulosonate-7-phosphate. In an embodiment, the microorganism has a pyruvate kinase that comprises at least one of PykA or PykF. In an embodiment, the microorganism has an endogenous genetic deletion that further eliminates the expression of a glucose-6-phosphate isomerase. In an embodiment, the microorganism has glucose-6-phosphate isomerase that comprises at least one of Pgi-1 or Pgi-2. In another embodiment, the microorganism contains an endogenous genetic deletion that further eliminates the expression of a glucose dehydrogenase. In an embodiment, the microorganism has glucose dehydrogenase that comprises Gcd. In an embodiment, the microorganism has an endogenous genetic deletion that eliminates the expression of a phosphoenolpyruvate carboxylase. In another embodiment, the microorganism has a phosphoenolpyruvate carboxylase that comprises Ppc. In an embodiment, the microorganism contains an endogenous genetic deletion that further eliminates the expression of a transcriptional repressor. In another embodiment, the microorganism has a deletion of the transcriptional repressor comprises HexR. In an embodiment, the microorganism has an exogenous genetic addition encoding at least one of a DHAP synthase, a decarboxylase, or a dehydratase. In another embodiment, the microorganism has a DHAP synthase that comprises AroG$^{D146N}$. In yet another embodiment, the microorganism of is a genetically modified prokaryotic microorganism from the genus *Pseudomonas*. In yet another embodiment, the microorganism is selected from the group consisting of *P. putida*, *P. fluorescens*, and *P. stutzeri*. In an embodiment, the microorganism is *P. putida* KT2440. In yet another embodiment, the microorganism is capable of catabolizing at least one of a lignin depolymerization product, a cellulose depolymerization product, or a hemicellulose depolymerization product. In another embodiment, the lignin depolymerization product comprises an aromatic compound. In an embodiment, the cellulose depolymerization product comprises glucose. In another embodiment, the microorganism has a deletion of gacS. In an embodiment, the microorganism of has a deletion of gnd.

BRIEF DESCRIPTION OF THE DRAWINGS

Some embodiments are illustrated in referenced figures of the drawings. It is intended that the embodiments and figures disclosed herein are to be considered illustrative rather than limiting.

Exemplary embodiments are illustrated in referenced figures of the drawings. It is intended that the embodiments and figures disclosed herein are to be considered illustrative rather than limiting.

FIG. 7A depicts serial passaging of strain CJ522 was performed using 1% (vol/vol) of overnight culture to inoculate fresh M9 minimal medium containing 30 mM glucose (top left inset). After 45 generations, population GB038 demonstrated improved growth. Growth of evolved lineage GB038 is compared to clones isolated from population GB038 on a microplate reader. Deletion of gcd in CJ442 generated CJ522. Both parent strains are shown for comparison. Strain GB045 is a clonal isolate derived from population GB038 and was down-selected for further analysis. FIG. 7B depicts the growth rate of strains plotted by the time in hours required to reach the maximum specific growth rate (0.

FIG. 8A depicts production performance of CJ522, *P. putida* engineered for muconic acid production and lacks the glucose dehydrogenase (gcd). FIG. 8B depicts GB045, a clone resulting from evolution of strain CJ522. Strains were cultivated in M9 minimal medium containing 25 mM glucose. Culture growth was evaluated by measuring the OD600. Glucose and muconic acid concentrations were analyzed by HPLC. Each value represents the average of biological triplicates, with error bars representing the standard deviation of the replicates.

FIG. 9A depicts a representation of CatM activation of gene expression in the presence of muconate. FIG. 9B depicts flow cytometry histograms showing the enrichment of *P. putida* cells (CJ184) with diversified muconate sensor. PCA is a precursor of muconate.

FIG. 12A depicts production performance of GB205; FIG. 12B depicts GB206, and FIG. 12C depicts GB207. Strains were cultivated in M9 minimal medium containing 25 mM glucose. Culture growth was evaluated by measuring the OD600. Glucose and muconic acid concentrations were analyzed by HPLC. Each value represents the average of biological triplicates, with error bars representing the standard deviation of the replicates.

DETAILED DESCRIPTION

Figure 1:
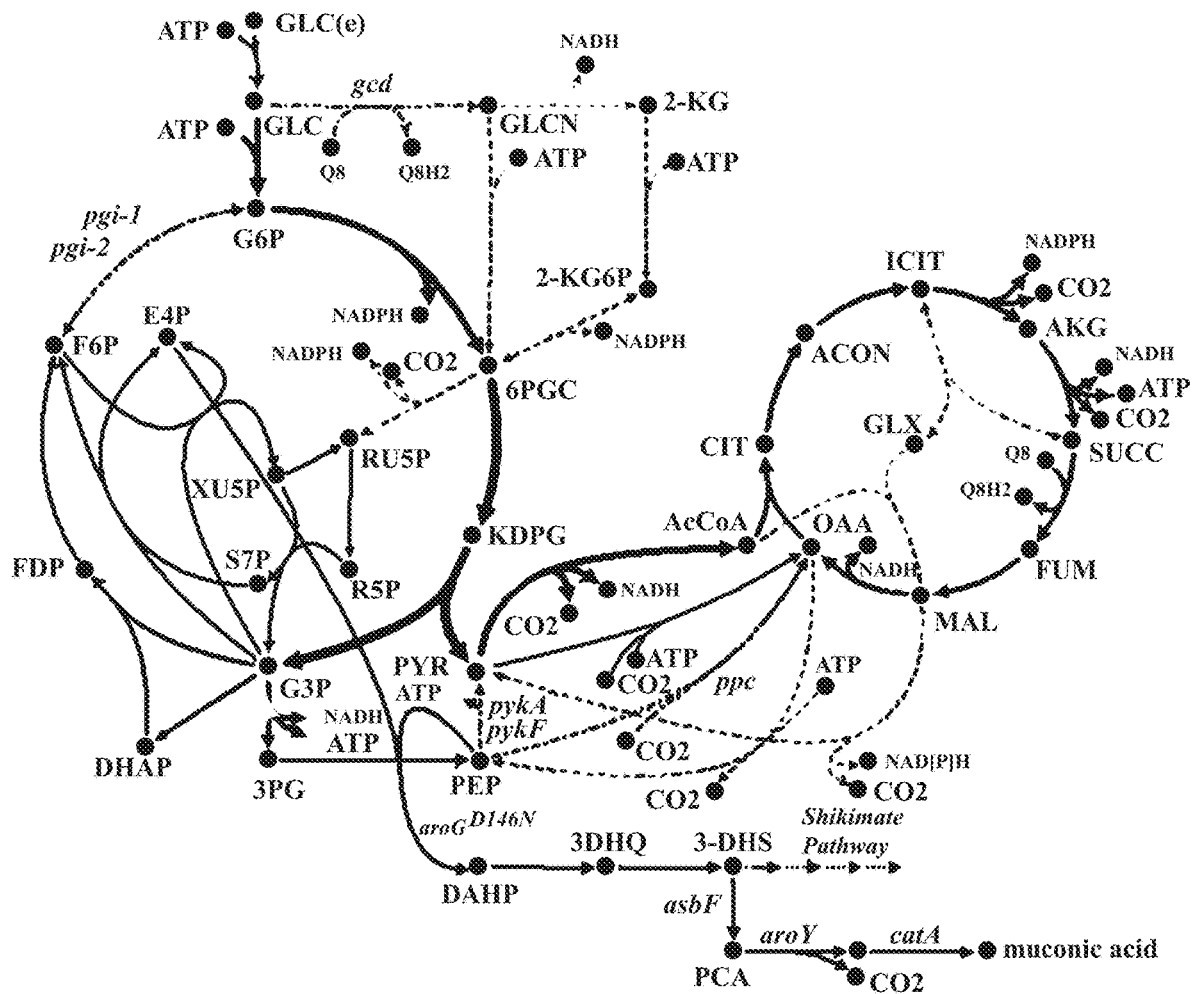
FIG. 1 illustrates a metabolic map applicable to *P. putida* KT2440, showing possible fluxes after deletion of pykA, pykF, ppc, pgi-1, and pgi-2, according to some embodiments of the present disclosure.

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. Similarly, expression and recombinant vectors may contain a counter-selectable marker, a gene encoding a protein that is lethal or inhibits growth of the host cell under certain conditions. The presence of this gene inhibits growth of or is lethal to those host cells that express the vector in the appropriate selective media. Markers may be an inducible or non-inducible gene and will generally allow for negative selection. Non-limiting examples of selectable markers include the sacB sucrose sensitivity marker (i.e., levasucrase), ccdB cell killing protein, thyAR trimethoprim sensitivity marker (thymidilate synthetase), lacYt-o-nitrophenyl-β-d-galactopyranoside sensitivity marker (lactose permease), and the like. The choice of the proper selectable or counter-selectable marker will depend on the host cell, and appropriate markers for different hosts or applications as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection or counter-selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

SEQ ID NOS: 1-66 provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library) and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR), de novo DNA synthesis, and/or cloning or assembling into a vector using restriction enzymes. Recombinant nucleic acids also include those that result from recombination events that occur through the natural mechanisms of cells but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T. viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori*, or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate culture medium. An appropriate, or effective, medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional bioreactors and by any cultivation process, including batch, fed-batch, cell recycle, and continuous cultivation, in the presence or the absence of on-line product extraction systems. The pH of the medium is regulated to a pH suitable for growth of the particular organism. Culture media and conditions for various host cells are known in the art. A wide range of media for culturing bacteria or fungi, for example, are available from ATCC. Exemplary culture conditions and reagents are provided in the Table 2 below. Media may be supplemented with aromatic substrates like benzoate or 4-hydroxybenzoate.

The nucleic acid molecules described herein encode the enzymes with amino acid sequences such as those represented by the sequences presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein or may include up to a certain integer number of amino acid alterations. Such protein or polypeptide variants retain functionality as enzymes, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Note regarding nomenclature: Modifications to microorganisms as described herein will be summarized in "shorthand" notation as follows. First, the gene or genes immediately following a Δ symbol have been deleted from the genome. A double-colon following the deleted gene(s) refers to replacing the deleted gene(s) with the genetic element, gene or genes that immediately follow the double-colon. Finally, the single colon refers to genetic fusion of the gene before the colon to the gene following the colon, where one genetic element or gene immediately precedes the next.

The present disclosure relates to genetically modified microorganisms. The terms genetically modified microorganisms and non-naturally occurring microorganisms may be used interchangeably herein. The terms genetically modified and genetically engineered may also be used interchangeably herein. Non-naturally occurring microorganisms as disclosed herein may include genetically engineered Pseudomonads (including *Pseudomonas putida*), *Acinetobacter* sp., various Rhodococci (e.g., *Rhodococcus erythryopolis*), *Sphingobium* sp., *Saccharomyces cerevisiae*, *Zygosaccharomyces bailii*, *Pichia kudriavzevii*, and *Candida glabrata* that have been metabolically engineered to direct various cellulose and hemicellulose derived intermediates (e.g. sugars and/or acetate) to form 3-deoxy-D-arabino-heptulosonate-7-phosphate (DAHP) which may subsequently enter the shikimate pathway to produce a variety of molecules including at least one of cis,cis-muconic acid, 2-hydroxy-2H-pyran-4,6-dicarboxylic acid, 2-oxo-2H-pyran-4,6-dicarboxylic acid, (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, (1E,3Z)-buta-1,3-diene-1,2,4-tricarboxylic acid, 2-carboxy-5-oxo-2,5-dihydrofuran-2-carboxylic acid, 2-(2-oxo-3H-furan-5-yl)acetic acid, 3-oxohexanedioic acid, (2E,4E)-2-formyl-5-hydroxyhexa-2,4-dienedioic acid, pyridine-2,5-dicarboxylic acid, (2Z,4E)-2-hydroxy-6-oxohexa-2,4-dienoic acid, pyridine-2-carboxylic acid, (2Z,4E)-2-hydroxyhexa-2,4-dienedioic acid, (3E)-2-oxohex-3-enedioic acid, (2E)-2-hydroxypenta-2,4-dienoic acid, and/or 4-hydroxy-2-oxopentanoic acid. Subsequently, any one of these 16 molecules may be reacted to produce various polymers and/or copolymers.

In the remainder of this disclosure, various target molecules produced using some embodiments of the engineered microorganisms described herein will following the numbering system below:

Molecule 1. 2-hydroxy-2H-pyran-4,6-dicarboxylic acid;
Molecule 1N. 3,5-Pyridinedicarboxylic acid
Molecule 2. 2-oxo-2H-pyran-4,6-dicarboxylic acid;
Molecule 3. (1E,3E)-4-hydroxybuta-1,3-diene-1,2,4-tricarboxylic acid;
Molecule 4. (1E)-4-oxobut-1-ene-1,2,4-tricarboxylic acid;
Molecule 5. 2-hydroxy-4-oxobutane-1,2,4-tricarboxylic acid;
Molecule 6. (1E,3Z)-buta-1,3-diene-1,2,4-tricarboxylic acid;
Molecule 7. 2-carboxy-5-oxo-2,5-dihydrofuran-2-carboxylic acid;
Molecule 8. 2-(2-oxo-3H-furan-5-yl)acetic acid;
Molecule 9. 3-oxohexanedioic acid;
Molecule 10. (2E,4E)-2-formyl-5-hydroxyhexa-2,4-dienedioic acid;
Molecule 10N. pyridine-2,5-dicarboxylic acid;
Molecule 11. (2Z,4E)-2-hydroxy-6-oxohexa-2,4-dienoic acid;
Molecule 11N. pyridine-2-carboxylic acid;
Molecule 12. (2Z,4E)-2-hydroxyhexa-2,4-dienedioic acid;
Molecule 13. (3E)-2-oxohex-3-enedioic acid;
Molecule 14. (2E)-2-hydroxypenta-2,4-dienoic acid; and
Molecule 15. 4-hydroxy-2-oxopentanoic acid.

These seventeen molecules will be referred to by their respective numbers throughout the remainder of this disclosure. For example, 3-oxohexanedioic acid will be referred to as "molecule #9" or "#9" or "(#9)" or "9".

Referring to FIG. 1, the present disclosure relates to microorganisms having at least one genetic modification made to at least one pathway that results in at least one of more effective growth of the modified microorganism and/or more effective conversion of various cellulose degradation products and/or hemicellulose degradation products to at least one of DAHP, PEP, E4P, 3PB, and/or G3P. Referring again to FIG. 1, the abbreviations refer to the following molecules: 3-deoxy-D-arabino-heptulosonate-7-phosphate (DAHP), 2-dehydro-3-deoxy-D-gluconate 6-phosphate (KDPG), 2-Dehydro-D-gluconate (2-KG), protocatechuate (PCA), 3-dehydroquinate (3DHQ), 3-dehydroshikimate (3-DHS), 3-Phospho-D-glycerate (3PG), 6-Phospho-2-dehydro-D-gluconate (2-KG6P), 6-Phospho-D-gluconate (6PGC), Acetyl-Coenzyme A (AcCoA), cis-Aconitate (ACON), 2-Oxoglutarate (AKG), catechol (CAT), Citrate (CIT), Dihydroxyacetone phosphate (DHAP), D-Erythrose 4-phosphate (E4P), D-Fructose 6-phosphate (F6P), D-Fructose 1,6-bisphosphate (FDP), Fumarate (FUM), Glyceraldehyde 3-phosphate (G3P), D-Glucose 6-phosphate (G6P), D-Glucose (GLC), Extracellular D-Glucose (GLC(e)), D-Gluconate (GLCN), Glyoxylate (GLX), Isocitrate (ICIT), L-Malate (MAL), Oxaloacetate (OAA), Phosphoenolpyruvate (PEP), Pyruvate (PYR), alpha-D-Ribose 5-phosphate (R5P), D-Ribulose 5-phosphate (RU5P), Sedoheptulose 7-phosphate (S7P), Succinate (SUCC), D-Xylulose 5-phosphate (XU5P).

In some embodiments of the present disclosure, a genetically modified microorganism may include modifying at least one gene encoding at least one of an endogenous pyruvate kinase, which converts PEP to pyruvate, with examples of pyruvate kinases including PykA and/or PykF, with the corresponding genes encoding these enzymes represented by pykA and pykF respectively. In some embodiments of the present disclosure, the modifying at least one gene encoding at least one endogenous pyruvate kinase may including removing the at least one gene, and or modifying it such that the pyruvate kinase does not function properly or is deficient at functioning as a pyruvate kinase.

In some embodiments of the present disclosure, a genetically modified microorganism may include modifying at least one gene encoding an endogenous phosphoenolpyruvate carboxylase (PPC), which carboxylates PEP to produce oxaloacetate, with an example of a phosphoenolpyruvate carboxylase being Ppc, with the corresponding gene encoding Ppc represented by ppc. In some embodiments of the present disclosure, the modifying of an endogenous phosphoenolpyruvate carboxylase may include removing the gene, and or modifying it such that the phosphoenolpyruvate carboxylase does not function properly or is deficient at functioning as a phosphoenolpyruvate carboxylase.

In some embodiments of the present disclosure, a genetically modified microorganism may include modifying at least one gene encoding an endogenous glucose-6-phosphate isomerase (Pgi), encoded by either gene pgi-1 and/or pgi-2. In some embodiments of the present disclosure, the modifying of an endogenous glucose-6-phosphate isomerase may include removing the gene, and or modifying it such that the glucose-6-phosphate isomerase does not function properly or is deficient at functioning as a glucose-6-phosphate isomerase.

In some embodiments of the present disclosure, a genetically modified microorganism may include modifying at least one gene encoding an endogenous glucose dehydrogenase, with an example of a glucose dehydrogenase being Gcd, with the corresponding gene encoding Gcd represented by gcd. In some embodiments of the present disclosure, the modifying of an endogenous phosphoenolpyruvate carboxylase may include removing the gene, and or modifying it such that the phosphoenolpyruvate carboxylase does not function properly or is deficient at functioning as a phosphoenolpyruvate carboxylase.

In some embodiments of the present disclosure, a genetically modified microorganism may include modifying at least one gene encoding an endogenous transcriptional repressor, with an example of a transcriptional repressor being HexR, with the corresponding gene encoding HexR represented by hexR. In some embodiments of the present disclosure, the modifying of an endogenous transcriptional repressor may include removing the gene, and or modifying it such that the endogenous transcriptional repressor does not function properly or is deficient at functioning as a transcriptional repressor.

Figure 2:
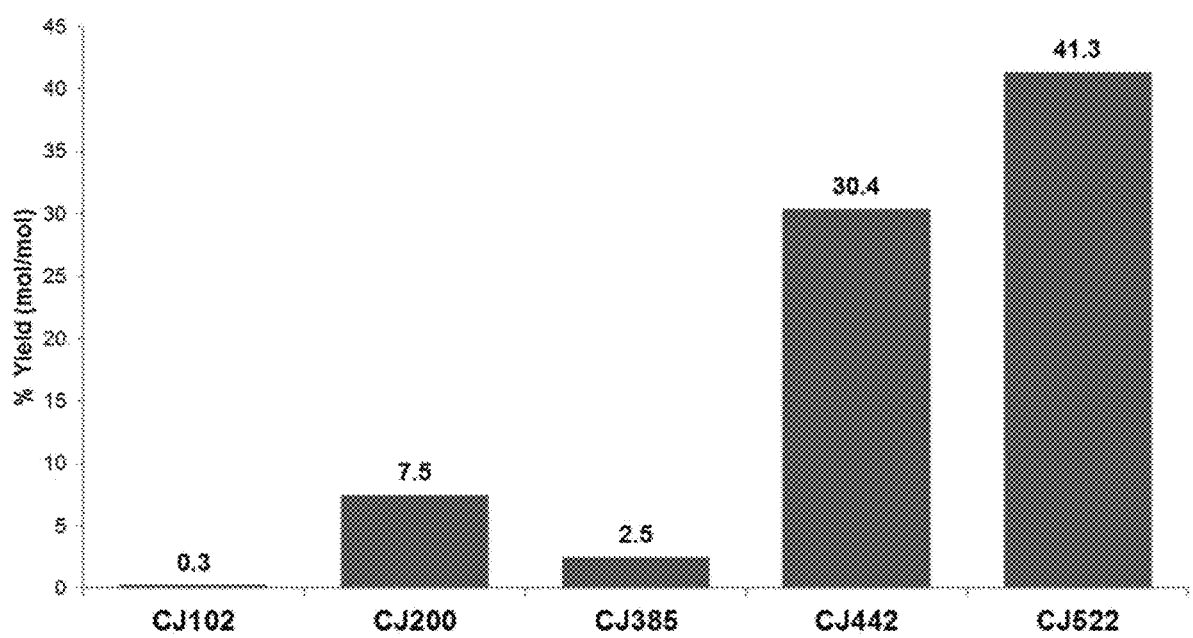
FIG. 2 illustrates a comparison of muconic acid yield obtained from various engineered microorganisms, according to some embodiments of the present disclosure.
Figure 3A:
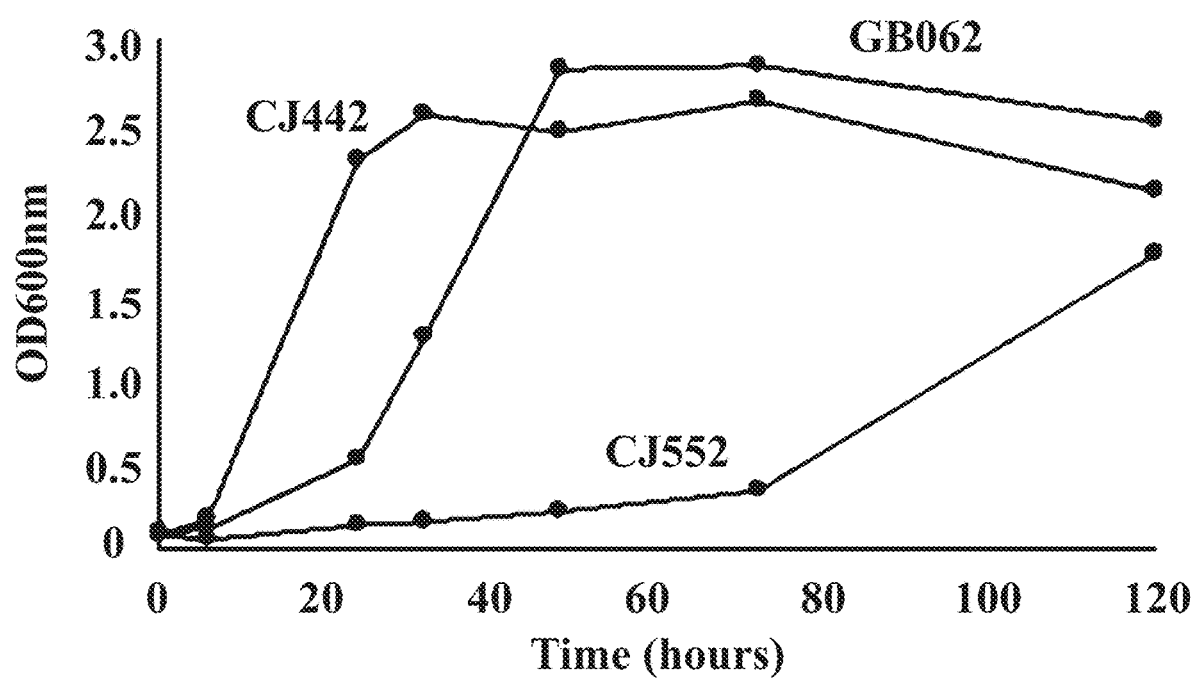
FIGS. 3A and 3B illustrate microorganism growth rates and muconic acid concentrations versus time, for several engineered strains of microorganisms, according to some embodiments of the present disclosure.
Figure 3B:
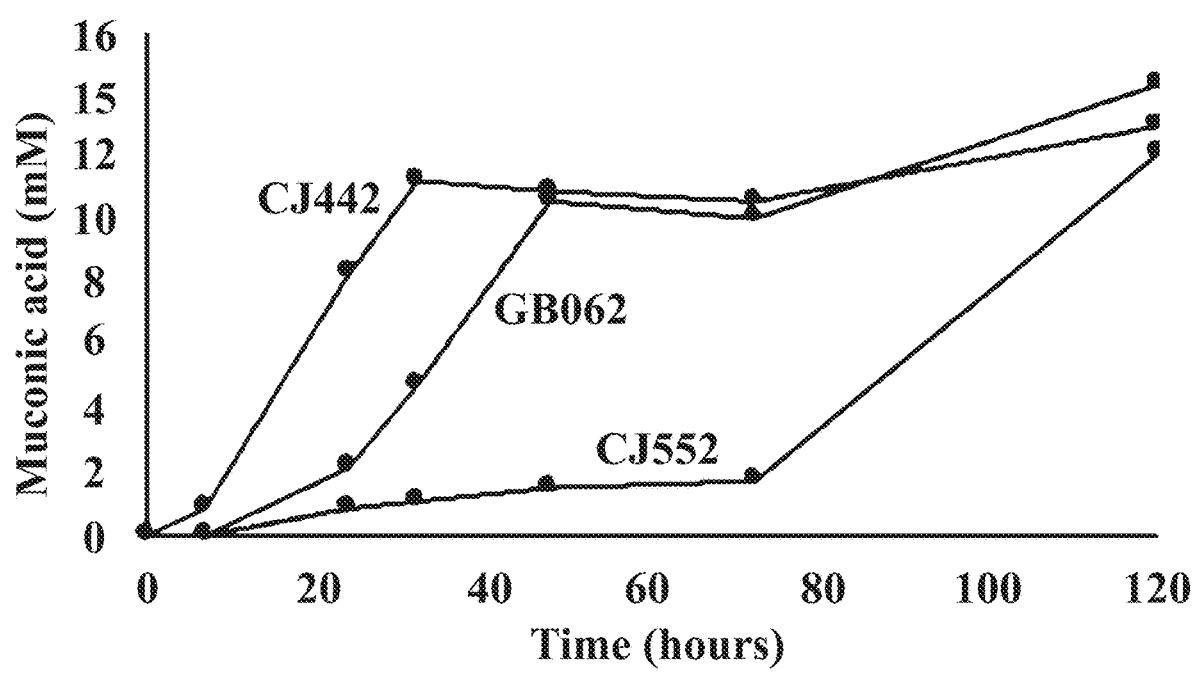

In some embodiments of the present disclosure, a genetically modified microorganism may include replacing at least one endogenous gene with at least one exogenous gene. Examples of exogenous genes that fall within the scope of the present disclosure include a DHAP synthase, for example a DHAP synthase from *E. Coli* such as AroG$^{D146N}$. Other examples of endogenous genes that may be introduced to the genetically modified microorganism include at least one of a decarboxylase and/or decarboxylase subunit with examples including enzymes from *Enterobacter cloacae* subsp. *cloacae* (ATCC 13047), EcdB and EcdD along with AroY (also from *Enterobacter cloacae* subsp. *cloacae* (ATCC 13047). In some embodiments of the present disclosure, at least one exogenous dehydratase may be engineered into a microorganism, where the exogenous dehydratase may be encoded by AsbF Table 1 below summarizes some strains of *P. Putida* that were modified as described above and FIG. 2 illustrates experimental results of these strains' abilities to produce cis, cis-muconic acid, through the DAHP, 3DHQ, 3-DHS, PCA pathway shown in FIG. 1. More details about the strain constructs, including plasmid construction details, primer sequences, and synthesized DNA fragments are provided in at least Tables 4, 5, and 6. FIG. 2 illustrates that, relative to strain CJ102, strain CJ442 exhibits a greater than 100 fold increase in muconic acid yield, while strain CJ522 exhibits almost 140 fold increase in muconic acid yield.

TABLE 1

*P. Putida* Strain Constructs

| Strain | Genotype |
|---|---|
| CJ200 | *P. putida* KT2440 ΔcatRBCA::Ptac:catA ΔpcaHG::Ptac:aroY:ecdB:asbF |
| CJ385 | *P. putida* KT2440 ΔcatRBCA::Ptac:catA ΔpcaHG::Ptac:aroY:ecdB:asbF ΔpykA ΔpykF Δppc Δpgi-1 Δpgi-2 |
| CJ442 | *P. putida* KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 |
| CJ522 | *P. putida* KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd |
| CJ598 | *P. putida* KT2440 ΔpykA::Ptac:aroG-D146N:asbF ΔpykF Δppc Δpgi-1 Δpgi-2 ΔpcaHG::Ptac:ligABC Δgcd |
| CJ599 | *P. putida* KT2440 ΔpykA::Ptac:aroG-D146N:asbF ΔpykF Δppc Δpgi-1 Δpgi-2 ΔpcaHG::Ptac:praA Δgcd |

Referring again to FIG. 1, to convert aromatic molecules metabolized via protocatechuate and catechol to the 16, were constructed that contain incomplete pathways for their catabolism. *P. Putida* can utilize the ortho-cleavage pathways for catabolism of protocatechuate and catechol, which ultimately converge in the β-ketoadipate pathway. To accumulate intermediates in this pathway, genes encoding the enzymes that act upon each targeted intermediate (Molecules 1-9, 16) were deleted from genome of *P. putida* KT2440. Protocatechuate and catechol may be metabolized through meta-cleavage pathways. To produce the targeted intermediates in these pathways, the endogenous genes encoding the ring-cleavage dioxygenases that initiate catabolism of protocatechuate and catechol in *P. putida* KT2440, pcaHG and catA/catA2, respectively, were deleted from the genome and replaced with genes encoding incomplete pathways derived from *Sphingobium* sp. strain SYK-6, *Paenibacillus* sp. strain JJ-1b, and/or *P. putida* mt-2. Small, shake-flask cultures of these engineered strains were then grown on glucose in the presence of 4-hydroxybenzoate or benzoate, which were metabolized via protocatechuate or catechol, respectively, and the supernatants were analyzed by HPLC, Positive- and negative-ion electrospray (ESI)-MS, and tandem mass spectrometry (MS/MS) were used to determine if the targeted intermediates were produced. Due to the presence of nitrogen in the fermentation media and the complex aldehyde functionality of Molecules 1, 10, and 11, these molecules can spontaneously ring close to produce Molecules 1N, 10N, and 11N. In all cases, the expected molecules were detected.

Considerable yields and titers of many of the targeted compounds were achieved from the aromatic lignin model compounds. In addition, cellulose and/or hemicellulose degradation products were also evaluated, using glucose as a model compound. Similar to the strains described for the production of the molecules targeting above, muconic acid can accumulate in this engineered *P. putida* strain, KT2440-CJ200, due to the deletion of the gene encoding CatB, which is used for further metabolism. KT2440-CJ200, however, only achieved a yield of 7.7% (mol/mol) of muconic acid from glucose, well below the theoretical maximum of 73.9%. As such, modifications to KT2440-CJ200 were investigated with the goal of increasing the yield of muconic acid from glucose. Subsequently, these learnings obtained from these metabolic perturbations were applied as the foundation for strains engineered for production of other targets molecules, including those derived from aromatic catabolic pathways.

In strains engineered to produce muconic acid from glucose, two key intermediates of sugar metabolism, erythrose 4-phosphate (E4P) and phosphoenol pyruvate (PEP) are condensed to form 3-deoxy-D-arabino-heptulosonate-7-phosphate (DAHP) and enter the shikimate pathway for subsequent conversion to muconic acid as described above (see FIG. 1). The shikimate pathway is the predominant fate for E4P in the cell, but PEP is almost exclusively metabolized to pyruvate, which is subsequently converted to acetyl-CoA for entry into the TCA cycle where it can be oxidized to $CO_2$ and generate biosynthetic intermediates, reducing equivalents, and ATP required for growth. Thus, competition for PEP between the shikimate pathway and growth is likely to be important for production of muconic acid.

The *P. putida* genome contains two genes encoding pyruvate kinases, pykA and pykF, which serve to convert PEP to pyruvate. Ppc is encoded by a single gene, ppc, and allows PEP to enter the TCA cycle by being carboxylated to generate oxaloacetate. As shown in FIG. 1, deletion of pykA, pykF, and ppc together serve to block PEP from directly entering the TCA cycle. Surprisingly, elimination of these two reactions alone was insufficient in improving muconic acid yields from glucose as confirmed by both experimental and modeling results. Flux balance simulations showed that near-optimal growth rates could be recovered after deletion of pykA,pykF, and ppc by reflux of glyceraldehyde-3-phosphate (G3P) through the EDEMP cycle: a combination of the ED pathway, pentose phosphate (PP) pathway, and gluconeogenic Embden-Meyerhof-Parnas (EMP) pathway. Thus, in the absence of PykA, PkyF, and Ppc, *P. putida* can use the EDEMP cycle to deliver carbon to the TCA cycle while bypassing PEP. To prevent this, the glucose-6-phosphate isomerases (Pgi) encoded by pgi-1 and pgi-2 were deleted to interrupt the EDEMP cycle.

Surprisingly, deletion of pykA, pykF, ppc, pgi-1, and pgi-2 from KT2440-CJ200, generating KT2440-CJ385, resulted in a dramatic reduction in muconic acid yield by the resulting strain, from 6.8% (mol/mol) to 2.4% (mol/mol). Interestingly, growth was also diminished, suggesting successful inhibition of growth via PEP and that carbon was likely available, but failed to flow into the shikimate pathway for conversion to muconic acid. It was hypothesized that expression of a feedback-resistant DAHP synthase or increased expression of the heterologous pathway from 3-DHS to catechol, or both, may draw more carbon into to muconic acid production via the shikimate pathway. Plasmid-based over-expression of genes encoding the heterologous part of the muconic acid pathway (asbF-aroY-ecdB), increased the yield from glucose to 6.1% (mol/mol) from the 1.3% (mol/mol) achieved by the parent strain KT2440-CJ385, carrying an empty vector, while plasmid-based expression of a feedback resistant mutant DHAP synthase from *E. coli*, $AroG^{D146N}$, increased the yield to 30.1% (mol/mol), and plasmid expression of $aroG^{D146N}$-asbF-aroY-ecdB further increased the yield to 33.8% (mol/mol). These results demonstrated that expression of the feedback resistant DAHP synthase and increased expression of the exogenous production pathway resulted in substantial increases in muconic acid yields. Because plasmid-based expression is generally incompatible with industrial bio-production due to the necessity for antibiotics to maintain the plasmid and potential instability, we constructed a strain, CJ442, with the $aroG^{D146N}$-asbF-aroY-ecdB gene cassette integrated into its genome and found that it yielded 36.0% (mol/mol) muconic acid from glucose.

In wild-type *P. putida* KT2440 about 90% of glucose may be dehydrogenated to gluconate and about 10% of that may be further dehydrogenated to generate 2-ketogluconate (2-KG). These pathways converge at 6-phosphogluconate, which can be further metabolized in the PP or ED pathways (see FIG. 1). It was observed that large amounts of 2-KG were secreted into the medium when CJ442 was cultivated in a bioreactor. This could negatively impact a production process in two ways. First, it could reduce the overall yield if the 2-KG is not metabolized completely and methods of detecting and quantifying 2-KG to evaluate this are not as rapid or facile as those for glucose. Its secretion also results in a substantial increase in the pH of the medium that must then be neutralized, resulting in additional cost. For these reasons, it was decided to eliminate the conversion of glucose to gluconate, and subsequently 2-KG, by deleting the glucose dehydrogenase gene, gcd, generating CJ522.

Next, the metabolic engineering that enabled the production of muconic acid at a high yield from glucose was applied for production of other molecules from aromatic catabolic pathways. Specifically, pykA, pykF, ppc, pgi-1, pgi-2, and gcd were deleted and genes encoding AsbF, and $AroG^{D146N}$ were integrated into the strains that had been engineered to produce molecules 2 (PDC), 10, and 11, generating CJ598, CJ599, and CJ596 strains, respectively. These strains were then evaluated in bioreactors using a fed-batch mode (see FIGS. 6A and 6B). CJ598 produced 13 g/L of Molecule 2, at a yield of 34%, and a productivity of 0.1 g/L/h (see FIGS. 6A and 6B), very similar to the titer, yield, and productivity obtained for muconic acid by CJ522 in fed-batch mode. CJ599 and CJ596 produced a mixture of Molecule 10 and 11 in both cases at very low titers (<0.1 g/L), excluding the production of Molecule 11 (surprisingly, by CJ599) which reached values up to 0.7 g/L at a yield of 35%.

Strain CJ442 was engineered for the production of muconic acid but accumulated significant amounts of 2-ketogluconate as a byproduct of glucose metabolism. To eliminate accumulation of 2-ketogluconate in strain CJ442, the glucose dehydrogenase gene was deleted (encoded by gcd), yielding strain CJ522. Strain CJ522 no longer accumulates 2-ketogluconate, but the growth was dramatically reduced (see FIG. 4A). To overcome that growth defect, it was discovered that the deletion of the transcriptional repressor HexR (encoded by hexR) could largely overcome the observed growth defect in CJ522. Importantly, by deleting hexR from CJ522, the rate of muconic acid production was increased and the yield of muconic acid from glucose is even higher than from the parent strain CJ522 (see FIG. 4B). More broadly, the deletion of hexR in any strain also lacking gcd may improve the growth of *Pseudomonas putida* KT2440 on glucose for the production of any target molecule. Together, elimination of 2-ketogluconate (deletion of gcd) can avoid the accumulation of an acidic byproduct at high titers, and the deletion of hexR overcomes the observed growth defect when the pathway to 2-ketogluconate is eliminated. Thus, these two genetic modifications in tandem improve the productivity of any strain using glucose as a substrate in KT2440.

Deletion of two additional genes which were mutated in evolved isolates, gntZ and gacS, further improves strain performance, providing a suite of modifications that can be combined for optimal *P. putida* strain performance in the context of gcd deletion. Bioreactor cultivations of the best-performing evolved clones and engineered strains reached 21.9 g/L (35.5% mol/mol) and 16.6 g/L (35.0% mol/mol), respectively. While these results enabled enhanced muconic acid production, the findings disclosed herein may generally improve production of any target molecule from glucose in *P. putida* when it is desirable to avoid 2-ketogluconate accumulation.

Figure 4A:
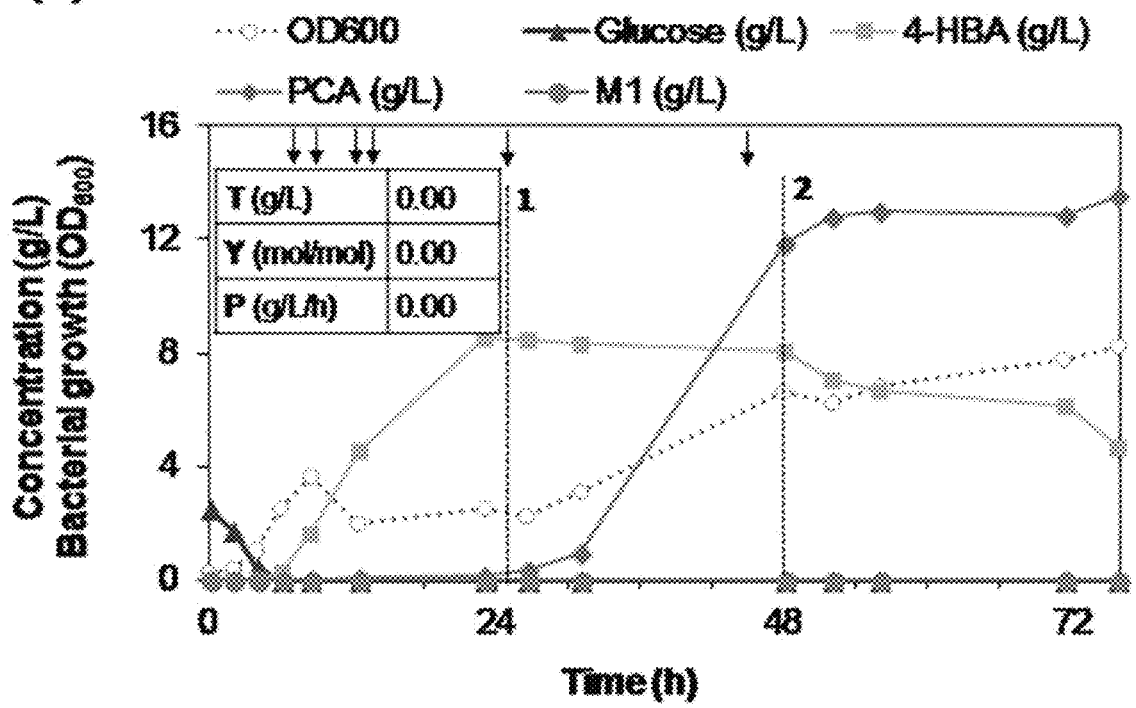
FIGS. 4A-4H illustrate bioreactor fermentation profiles obtained from fifteen different *P. putida* strains producing Molecule 1 to 15 from aromatic compounds, according to some embodiments of the present disclosure.
Figure 4A:
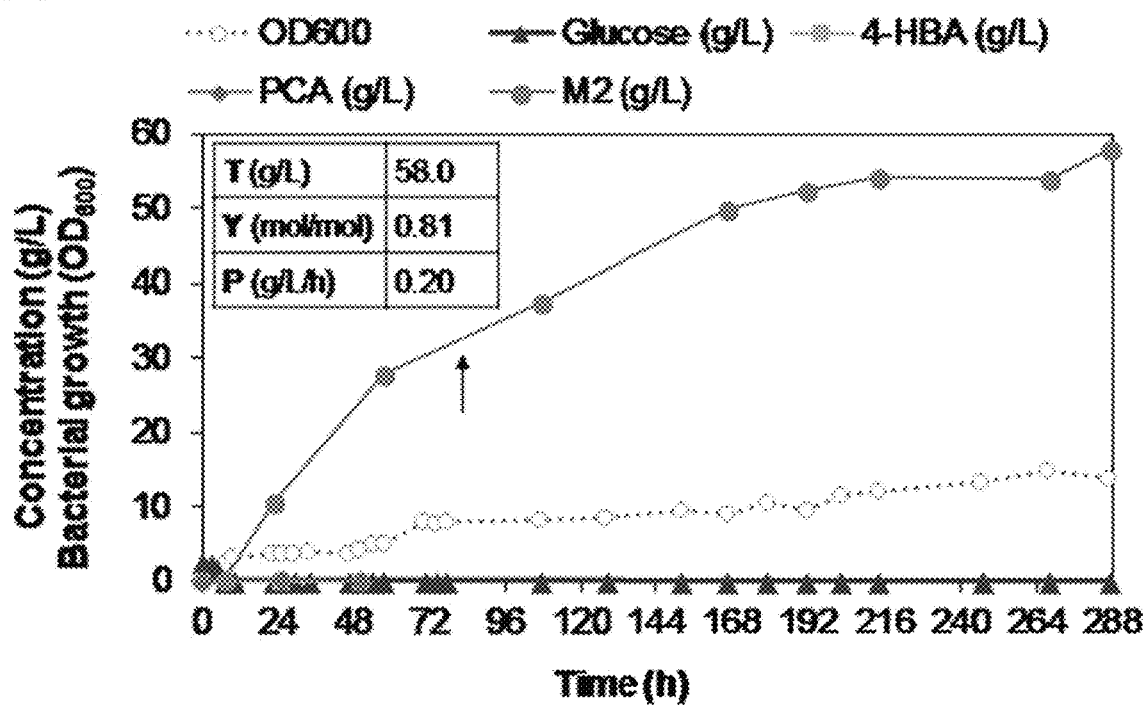

FIGS. 4A-4H illustrate bioreactor fermentation profiles obtained from fifteen different *P. putida* strains producing Molecule 1 to 15 from aromatic compounds, according to some embodiments of the present disclosure. A detailed explanation for each case is subsequently given. Titers (T), yields (Y), and productivity (P) are also highlighted for each molecule in the corresponding graph. Titers (g/L) correspond to product concentration at the end of the cultivation time. Yield (mol/mol) is calculated as product mols at the last time point (which is corrected by the dilution factor generated by base and feeding addition) divided by the total mols of substrate utilized (in this case glucose). Productivity (g/L/h) is calculated as product concentration at the last time point divided by the total cultivation time. 4-HBA=4-hydroxybenzoic acid; BA=benzoic acid; PCA=protocatechuic acid; OD600=Bacterial growth by measuring optical density at 600 nm. Referring to FIG. 4A, the production of Molecule 1 by *P. putida* CJ250/249 from 4-HBA was pursued three times. The first bioreactor run (in a 10 bioreactor) is shown in the graph. The second and third trial were repeated in similar conditions in 10 L and 2.5 L bioreactors but adding pulses of 2 N (NH$_4$)$_2$SO$_4$ (50 mL) twice per day. Molecule 1 was not detected in any case, only the accumulation of substrate and metabolic intermediates. Arrows indicate the addition of 40 mL of a solution containing 100 g/L glucose and 15 g/L (NH$_4$)$_2$SO$_4$. This solution was added to try to stabilize DO oscillations by increasing cell density and forcing the consumption of substrate and/or intermediates. (1) The feeding solution was replaced by another solution containing 100 g/L glucose and 15 g/L (NH$_4$)$_2$SO$_4$, (2) The feeding solution was again replaced by the initial solution containing 4-HBA.

Referring to FIG. 4A, the production of Molecule 2 by *P. putida* CJ251 from 4-HBA was conducted twice, in a 10 L and 2.5 L bioreactor. Molecule 2 was the major metabolite detected in both cases. The graph presents the results from the 2.5 L bioreactor run, which was maintained 2-fold longer than the 10 L bioreactor run. The arrow highlights a change in the feeding solution concentration from 160 g/L 4-HBA to 120 g/L, both in the presence of 100 g/L glucose and 15 g/L (NH$_4$)$_2$SO$_4$.

Figure 4B:
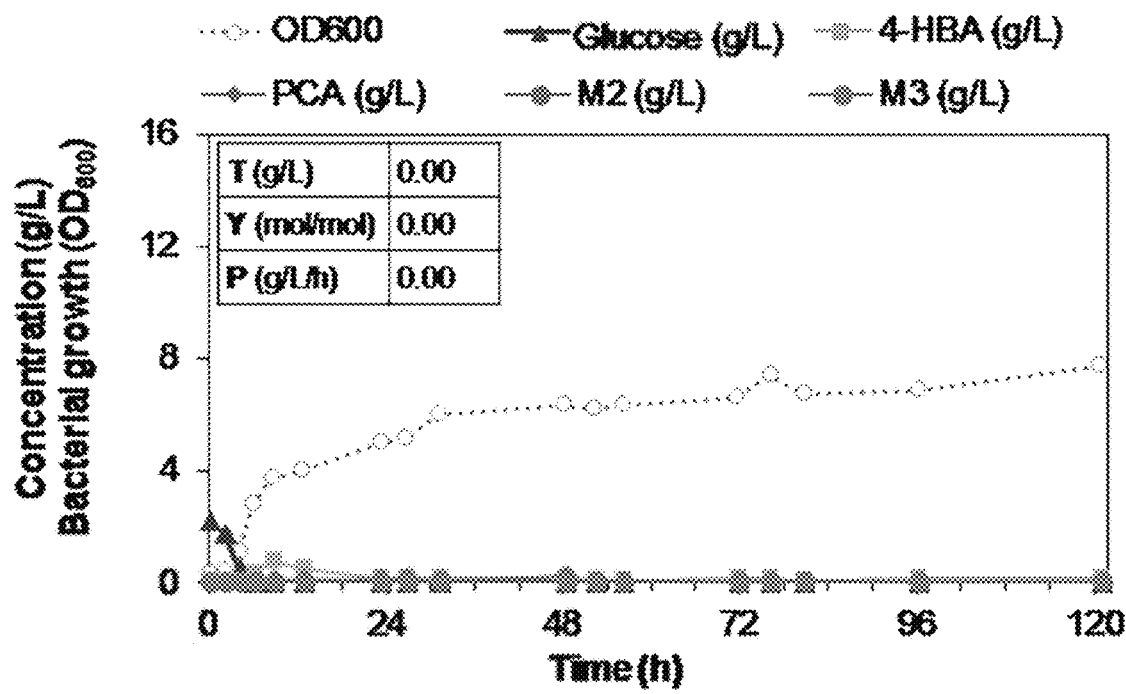
Figure 4B:
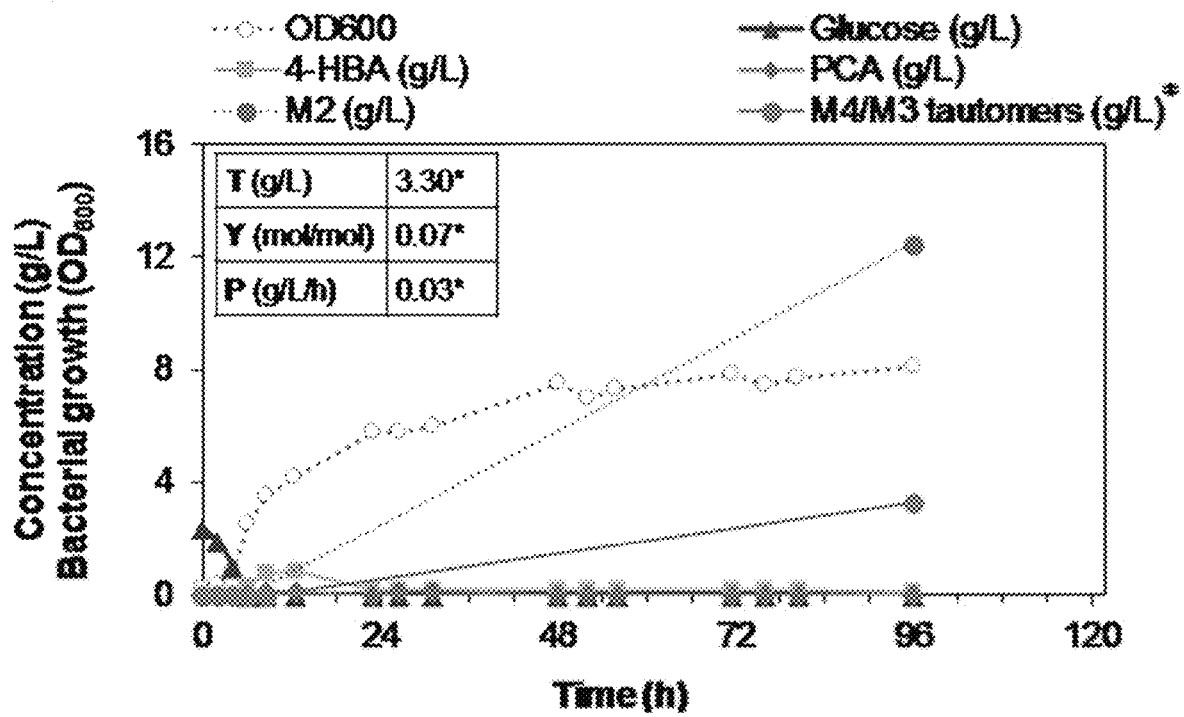

Referring to FIG. 4B, the production of Molecule 3 by *P. putida* CJ350 was conducted once in a 10 L bioreactor. This strain grew adequately, presented stable DO profiles, and consumed approximately 28 g/L of 4-HBA. However, molecule 3 was not detected and only 0.1 g/L of molecule 2 was identified. Referring again to FIG. 4B, the production of Molecule 4 by *P. putida* CJ328 was conducted once in a 10 L bioreactor. This strain grew adequately, presented stable DO profiles, and consumed approximately 31 g/L of 4-HBA. However, tautomers of Molecule 3 and 4 were found only up to 3.4 g/L and 12.5 g/L of Molecule 2 was accumulated. (*) Molecule 3 and 4 tautomers.

Figure 4C:
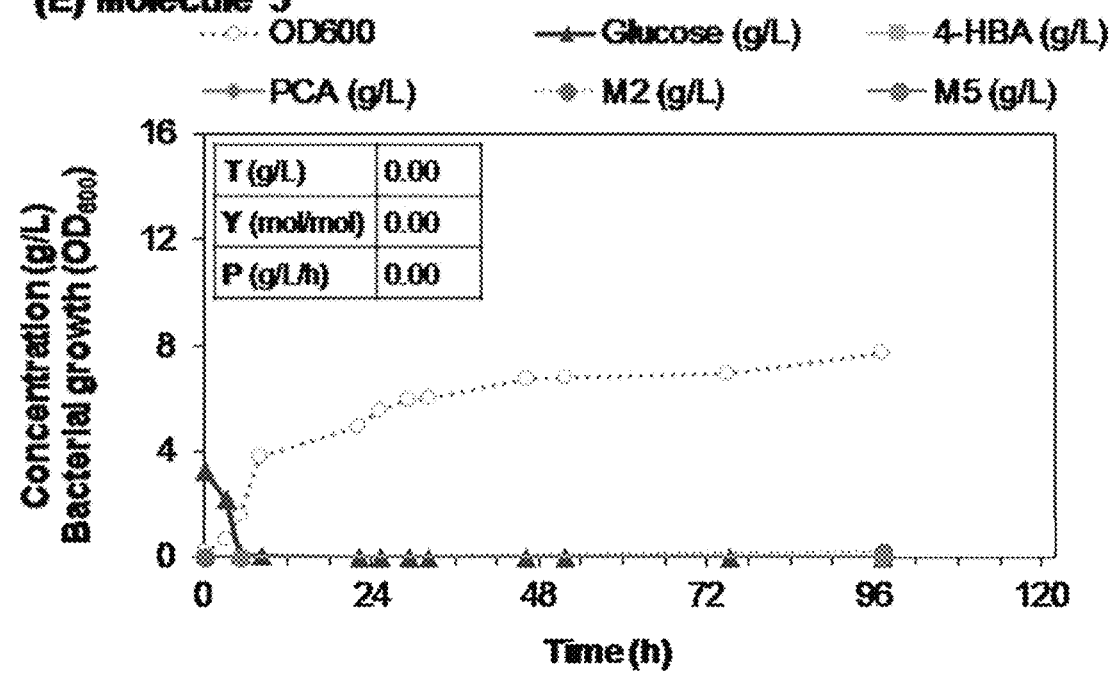
Figure 4C:
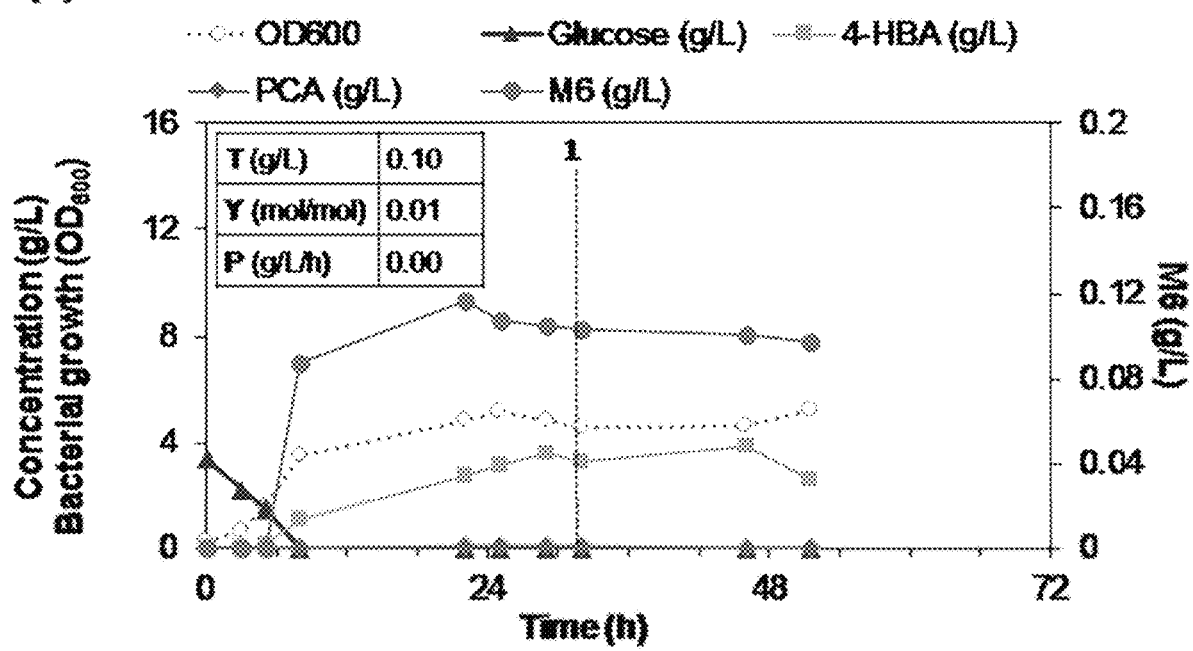

Referring to FIG. 4C, the production of Molecule 5 by *P. putida* CJ329 was conducted once in a 10 L bioreactor. This strain grew adequately, presented stable DO profiles, and consumed approximately 31 g/L of 4-HBA. However, molecule 5 was not detected and only 0.2 g/L of molecule 2 was identified. Referring again to FIG. 4C, the production of Molecule 6 by *P. putida* CJ257 was conducted once in a 10 L bioreactor. The DO oscillations were not stable during the DO-stat fed-batch. (1) The feeding solution was replaced by another solution containing 100 g/L glucose and 15 g/L (NH$_4$)$_2$SO$_4$.

Figure 4D:
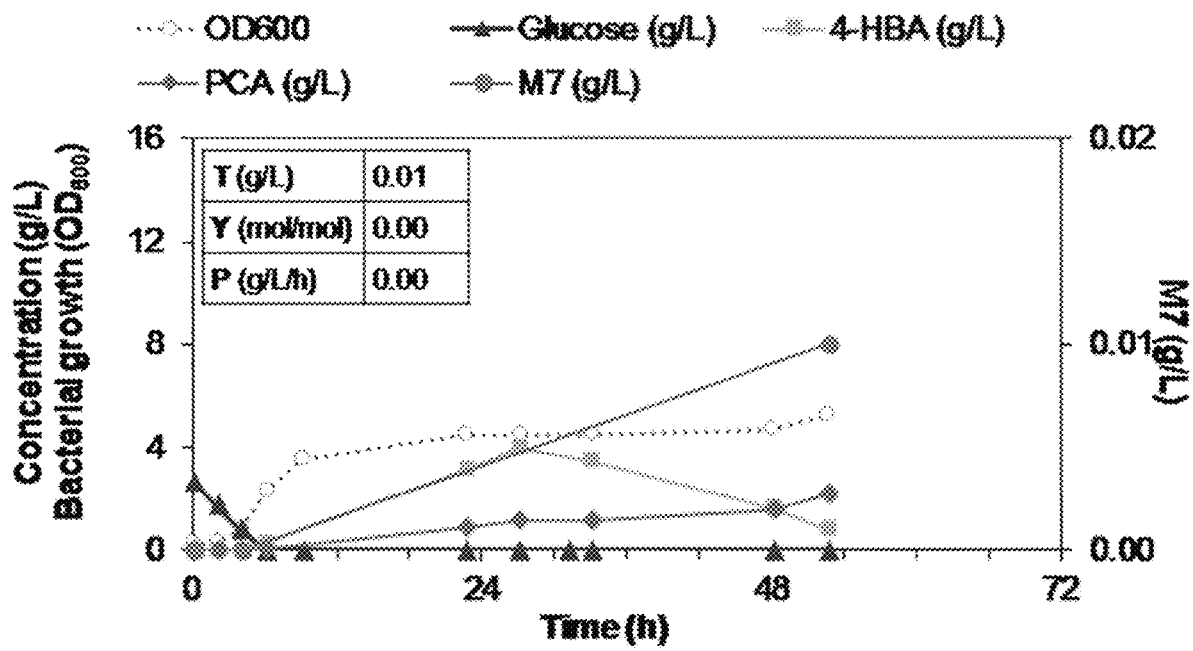
Figure 4D:
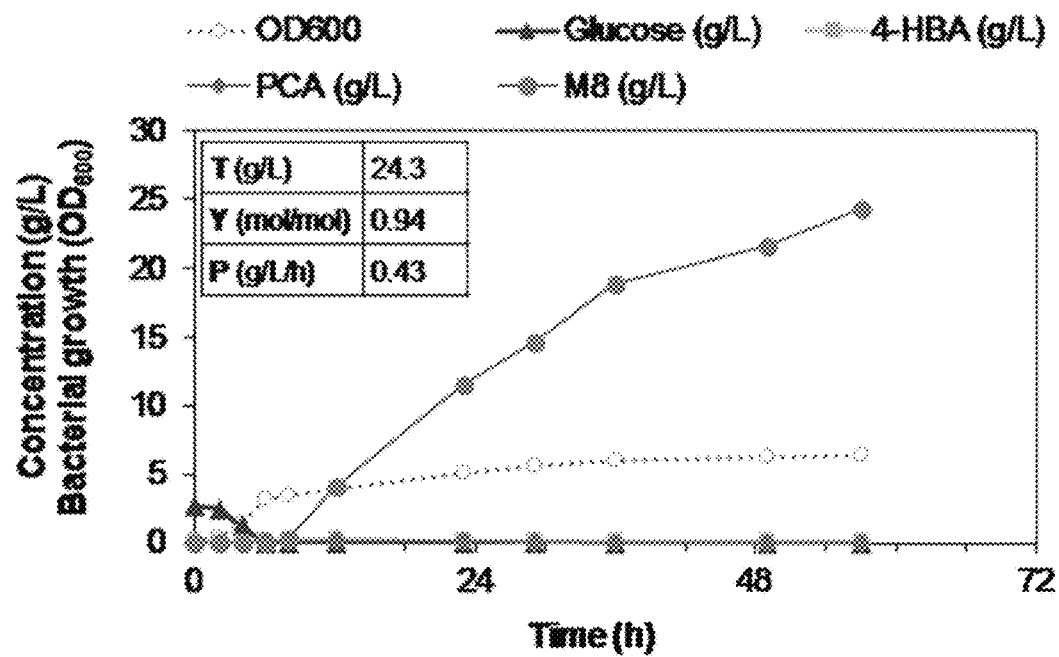

Referring to FIG. 4D, the production of Molecule 7 by *P. putida* CJ259 was conducted twice, in a 10 L bioreactor (with a feeding solution containing 160 g/L of 4-HBA as described in materials and methods—graph shown here), and a 2.5 L bioreactor (with a feeding solution containing 120 g/L of 4-HBA apart from the other components). The DO oscillations were not stable during the DO-stat fed-batch. Intermediates accumulated at similar levels in both cases. Referring again to FIG. 4D, the production of Molecule 8 by *P. putida* CJ261 was conducted once in a 10 L bioreactor.

Figure 4E:
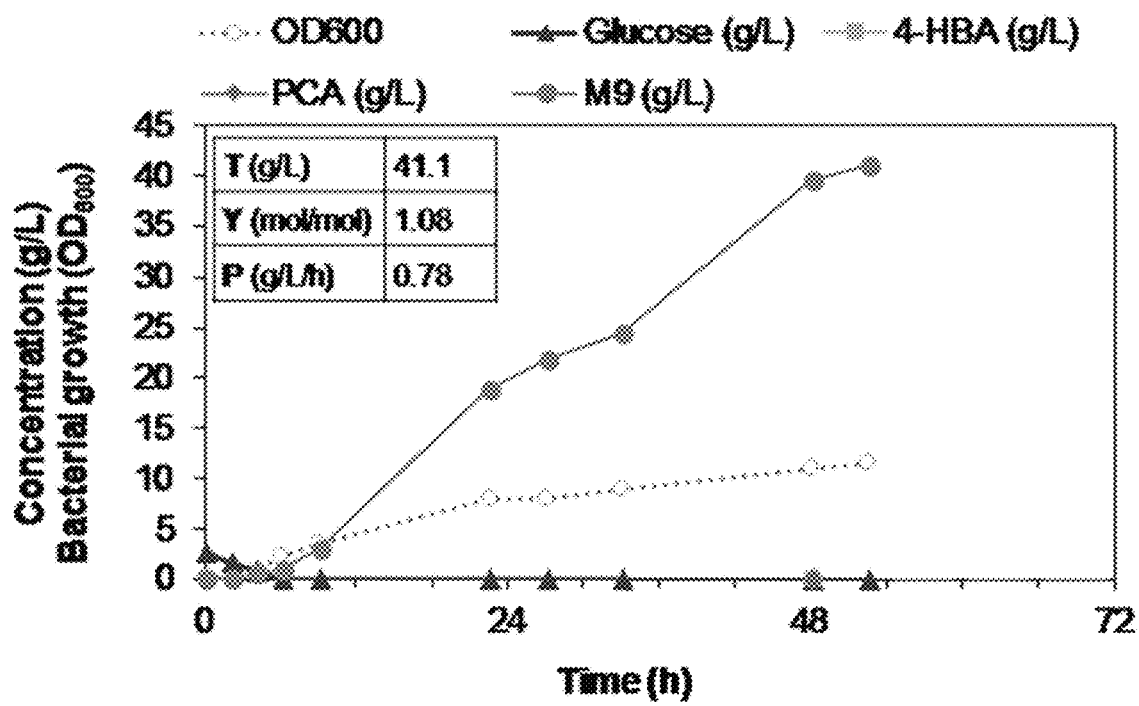
Figure 4E:
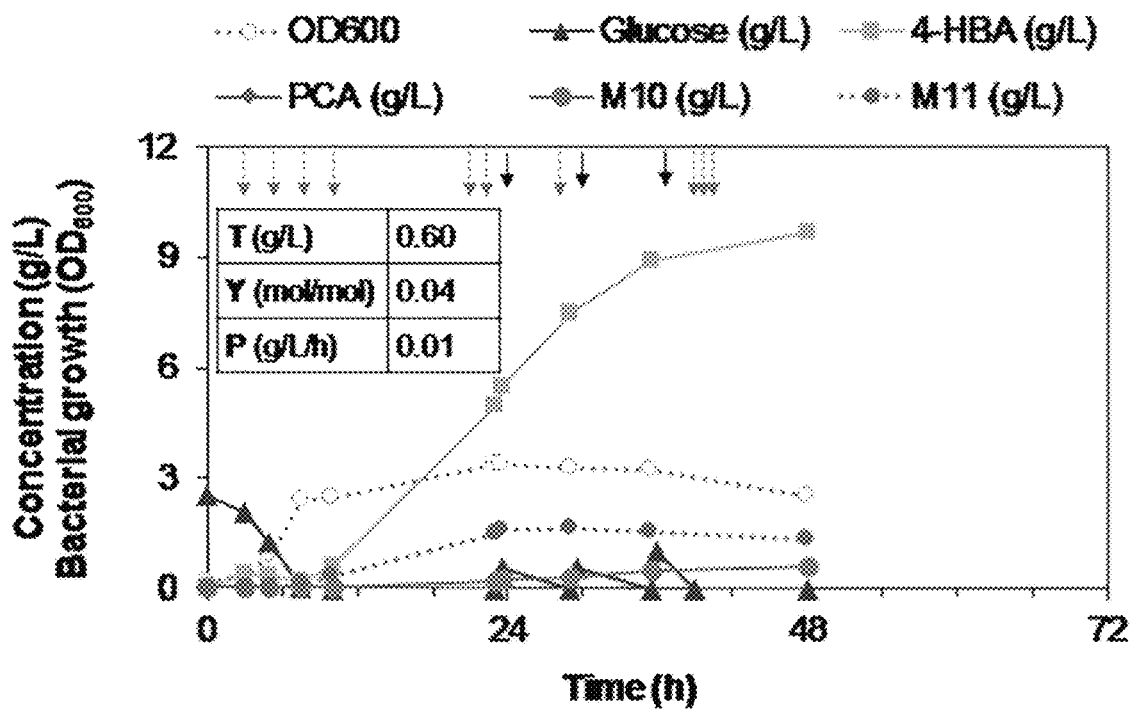

Referring to FIG. 4E, the production of Molecule 9 by *P. putida* CJ263 was conducted twice in 10 L and 2.5 L bioreactors and the results were equivalent. The graph shows the data from the 2.5 L bioreactor. Referring again to FIG. 4E the production of Molecule 10 by *P. putida* CJ265 was conducted twice in 10 L (graph shown here) and 2.5 L bioreactors and the feeding solution contained 30 g/L (NH$_4$)$_2$SO$_4$ instead of 15 g/L. The black arrow indicates the addition of 24 mL pulses of 200 g/L glucose and 30 g/L (NH$_4$)$_2$SO$_4$. Discontinuous, grey arrows indicate pulses of 50 mL with 2 N (NH$_4$)$_2$SO$_4$.

Figure 4F:
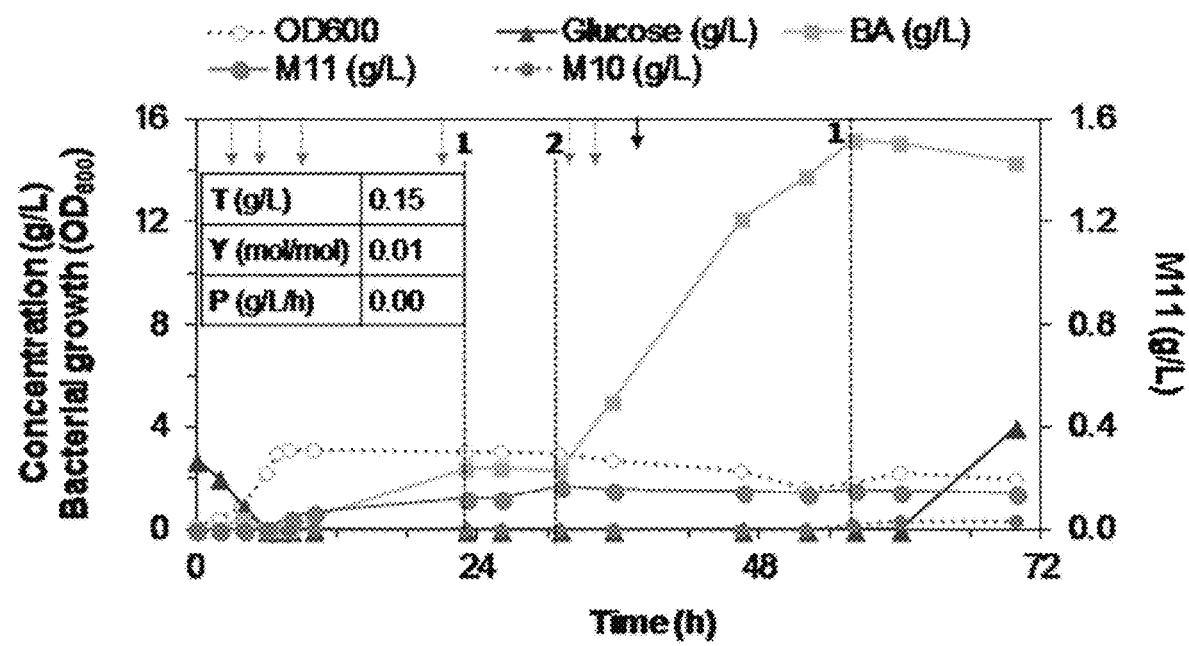
Figure 4F:
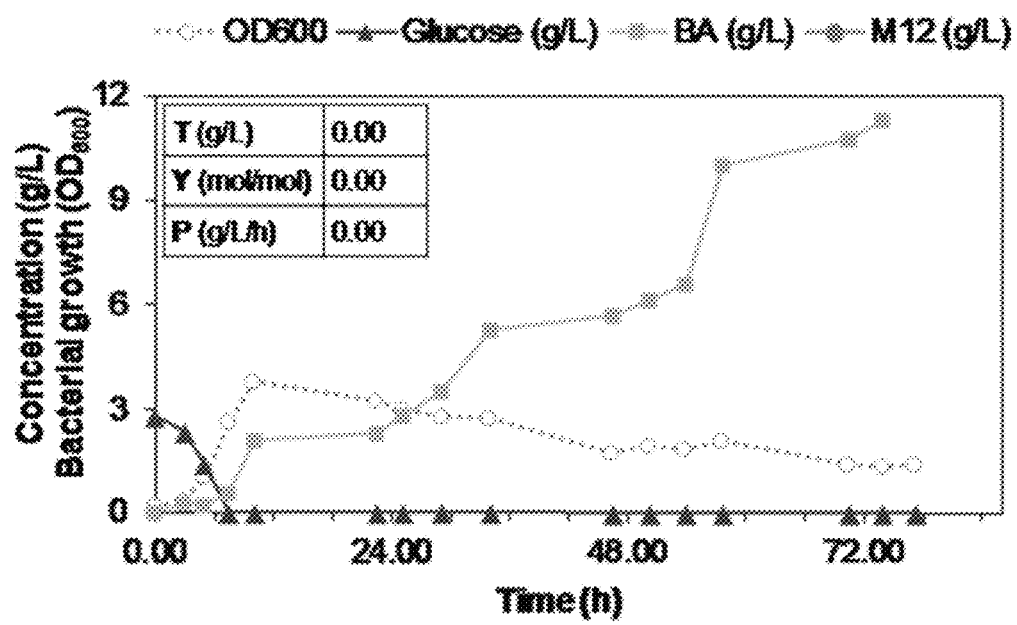

Referring to FIG. 4F, the production of Molecule 11 by *P. putida* CJ146 was conducted twice in 10 L bioreactors. In the first run, Molecule 11 was not detected. The profile from the second run is presented here. The black arrow indicates the addition of 24 mL of a solution containing 100 g/L glucose and 15 g/L (NH$_4$)$_2$SO$_4$. Discontinuous, grey arrows indicate pulses of 8 mL with 0.75 N (NH$_4$)$_2$SO$_4$. The feeding solution contained 15 g/L (NH$_4$)$_2$SO$_4$ in the first run and 30 g/L (NH$_4$)$_2$SO$_4$ in the second run. Referring again to FIG. 4F, the production of Molecule 12 by *P. putida* CJ266 was conducted twice in 10 L and 2.5 L bioreactors (graph from the latter case). Molecule 12 was not detected in any case. DO oscillations were not stable.

Figure 4G:
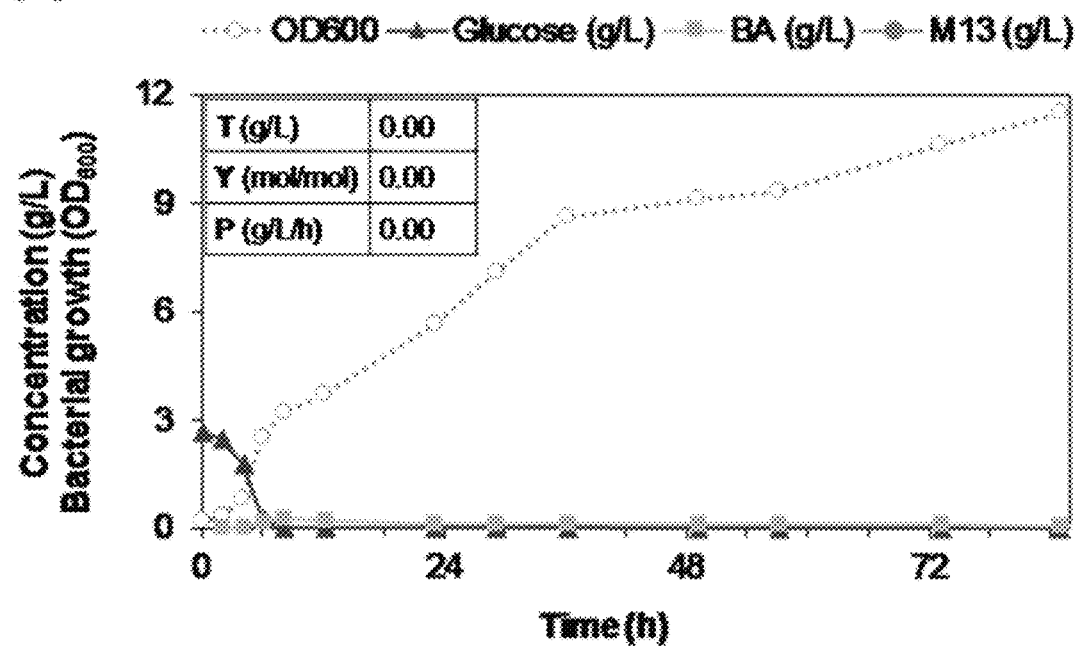
Figure 4G:
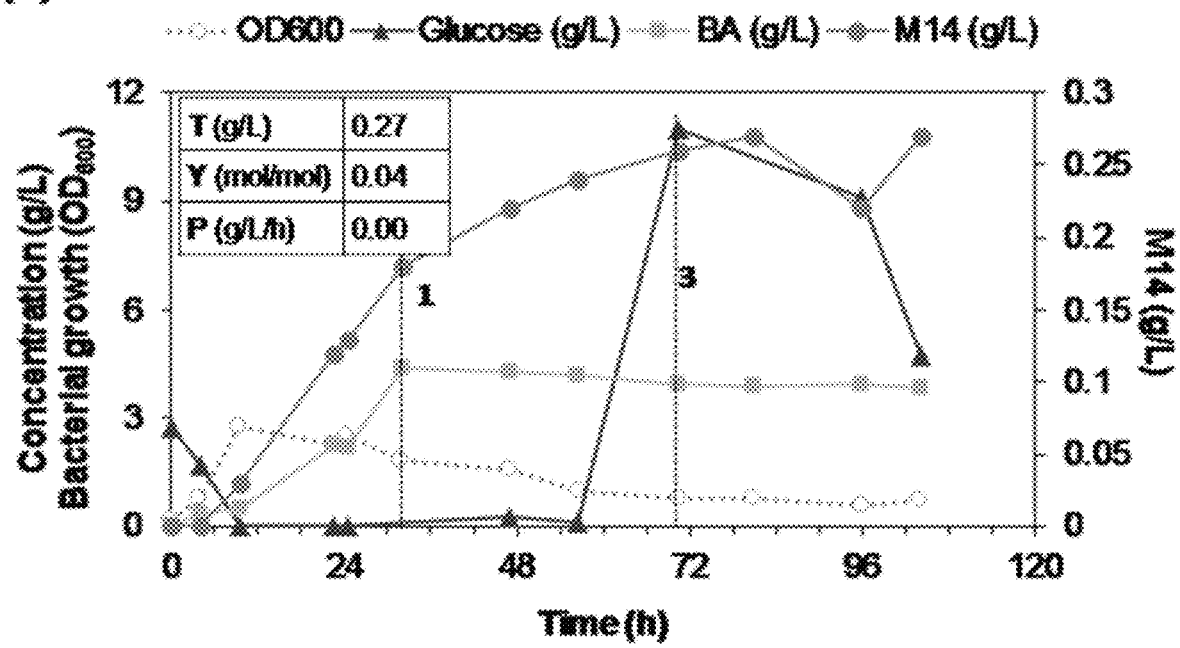

Referring to FIG. 4G, the production of Molecule 13 by *P. putida* CJ267 was conducted twice in 10 L and 2.5 L bioreactors (graph from the former case). Molecule 13 was not detected in any case. DO oscillations were very stable. Referring again to FIG. 4G, the production of Molecule 14 by *P. putida* was conducted 3 times, twice with CJ270 in 10 and 2.5 L bioreactor and one with CJ586 in a 2.5 L bioreactor. Only the latter strain produced the targeted molecule (graph). DO oscillations were not stable in any case. (1) The feeding solution was replaced by another solution containing 100 g/L glucose and 15 g/L (NH$_4$)$_2$SO$_4$, (3) The feeding was stopped since glucose was also accumulating.

Figure 4H:
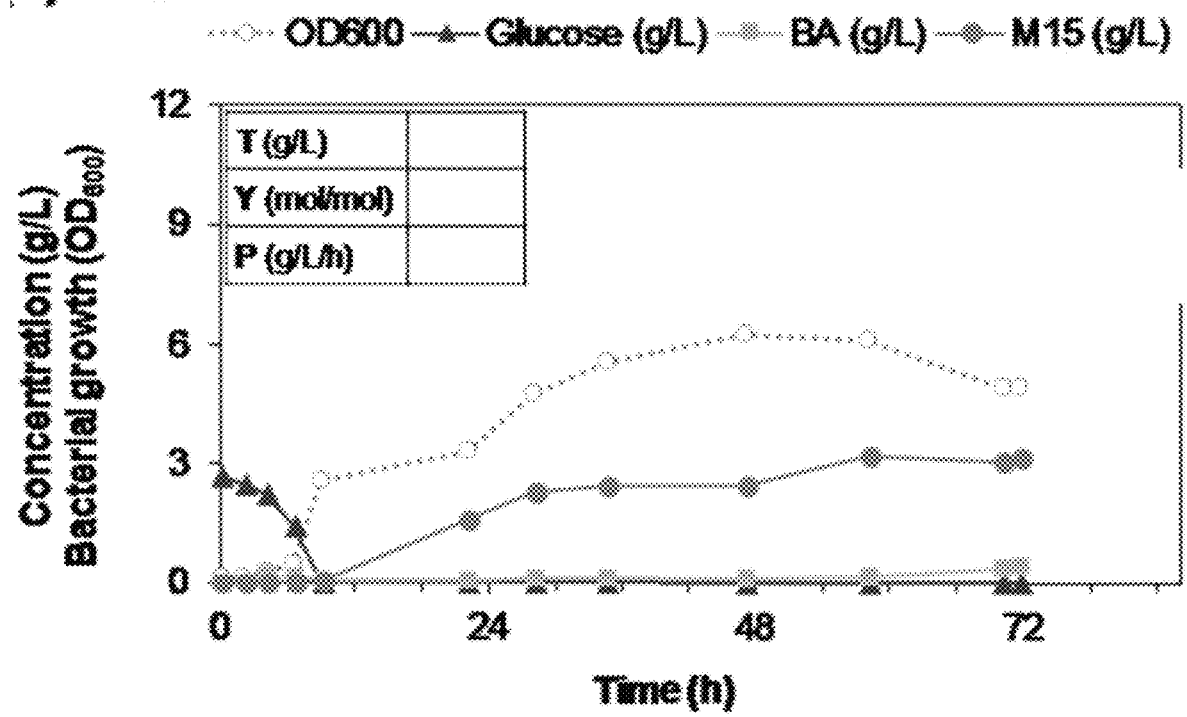

Referring to FIG. 4H, the production of Molecule 15 by *P. putida* CJ268 was conducted three times, twice in 10 L bioreactors and the third one in a 2.5 L bioreactor (graph shown here). The feeding solution contained 15 g/L (NH$_4$)$_2$SO$_4$ in the first run and 30 g/L (NH$_4$)$_2$SO$_4$ in the subsequent runs.

For the production of a subset of molecules from glucose, *P. putida* KT2440 strains producing muconic acid, Molecule 2, 10, and 11 from glucose were revived from glycerol stocks in 1 L baffled flasks containing 200 mL LB and incubated at 30° C. and 220 rpm overnight. Cells were then centrifuged (5,100 rpm, 10 min), resuspended in M9, and inoculated in 2.5 L (Applikon) or 0.5 L (Sartorius) bioreactors at an initial OD of 0.2, containing 1 L or 300 mL of M9, respectively, and a concentration of 15 g/L glucose and 3 g/L (NH$_4$)$_2$SO$_4$. Bioreactors were controlled at pH 7 with 4N NH$_4$OH, at 30° C., and 1 vvm. The initial agitation speed was 350 rpm and DO 100%. Once DO reached 30%, DO was controlled automatically at that level by agitation. For fed-batch cultivations, when the glucose was close to be depleted, continuous or pulsed feeding was applied from a solution containing 500 g/L glucose and 100 g/L (NH$_4$)$_2$SO$_4$, to maintain glucose levels between 0.5 and 15 g/L. Additional details and variations for each strain and bioreactor cultivations are specified in the sections below. Samples were taken periodically to evaluate bacterial growth and analyze glucose and metabolites.

Figure 5A:
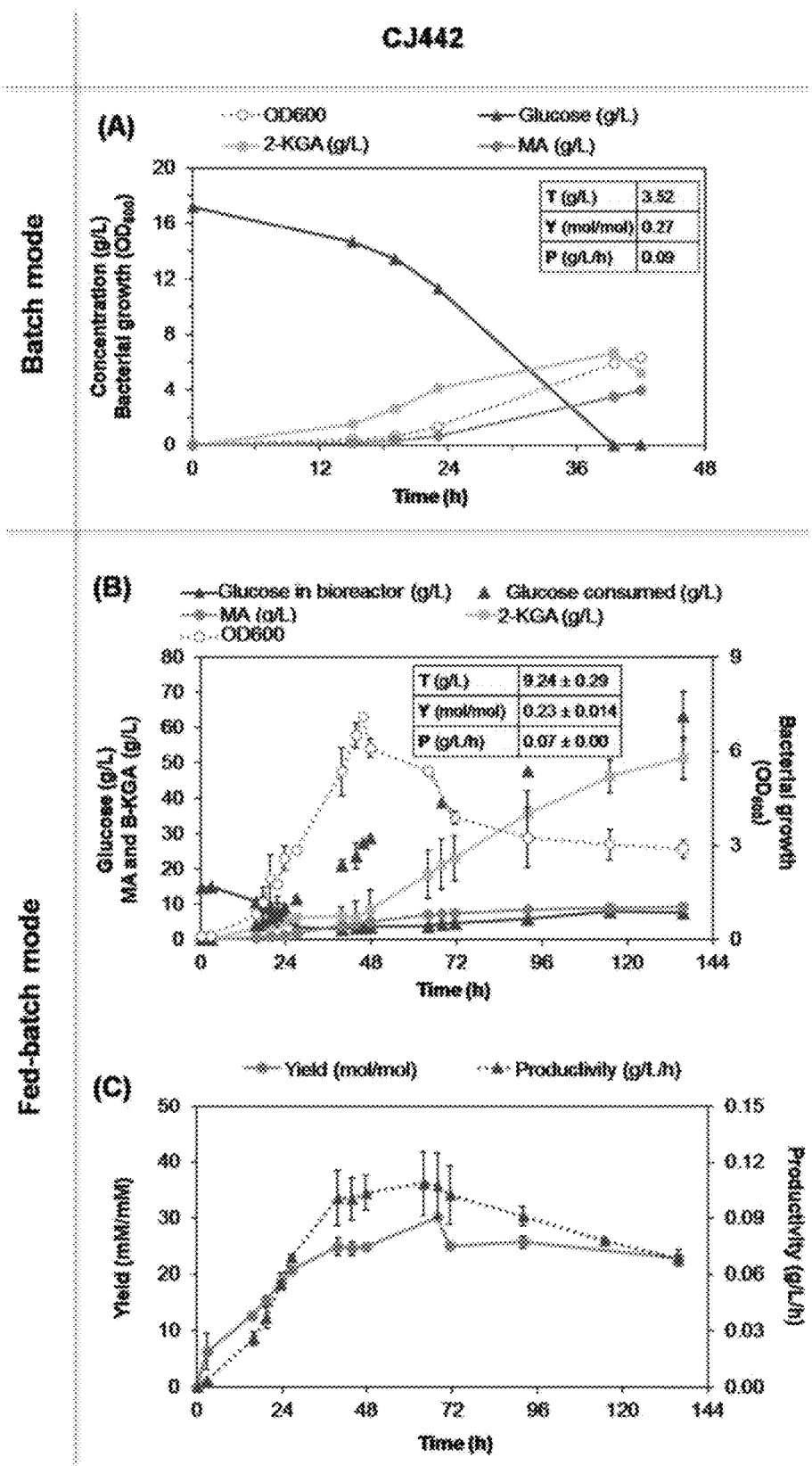
FIGS. 5A and 5B illustrate bioreactor fermentation profiles from engineered *P. putida* strains producing muconic acid from glucose, according to some embodiments of the present disclosure.
Figure 5B:
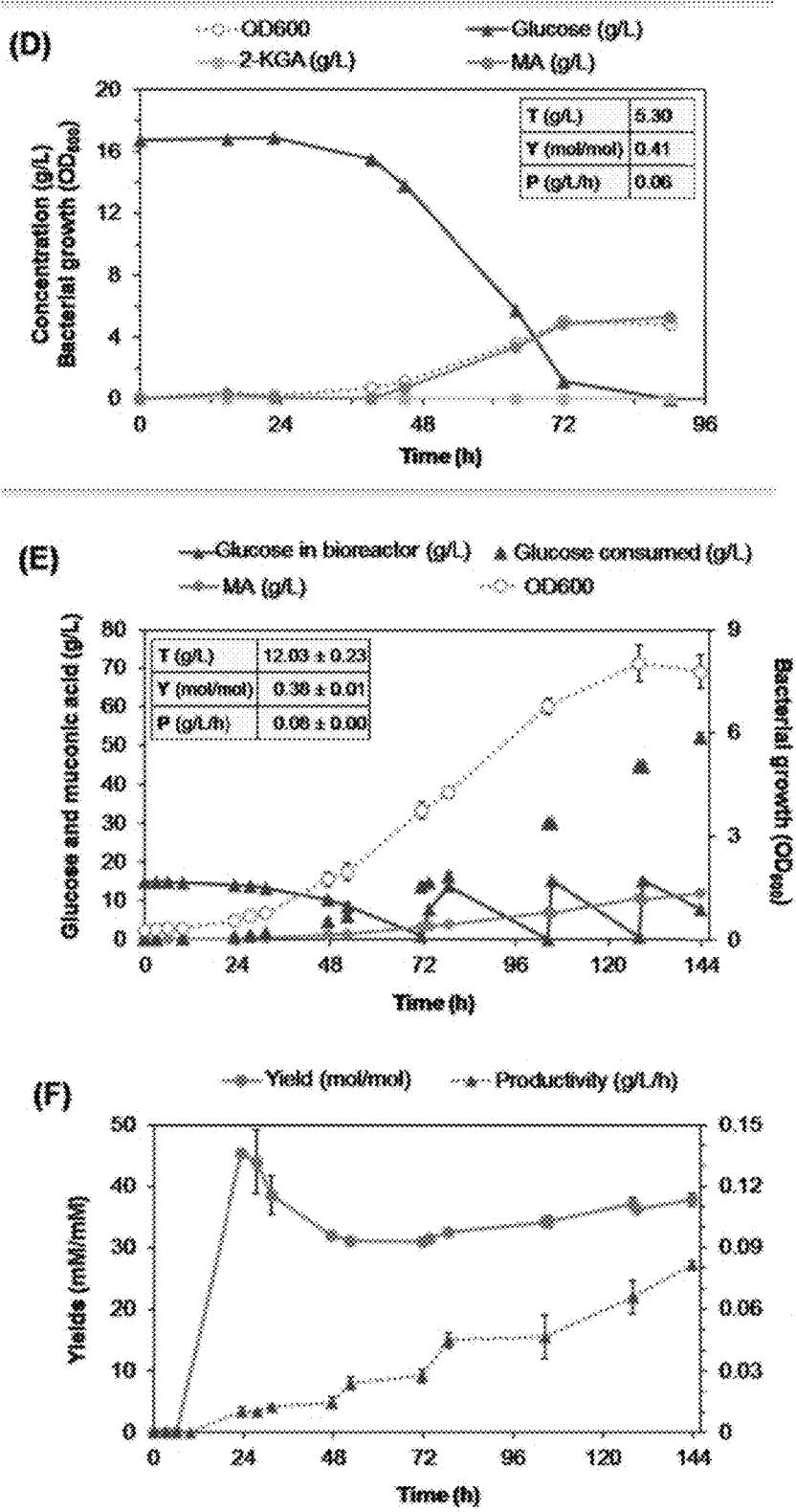

FIGS. 5A and 5B illustrate bioreactor fermentation profiles from engineered *P. putida* strains producing muconic acid from glucose, according to some embodiments of the present disclosure. Referring to FIG. 5A, Panels (A), (B), and (C) illustrate profiles from *P. putida* KT2440-CJ442 cultivations. Referring to FIG. 5B, Panels (D), (E), and (F) illustrate profiles from *P. putida* KT2440-CJ522 cultivations. Panels (A) and (D) in FIGS. 5A and 5B respectively, represent cultivations that were performed in batch mode (singlets), whereas Panels (B) and (D) represent fed-batch mode (duplicates). Muconic acid yield and productivity over time, corresponding to the fed-batch cultivations, are also shown in different graphs (see Panels (C) and (F)). Some specific details are subsequently given. Batch cultivations conducted with both strains and fed-batch cultivations with *P. putida* KT2440-CJ442 were carried out in 2.5 L bioreactors (Applikon). Fed-batch cultivations with *P. putida* KT2440-CJ522 were conducted in 0.5 L BioStat-Q Plus bioreactors (Sartorius Stedim Biotech). Titers (T), yields (Y), and productivity (P) are also highlighted for each strain and feeding mode in the corresponding graph. Titers (g/L) correspond to product concentration at the end of the cultivation time. Yield (mol/mol) is calculated as product mols at the last time point (which is corrected by the dilution factor generated by base and feeding addition) divided by the total mols of substrate utilized (in this case glucose). Productivity (g/L/h) is calculated as product concentration at the last time point divided by the total cultivation time. Data from the fed-batch experiments present the average of a biological replicate. Error bars present the absolute difference between the data obtained from the duplicate at each time point. B-KGA=β-ketogluconic acid; MA=muconic acid; OD600=Bacterial growth by measuring optical density at 600 nm.

Figure 6A:
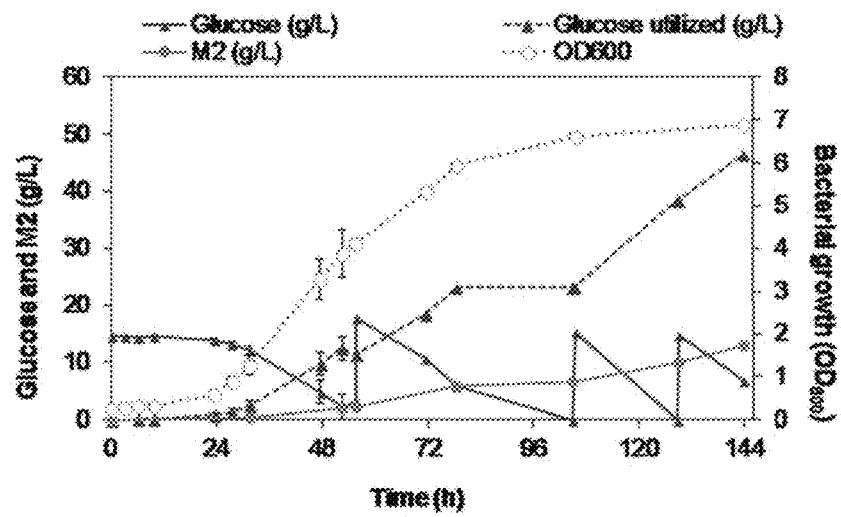
FIGS. 6A and 6B illustrate bioreactor fermentation profiles from engineered *P. putida* strains producing (A) Molecule 2, (B) Molecule 10, and (C) Molecule 11 from glucose, according to some embodiments of the present disclosure.
Figure 6A:
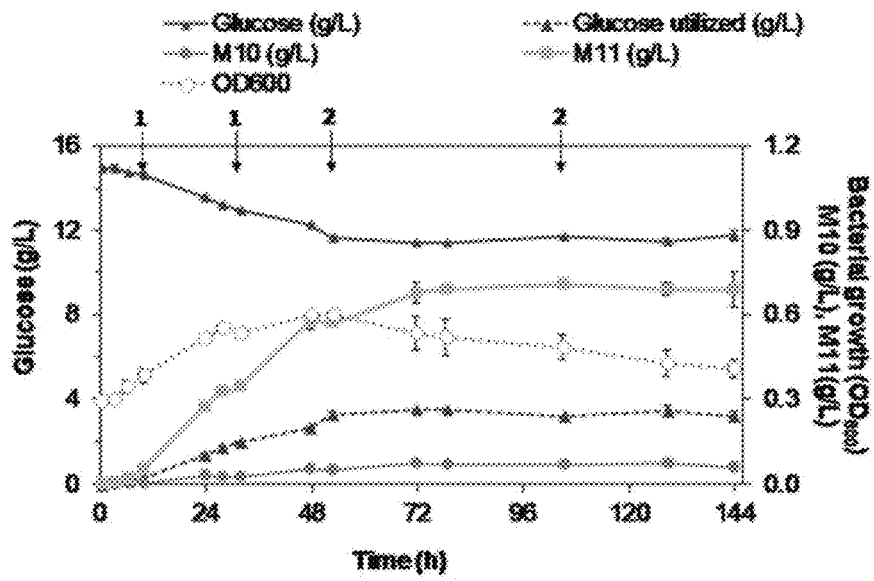
Figure 6B:
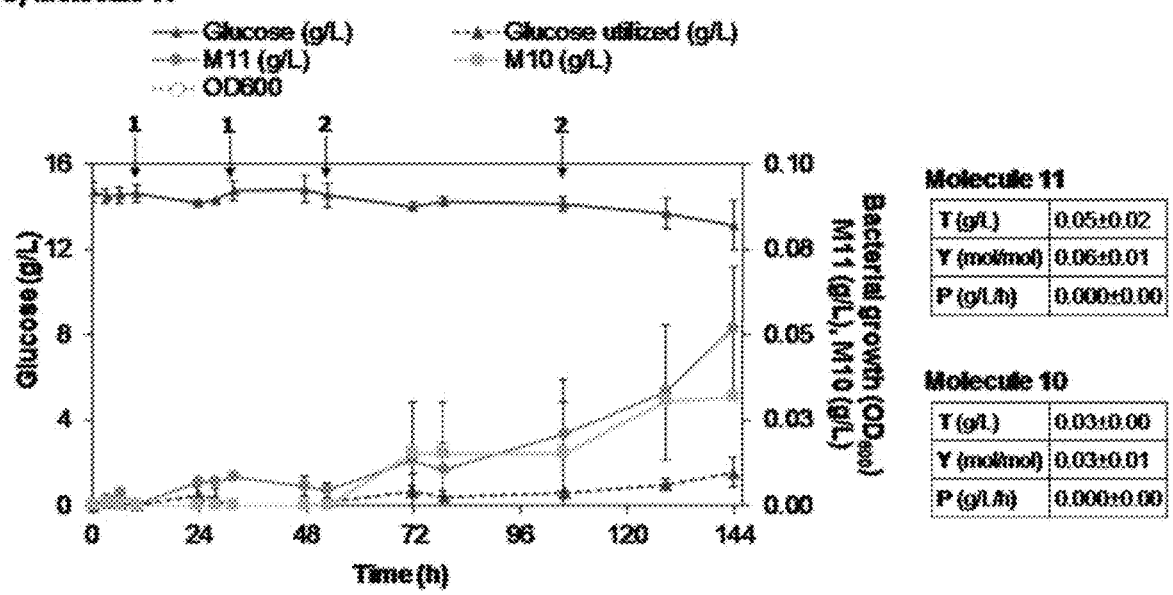

FIGS. 6A and 6B illustrate bioreactor fermentation profiles from engineered *P. putida* strains producing (Panel A) Molecule 2, (Panel B) Molecule 10, and (Panel C) Molecule 11 from glucose, according to some embodiments of the present disclosure. Cultivations were performed in fed-batch mode and in duplicate. For general details on the bioreactor parameters refer to the corresponding section above. Some specific details are subsequently given. These cultivations were conducted in 0.5 L BioStat-Q Plus bioreactors (Sartorius Stedim Biotech). Titers (T), yields (Y), and productivity (P) are also highlighted for each strain at the right of each graph. Molecule 10 and 11 were found in the cultivations producing either molecule and thus, they are also presented. Titers (g/L) correspond to product concentration at the end of the cultivation time. Yield (mol/mol) is calculated as product mols at the last time point (which is corrected by the dilution factor generated by base and feeding addition) divided by the total mols of substrate utilized (in this case glucose). Productivity (g/L/h) is calculated as product concentration at the last time point divided by the total cultivation time. Data present the average of a biological replicate. Error bars present the absolute difference between the data obtained from the duplicate at each time point. During the production of Molecule 10 and 11, pulses with (1) 3 mL and (2) 6 mL of 2N (NH$_4$)$_2$SO$_4$ were also given. OD600=Bacterial growth by measuring optical density at 600 nm.

Strain construction, Plasmid construction, Primer sequences, Sequence of fragment CJ_aroG-D146N_opt_Pp. Strain construction details are included in Table 4. Plasmid construction details are included in Table 5. Primer sequences and description are included in Table 6. Details of fragment CJ_aroG-D146N_opt_Pp sequence and description can be found in Table 7. Details of strains are included in Table 1. Details of plasmid and construction, including the sequences of primers and synthesized DNAs are included in Table 4 for plasmids and Table 5 for strains and strain construction details. Briefly, *P. putida* (ATCC 47054), was engineered by deleting or replacing regions of the genome using an antibiotic/sucrose method of selection and counter-selection. Genetic cassettes consisting of two ~1 kb fragments of DNA with sequences identical to those 5' and 3' of the location in the genome targeted for deletion (5' and 3' targeting regions), as well as a third fragment between these targeting regions containing genes to be integrated, if applicable, were assembled in suicide vectors pCM433 using NEBuilder® HiFi DNA Assembly Master Mix (New England Biolabs) and transformed into NEB 5-alpha F' Iq Competent *E. coli* (New England Biolabs) according to the manufacturer's instructions. Correct assembly was confirmed by restriction digest and the sequence of clones was confirmed by Sanger sequencing performed by GENEWIZ Inc. These plasmids (provided in Appendix) were electroporated into *P. putida* KT2440 or strains derived thereof and antibiotic selection and sucrose counter-selection to accomplish the genetic deletions or replacements were performed.

Culture growth: Strains confirmed to contain the required gene replacements were then evaluated for production of the targeted molecules in shake-flask experiments. 125 mL baffled shake flasks containing 25 mL modified M9 minimal media (pH 7.2) consisting of 13.56 g/L disodium phosphate, 6 g/L monopotassium phosphate, 1 g/L NaCl, 2 g/L NH$_4$Cl, 2 mM MgSO$_4$, 100 μM CaCl$_2$), and 18 μM FeSO$_4$ supplemented with 20 mM Na benzoate (Sigma-Aldrich) or p-coumaric acid (Sigma-Aldrich) neutralized with NaOH. These flasks were incubated shaking at 225 rpm, 30° C. and fed an additional 10 mM glucose after 24 and 48 hrs.

Metabolite analysis: After 72 hours, the cultures were transferred to 50 mL conical tubes and centrifuged to pellet the cells. The supernatants were filtered through 0.22 μm filters and analyzed for the presence of the targeted compound using a Waters Acquity ultra performance liquid chromatography (UPLC) system coupled to an Acquity tunable UV (TUV) detector and a Waters Micromass Q-Tof Micro™ mass spectrometer (Waters Corp., Milford, Mass.). Samples were injected undiluted at a volume of 20 μL and analytes were separated on an Aminex HPX-87H 9 μm, 7.8 mm i.d.×300 mm column (Bio-Rad Laboratories, Hercules, Calif.) using an isocratic mobile phase of 25 mM formic acid at a flow rate of 0.6 mL min$^{-1}$ and a column temperature of 55° C. Metabolites were monitored post-column by 254 nm TUV and mass spectrometry (MS) in series. Positive- and negative-ion electrospray (ESI)-MS and tandem mass spectrometry (MS/MS) in centroid data collection mode was performed. For both ion modes, the nebulization gas was set to 550 L h$^{-1}$ at a temperature of 250° C., the cone gas was set to 10 L h$^{-1}$ and the source temperature was set to 110° C. For negative-ion mode, the capillary and cone voltages were set to 2650 V and 25 V, respectively and for positiveion mode the capillary voltage was 3000 V and the cone voltage was 35 V. For MS experiments, data was collected between m/z 20-500 with collision energy of 8 eV and an acquisition rate of 0.4 sec spectrum$^{-1}$. MS/MS experiments were performed by increasing the collision energy to 15-35 eV, specific to each analyte.

Metabolic modeling: A core-carbon metabolic model of *P. putida* KT2440 was constructed by adapting a model of similar scope from *E. coli* metabolism, including a lumped reaction for biomass synthesis adapted from that of *E. coli*. Additional reactions from the Entner-Doudoroff pathway, peripheral glucose uptake, the shikimate pathway, and muconic acid synthesis were added to the model using stoichiometry taken from the BIGG database and MetaCyc. In total, the model represents 62 metabolites and 75 reactions. Model simulations were performed using the Python package cobrapy. The maximum yield for muconic acid from glucose was calculated using the metabolic model, assuming that the model had to produce all necessary cofactors while setting the ATP maintenance requirement to zero. Knockout suggestions to improve muconic acid yields from glucose were generated using the technique of constrained minimum cut sets. The required input elementary flux vectors were enumerated using the efmtool software package, while the cut sets themselves were calculated using the mhsCalculator package. Cut sets ensured that reaction deletions maintained a specific growth rate of at least 0.15 hr$^{-1}$ and a muconic acid yield greater than 25% (mol/mol) from glucose, while elementary flux vectors with a muconic acid yield of less than 25% were forced to be removed.

Bioreactor Experimental Results: To produce the fifteen different molecules from aromatic compounds, the corresponding engineered *P. putida* KT2440 strains were revived from glycerol stocks in 1 L baffled shake flasks containing 200 mL LB and incubated at 30° C. at 225 rpm for 14 h. Then, the cells were centrifuged at 5,100 rpm for 10 minutes and resuspended in 30 mL of modified M9 (M9) minimal medium. M9 medium consisted of 13.56 g/L Na$_2$HPO$_4$, 6 g/L KH$_2$PO$_4$, 1 g/L NaCl, 2.25 g/L (NH$_4$)$_2$SO$_4$, 2 mM MgSO$_4$, 100 µM CaCl$_2$), and 18 µM FeSO$_4$. Cells were then inoculated in a 10-L New Brunswick BioFlo/CelliGen 310 bioreactor (Eppendorf) at an initial OD600 of 0.2. The bioreactor contained 8 L of M9 media with 15 mM of glucose. The pH was maintained at 7 with 4 N NaOH and the temperature was controlled at 30° C. Air was sparged at a rate of 8 L min$^{-1}$ (1 vvm, volume of air per reactor volume per minute) and the agitation was gradually increased from 350 to 550 rpm to maintain an average dissolved oxygen (DO) level of ~50%. After 4 h, 2 mM sodium 4-hydroxybenzoate (for molecules 1 to 10) or 2 mM sodium benzoate (for molecules 11 to 15) were added to the bioreactors. When the glucose level was close to depletion at ~6-7 h, as indicated by a rapid increase in DO level, automated DO-stat feeding control was initiated. The feeding solution (2 L) was composed of either 160 g/L sodium 4-hydroxybenzoate (for the production of molecules 1 to 10) or 120 g/L sodium benzoate (for molecules 11 to 15) with 100 g/L glucose, 15 g/L (NH$_4$)$_2$SO$_4$, and 6 mL of Antifoam 204 (Sigma-Aldrich). The feeding solution was pumped for ~45 s intervals when the DO was higher than 75%. The amplitude of the DO oscillations was initially adjusted by agitation speed to reach DO amplitudes ranging from 25-75%. In some cases, when the production of these molecules was not successful in the 10 L bioreactors, cultivations were scaled down to 2.5 L bioreactors (Applikon), starting with 1 L media and maintaining the same parameters as described above. Additional details and variations for each strain and bioreactor cultivations are specified below. Samples were taken periodically to evaluate bacterial growth and analyze different substrates and metabolites. At the end of the cultivations—time at which the cells did not origin any DO change after the addition of glucose or the feeding solution was depleted—the bioreactor broths were harvested and cells were removed by centrifugation at 8,000 rpm during 10 min.

Strain Construction

*P. putida* KT2440 (ATCC 47054) was used as the host for strain engineering. Gene replacements were made using selection on kanamycin (50 µg/mL) and counter-selection with sacB on YT media (10 g/L yeast extract, 20 g/L tryptone, and 36.67 g/L agar) containing 25% sucrose. *P. putida* KT2440 was made competent for transformation by electroporation by inoculating *P. putida* from a glycerol stock and incubated at 30° C., shaking at 225 rpm overnight. Two washes in 300 mM sucrose were performed by centrifuging the cell culture and resuspending in the half the initial culture volume. After the second wash, the remaining sucrose supernatant was removed and the pellet was resuspended in 1/100th of the original culture volume with 300 mM sucrose. Cells were then stored at −80° C. after flash freezing with liquid nitrogen or immediately transformed by electroporation.

For transformation, 200 ng-500 ng of plasmid DNA was added to 60 µL of the electrocompetent cells, transferred to a 0.1 cm electroporation cuvette, and electroporated at 1.6 kV, 25 µF, 200 ohms. 800 µL SOC outgrowth medium (New England Biolabs) was added to the cells immediately after electroporation and the resuspended cells were transferred to a microcentrifuge tube and incubated with shaking 225 rpm at 30° C., for two hours.

The entire recovered transformation was plated on an LB agar plate containing 50 µg/mL kanamycin and incubated at 30° C. overnight or until colonies form, up to 48 hours. Transformants were then streaked for isolation on LB agar with kanamycin (50 µg/mL) antibiotic selection and incubated at 30° C. overnight. For sucrose counter-selection, isolates were streaked for single colonies on YT plates with 25% sucrose and incubated at 30° C. overnight or until colonies formed. Colony PCR to determine correct gene deletion or replacement was performed on colonies from the second YT+25% sucrose plate, with primers amplifying the targeted locus outside the homology arms using MyTaq Red Mix (Bioline). These colonies were also plated on LB agar and LB with 50 µg/mL kanamycin to determine whether the analyzed clones retained kanamycin resistance, indicating the remaining presence of the targeting construct. Table 2 lists some of the strains used and/or created in the present disclosure.

TABLE 2

| Strain | Genotype |
| --- | --- |
| CJ072 | *P. putida* KT2440 ΔpcaHG |
| CJ184 | *P. putida* KT2440 ΔcatRBCA::Ptac:catA ΔpcaHG::Ptac:aroY:ecdBD |
| CJ442 | *P. putida* KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 |

TABLE 2-continued

| Strain | Genotype |
|---|---|
| CJ522 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd |
| RJ17A | CJ184 pCatM_lib |
| GB038 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 Δgcd Evolved population |
| GB045 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 Δgcd isolated clone #80 from GB038 |
| GB052 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 Δgcd Evolved population pBTL2-catM-gfp |
| GB062 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 Δgcd ΔhexR |
| GB032 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgl-2 Δgcd ΔgltR1 |
| GB099 | P. putida KT2440 ΔcatRBCA::Ptac:catA ΔpcaHG::Ptac:aroY:ecdB:asbF Δpyk,4::aroG-D146N:aroY:ecdB:asbF ΔpykF Δppc Δpgi-1 Δpgi-2 Δgcd ΔhexR ΔgltR1 |
| GB205 | GB052 Clone A8, plasmid-cured |
| GB206 | GB052 Clone A1, plasmid-cured |
| GB207 | GB052 Clone B9, plasmid-cured |
| GB209 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd ΔhexR ΔgacS |
| GB210 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd ΔgacS |
| GB241 | CJ522 P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpsi-2 Δgcd Δgnd |
| GB270 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd ΔhexR Δgnd |
| GB271 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd ΔhexR Δgnd ΔgacS |

Laboratory Evolution

Strains subjected to evolution were split into 4 lineages. Serial passaging of 4 lineages was performed in modified M9 minimal medium as described above with 30 mM as a sole carbon source and incubation at 30° C. with shaking at 225 rpm. 1% (vol/vol) of the culture was inoculated into fresh medium after overnight cultivation or until growth was observed if growth was not observed after overnight cultivation. $OD_{600}$ was measured at each passage to record the number of generations calculated as Generations=ln (ODfinal/ODinitial)/ln(2). Strains were preserved periodically as glycerol stocks at −80° C.

Genome Resequencing Library Preparation

Genomic DNA for genome resequencing was isolated from LB broth overnight cultures using the ZR Fungal/Bacterial DNA miniprep kit (Zymo Research). Quality of genomic DNA was analyzed by gel electrophoresis. An Illumina Nextera XT library (Illumina, San Diego, Calif.) was prepared as described in the manufacture's protocols stopping after library validation. Briefly, the sample was fragmented, barcodes were appended, and sample was amplified for 12 cycles. The library was then cleaned using AMPure XP beads (Beckman Coulter). The final library was validated on an Agilent Bioanalyzer (Agilent USA) using a DNA7500 chip and concentration was determined on a Qubit (Life Technologies) with the broad range double stranded DNA assay (Life Technologies). The library was prepared for sequencing following the manufacturer recommended protocols. The library was denatured with 0.2 N sodium hydroxide and then diluted to the final sequencing concentration (20 pM). The library was loaded into the sequencing cassette (v3) and a paired end (2×301) run was completed on an Illumina MiSeq Instrument Comparison of Parent and Evolved Isolate Genome Sequences All steps were performed using the Geneious software package. Fastq data files from paired-end MiSeq runs were imported into the software package. Reads were trimmed and filtered to remove poor quality regions and adapter sequences, followed by pairing of filtered reads—unpaired reads were discarded. A reference genome, based on the recent publicly available re-sequenced P. putida KT2440 genome (accession #NZ_LT799039), containing the known genome modifications in CJ522 was constructed in Geneious. Reads for each strain were mapped to this reference sequence. Using the Find Variations/SNPs tool built into Geneious, all mutations relative to the reference genome within the following cut-off values were identified. Cut-off was set to filter out SNPs with minimum coverage lower than 5, minimum variant frequency less than 0.65, and strand-bias was manually examined to confirm that identified SNPs were not sequencing artifacts. All mutations found in both the parent strain and the evolved strains relative to the reference genome were filtered out, and the resulting mutations unique to each evolved isolate were further analyzed for potential impact on a case-by-case basis.

Biosensor Development

The native catM gene with the catM/catB intergenic region (PcatB) and two internal restriction sites (ClaI and EcoRI) in catM removed was synthesized (GENEWIZ, Inc.). The catM-PcatB-sfgfp cassette with superfolder green fluorescent protein (sfGFP) was inserted in a broad host range vector, pBTL-2, (Addgene #22806) between tonB and soxR transcription terminators using NEBuilder HiFi Assembly kit (New England Biolabs), generating the pCatM plasmid. The native promoter PcatB was diversified by overlap oligonucleotide extension method using oligonucleotides with wobble nucleotides (Eurofins Genomics). The diversified PcatB, catM and sfgfp genes were PCR assembled first, and then the fragments were seamlessly joined to the pBTL-2 vector between the tonB and soxR terminators using NEBuilder HiFi Assembly kit to give pCatM_lib.

Biosensor Characterization

Electrocompetent cells of strains CJ184 and CJ072 (Table 2) were prepared and transformed with the pCatM plasmid. Following recovery, transformants were plated on LB-Kan50 agar. Colonies were isolated and preserved at −80° C. after overnight cultivation in LB-Kan50 media at 30° C. Multiple transformations of the pCatM_lib were performed to assure that the number of transformants was equivalent to the theoretical library diversity. The pCatM_lib transformed in CJ184 strain was referred RJ17A. The cells were scraped from the plates using LB-Kan50 and preserved as glycerol stocks at −80° C.

Appropriate dilutions of the cell slurry were also used for LB-Kan50 agar plates supplemented with 10 mM protocatechuate (PCA) or benzoate or as an inoculum for LB-Kan50 liquid media. In liquid cultures, the starting OD at 600 nM wavelength (OD600) of 6 mL culture was kept around 0.05 and after four hours of vigorous shaking at 30° C., when the OD600 reached around 0.6, split equally into three tubes, where the second and third tubes were spiked with 10 mM PCA or benzoate. The plates and culture tubes were incubated overnight at 30° C. with liquid cultures kept under vigorous shaking. The colonies on the plate and liquid cultures were analyzed as described below.

Fluorescence Activated Cell Sorting of Muconate-Producing Cells

The LB-Kan50 agar plates were illuminated using an Illumatool Lighting System (LightTools Research) equipped with a 488 nm excitation filter and photographed using an iPhone 6 camera through a colored glass filter (515 nm; LightTools Research). Overnight liquid cultures were diluted 100-fold in PBS (phosphate buffered saline) buffer before analyzing and sorting using an BD FACSAria III (BD Biosciences) flow cytometer.

Fluorescence activated cell sorting (FACS) was performed using a BD FACSAria III (BD Biosciences) flow cytometer and sorter. The cultures grown in the absence of any muconate precursor, e.g. PCA or benzoate, were sorted for 'dark' cells (negative sort), while cultures grown in the presence of PCA or benzoate were sorted for 'bright' cells (positive sort). For high throughput screening of the RJ17A library for optimal muconate sensing, three rounds of growth and sorting (negative-positive-positive or positive-negative-positive) were performed. More specifically, RJ17A was grown in fresh LB-Kan50 up to an OD600 of about 0.6, and induced with 10 mM benzoate or 10 mM PCA. As a control, cultures without any inducers were also grown overnight at 30° C. FACS was performed to collect the bottom 50% (Sort 1A; 800,000 sorted cells) and medium 30% (Sort 1D; 800,000 sorted cells) of uninduced population, while the top 1% and top 5% from the benzoate (Sort 1B; 50,000) and PCA (Sort 1C; 225,000) induced population respectively. While negative selection (Sort 1A and 1D) ensured rejection of constitutively active variants, positive selection (Sort 1B and Sort 1C) ensured selection of the variants with the highest responsivity to benzoate and PCA respectively. In the subsequent round, Sort 1A-D populations were grown overnight, uninduced or with 10 mM benzoate or PCA. A second round of sorting was made complementary to the first round of sorting, wherein a negative sort in the first round was followed by a positive sort and similarly a positive sort in the first round was followed by a negative sort in the second round. Hence, for the Sort 1A population, the top 1% of 10 mM PCA induced culture was collected, for Sort 1B and Sort 1C populations, the bottom 50% of the uninduced population was collected, and for Sort 1D, the top 1% of 10 mM PCA induced population was isolated. The new populations, Sort 2A (20,000 isolated cells), 2B and 2C (200,000 cells each), and 2D (12,000 isolated cells) were once again grown and induced with 1 mM PCA and 1 mM benzoate. In the final FACS round, Sort 2A, 2C, and 2D cell populations grown in the presence of 1 mM PCA were again sorted to isolate the top 1% bright cells from cultures grown in the presence of 1 mM PCA to give Sort 3A, Sort 3C and Sort 3D. Similarly, Sort 3B was collected from Sort 2B cells grown in the presence of 1 mM Benzoate. In each case 20,000 sorted cells were collected in the final round. Cells from Sort 3A-D were plated on LB-Kan50 agar plates, twelve colonies picked from each sorted population and tested for fluorescence response when grown in the presence of muconate or its precursors, such as PCA, benzoate or catechol.

The clones with a high contrast ratio were grown in larger volumes, the plasmid extracted using a commercially available miniprep kit and sequenced. Overnight cultures were then mixed with 20% glycerol (v/v) and stored as glycerol stocks at −80° C. for future use.

A selected sensor plasmid was dubbed pCatM_C2. The CJ184 culture harboring the plasmid was named RJ17O. pCatM_C2 was also transformed in non-producers of muconate, for example in CJ072 that lack the genes for converting PCA into muconate. This negative control strain was named RJ17P. RJ17P was capable of converting benzoate or catechol to muconate as an intermediate though.

RJ17O and RJ17P were grown overnight from glycerol stocks or from a petri dish in LB-Kan50 at 30° C. under vigorous shaking. The overnight seed cultures were diluted 100-fold in fresh media, and grown for approximately 4-5 h to an OD600 of about 0.6. The cultures were then split in 200-400 µL volumes into multiple wells in a deepwell 1 mL polystyrene 96-well block (Nunc) and spiked with muconate precursors (PCA, benzoate and catechol) such that the final concentration ranged from 10 µM to 10 mM. The block was incubated at 30° C. and under vigorous shaking in a deepwell maximizer (Taitec BioShaker MBR-022UP) for 14-16 h. The cultures were diluted 50-fold in PBS and analyzed using an LSR II flow cytometer (BD Biosciences) with standard settings for GFP fluorescence measurement (488 nm excitation and 530/30 nm emission wavelengths). The arithmetic mean of approximately 100,000 cells tightly gated based on forward and side scatter (FSC/SSC) was used as a measured response of the biosensor.

Accumulation of 2-ketogluconate substantially complicates cultivation of *P. putida* on glucose-containing medium. Deletion of glucose dehydrogenase (encoded by gcd) singularly prevents gluconate and 2-ketogluconate accumulation, but introduces a slight growth defect in a wild type background and a dramatic growth defect when strain CJ522 was generated by deleting gcd from engineered strain CJ442 (FIG. 7). We therefore sought to improve the growth of the muconate-producing strain CJ522.

Adaptive Evolution for Improved Cell Growth

Serial passaging was performed to evolve strain CJ522 for enhanced growth on minimal medium with glucose as a sole carbon source (FIG. 7). During the initial passages, the growth defect of the parent strain was obvious as a full 48 hours was required to see visible growth of each of the four lineages undergoing evolution. Adaptive evolution improved the growth of one lineage, which became apparent when visible growth was observed after only overnight cultivation. The resultant lineage, shown as population GB038 in FIG. 7 had been passaged for 45.4 generations before the growth enhancement was observed. Although the population demonstrated enhanced growth, it was necessary to identify whether an individual clone could recapitulate the phenotype.

Figures 7A, 7B:
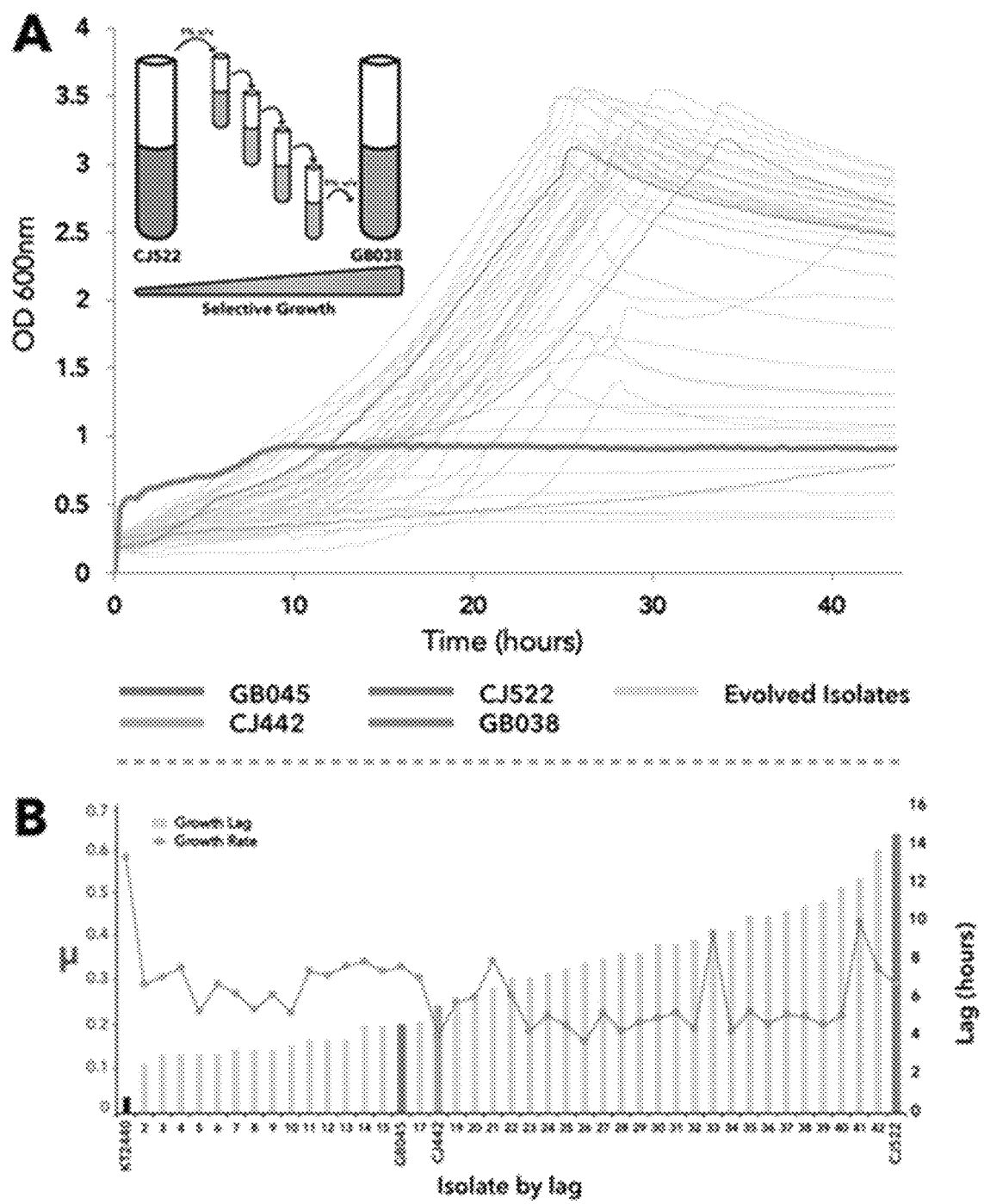
FIGS. 7A and 7B depict the characterization of evolved clones.

Clonal isolates derived from the GB038 population were first screened for growth using a plate reader assay. The parent strains CJ442 and CJ522 were included in the comparison of the heterogeneous evolved population (GB038) and isolated clones (FIG. 7A). The resulting growth phenotypes emphasize the dramatic growth defect caused by gcd deletion in CJ522 compared to the isogenic parent CJ442. Among the evolved isolates, a wide variety of growth phenotypes was observed, with most individual isolates exhibiting enhanced growth and improved growth rates compared to the heterogeneous evolved population GB038 and the unevolved parent strain CJ522 (FIG. 7A). Interestingly, the bulk evolved population GB038 demonstrated marginally improved growth compared to CJ522, while some individual clones demonstrated dramatic growth rate improvements. Many evolved clones had dramatically increased maximum specific growth rates (p), compared to CJ522 in addition to reaching maximum growth faster (FIG. 7B). The growth rate of GB038 was not calculated since this population never entered logarithmic growth during the duration of this experiment. Particularly, isolate GB045 demonstrated dramatically improved growth with a higher $\mu$ than CJ442 and reached that milestone faster than the parent strains (FIG. 7B). This clone GB045 was selected for further characterization.

Figures 8A, 8B:
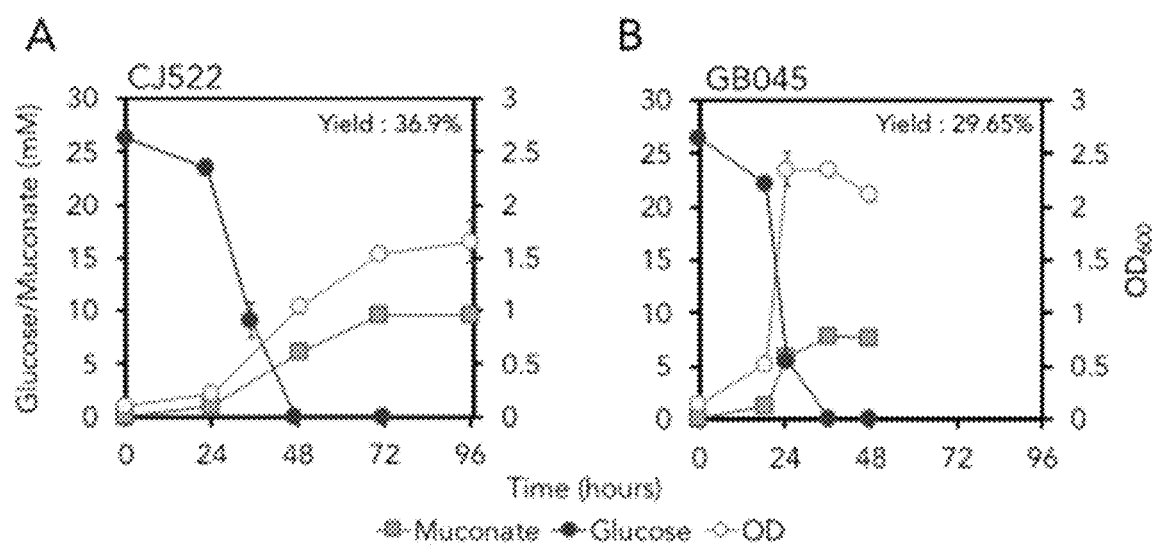
FIGS. 8A and 8B depict shake flask evaluation of muconic acid production of evolved strain GB045 compared to engineered train CJ522.

While adaptive evolution successfully enhanced growth, we ultimately sought to improve muconate productivity as a function of growth. We therefore assayed isolate GB045 for muconate production in a shake flask experiment. GB045 again demonstrated substantially improved growth, reaching its maximum OD600 48 hours faster than the unevolved parent strain CJ522 (FIG. 8). Clearly, evolution for enhanced growth translated to more effective biomass production, as GB045 not only reached maximum OD600 faster, it also reached a higher final OD600. Muconate production of GB045 mirrored strain growth. Strain GB045 reached its maximum muconate titer of 7.9 mM at 36 hours compared to CJ522 which reached its maximum titer of 9.7 mM after 96 hours of cultivation (FIG. 8B). Although GB045 produced muconate faster, CJ522 ultimately produced a higher final titer. These data indicate that although the GB045 demonstrated improved growth and faster muconate production compared to the unevolved parent strain CJ522, the final muconic acid titer was slightly lower in the evolved isolate. The resulting evolved isolate reflected the growth-based selection pressure.

Muconate-Responsive Biosensor Development for Product-Based Selection

A comprehensive solution to the growth defect introduced by the gcd deletion would restore muconate productivity and yields, in addition to growth. We sought to develop a high-throughput method to select on both muconate production and growth. A FACS-based, high-throughput assay was used to isolate evolved clones from population GB038 by selecting on muconate production of individual cells. We first required a functional method to select single cells based on muconate production.

Selection of a Scaffold

Muconate is a key intermediate in the catechol branch of the β-ketoadipate pathway and several organisms have evolved regulators to respond to this key intermediate. A few known transcription factors that respond to muconate are CatR from *Pseudomonas putida* and CatM and BenM in *Acinetobacter* baylyi ADP1. In *Acinetobacter* baylyi ADP1, the dual regulation carried out by LysR-type transcription regulators, BenM and CatM, are both controlled by muconate, while the former also responds to a precursor, benzoate. While previous muconate sensors have been established in *E. coli* and *S. cerevisae* both of them have been developed using BenM, where cross-reactivity with benzoate via a secondary binding site has been characterized.

We chose CatM as a scaffold for building a sensor in *P. putida* KT2440. The catM-catB intergenic region (referred to as PcatB) consists of three CatM binding sites. A synthetic construct was designed consisting of catM and an intact PcatB from *Acinetobacter* baylyi ADP1 controlling expression of a reporter gene, sfgfp, that codes for a superfolder green fluorescent protein (sfGFP). The gene cassette was inserted into a broad host range vector, pBTL-2, generating the pCatM plasmid. The resulting plasmid was tested in the *P. putida* KT2440 strain CJ184, which can convert lignin derived aromatics such as benzoate and protocatechuate efficiently to muconic acid. When this strain was fed benzoate, which can be efficiently converted to muconate, no fluorescent signal was observed above the baseline.

Library Design

The pCatM system was altered to enable muconate-responsive expression of the fluorescent reporter. Directly transferring regulatory sequences (consisting of promoters, operators, and ribosome binding sites) between various species may fail to function as expected in the new host, potentially explaining why no fluorescence was observed upon our initial attempt to deploy CatM in *P. putida*. To overcome this species transfer barrier, we mutated and diversified PcatB ribosome binding site (RBS) as this has been shown to improve sensor dynamic range. Mutations in the operator as well as the −35/−10 sites were pursued to improve interaction of CatM with the operator as well as the RNAP with the promoter. A plasmid library with diversity >65,000 was constructed and transformed into strain CJ184, generating strain RJ17A. After transformation the colonies were scraped and used for fluorescence-activated cell sorting (FACS).

Fluorescence-Activated Cell Sorting of Promoter Library

Figures 9A, 9B:
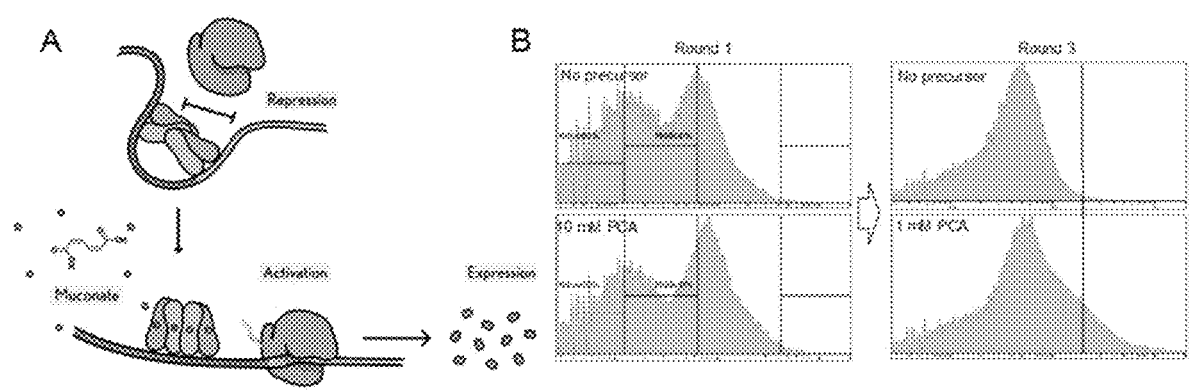
FIGS. 9A and 9B.

Analysis of RJ17A demonstrated two distinct peaks in fluorescence histograms when analyzed by flow cytometry, with and without PCA, which is efficiently metabolized to muconate. We then identified library constituents which generated increased fluorescence in the presence of PCA, and therefore muconate, by sorting for 3 rounds with both positive and negative selection. After selection, enrichment of increased fluorescence in the presence of PCA was observed (FIG. 9B).

From this selected population, we isolated clones with a wide range of background fluorescence and contrast ratios. Several of the clones generating the highest contrast ratio were sequenced and showed a consensus of GTGT for the −35 site, rather than the canonical GTAT. Both of these sequences are expected to bind tighter to CatM than the native sequence TTTA. Mutations in the −10 site were only observed in clones with low background, where the native TAAGGT was exchanged for TACAGT. Using this information, we built the sensor construct pCatM_C2 under the regulation of an optimized promoter (PcatB-opt).

We next characterized pCatM_C2 expressed in strain CJ184, generating strain RJ170. Unlike the previous result with the sensor-reporter under an unoptimized promoter, RJ170, showed a clear dose dependent response with PCA, FACS of GB052

Figures 10A, 10B:
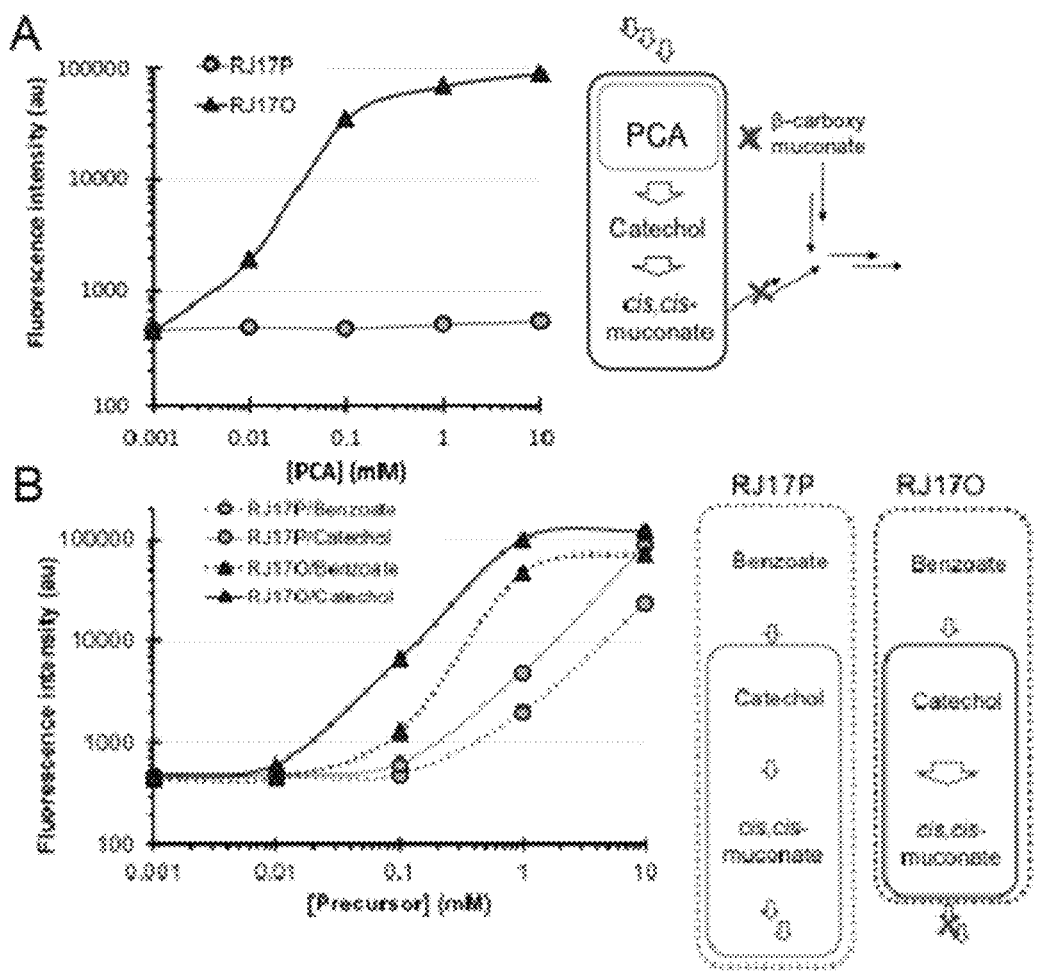
FIGS. 10A and 10B depict dose-response plots of *P. putida* cells harboring an optimized sensor-reporter plasmid pCatM_C2.

The heterogeneous evolved population GB038 was made electrocompetent and was transformed so that the population now carried the functional pCatM_C2 biosensor. Heterogeneity of the transformants was maintained by recovering in liquid selective medium, rather than isolating individual clones on solid medium. The resulting population, now designated GB052, was analyzed for muconate-induced GFP fluorescence by FACS. In order to isolate improved muconate producing clones, we sorted the GB052 library during early log phase (around 8 hours) which should improve the ability to isolate a rare high producer within a population of clones which may produce high titers more slowly, and it should limit cross-talk between cells. Multiple GFP populations were observed, indicating muconate production heterogeneity within the evolved population. To ensure that the sensor was not responsive to PCA rather than muconate, specifically, pCatM_C2 was transformed into a strain incapable of metabolizing PCA, strain CJ072, and no PCA-responsive fluorescence was observed (FIG. 10). Together, these data demonstrate that the optimized construct pCatM_C2 is a sensitive and specific sensor of intracellular muconate in P. putida.

Figure 11:
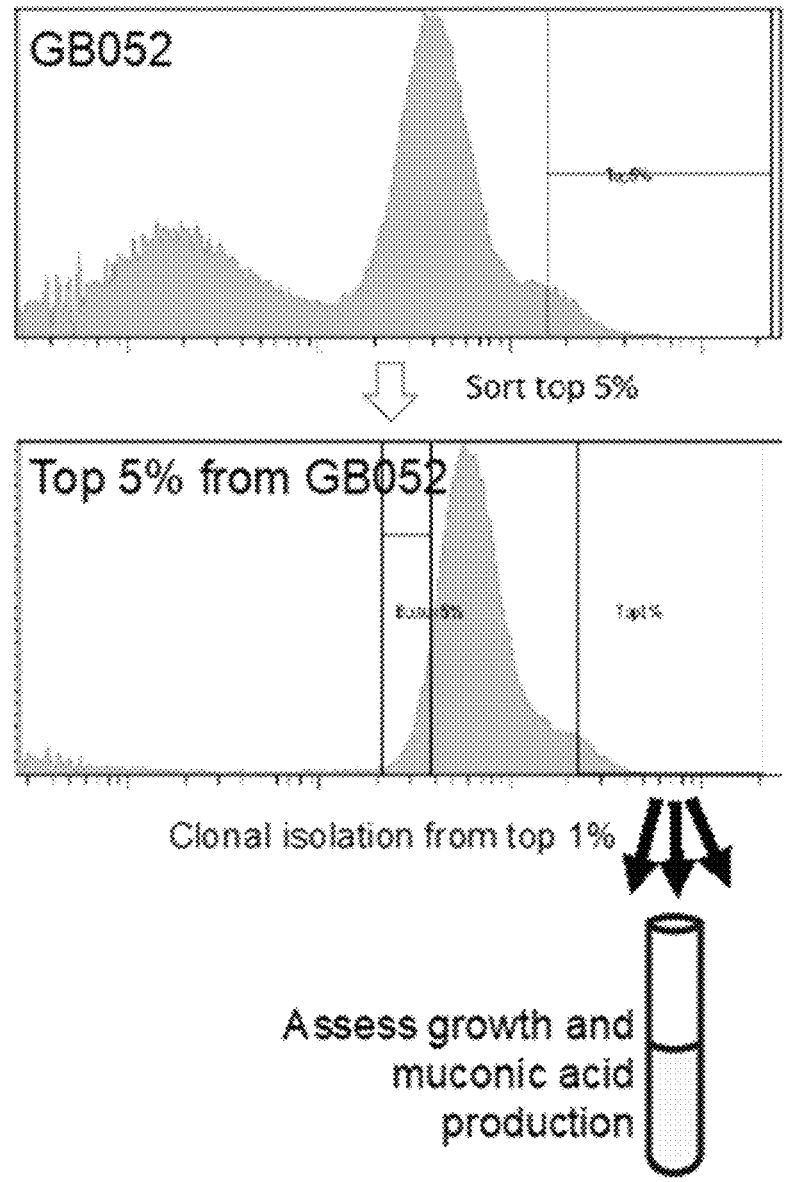
FIG. 11 depicts FACS sorting of evolved population carrying the CatM-based biosensor construct. GFP fluorescence of the unsorted population GB052 is shown in the top panel, with varied GFP populations. The cells emitting the top 5% GFP fluorescence intensity were sorted and re-analyzed (bottom panel). Individual clones were isolated from the top 1% of the sorted population derived from GB052 and were subjected for further characterization.

As some populations exhibited strong GFP fluorescence, we sought to isolate these subpopulations to determine whether the GFP fluorescence reflected improved muconate production. In order to isolate a stable subpopulation with strong GFP signal, FACS sorting on the highest 5% GFP signal was performed, followed by selection on the top 1% of GFP fluorescence (FIG. 11).

Negative selection against the bottom 5% of GFP signal was performed to ensure the isolation of clones with comparatively higher muconic acid production, as predicted by GFP fluorescence. Two lineages were designated from this population: Lineage A and Lineage B. From there, individual clones were isolated by streaking for downstream characterization. Clones GB205 and GB206 were clonal isolates derived from the A lineage, and clone GB207 was isolated from the B lineage.

Shake Flask Characterization of Sorted Clones

Figures 12A, 12B, 12C:
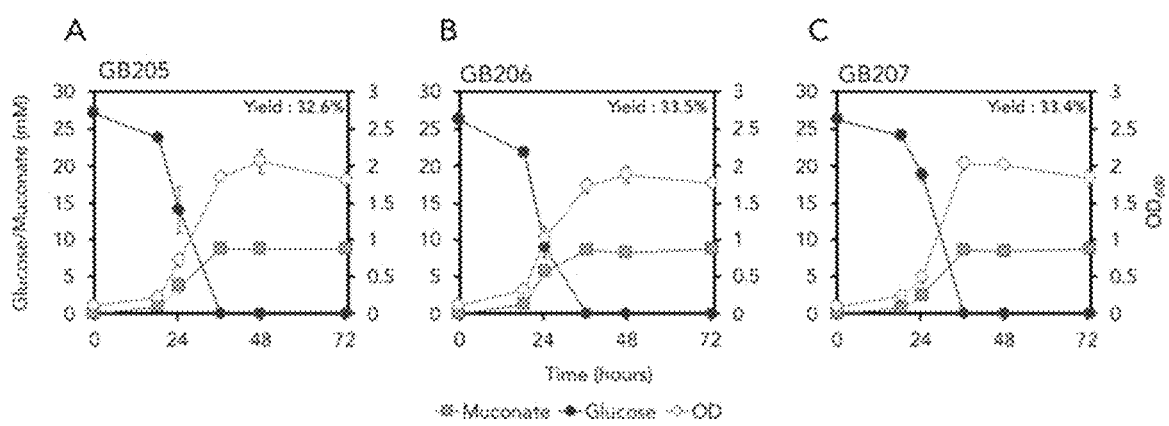
FIGS. 12A, 12B, and 12C depict shake flask evaluation of muconic acid production of evolved, sorted isolates.

After isolating clones emitting strong GFP signal, we next sought to determine whether this elevated GFP signal corresponded with improved muconate production. Since the isolated clones carried the biosensor plasmid, we first cured the sorted clones of the biosensor construct prior to performing a shake flask assay. A shake flask cultivation of three biosensor-selected clones was performed in minimal medium with 25 mM glucose as the sole carbon source. The three isolated clones demonstrated improved growth compared to the unsorted, unevolved parent strain CJ522. Strains GB205, GB206, and GB207 reached maximum muconate titers of 8.8 mM, 8.6 mM, and 8.5 mM, respectively after 36 hours of cultivation (FIG. 12). While they all performed similarly to one another, they consistently reached maximum titers 60 hours faster than the parent strain CJ522, while reaching similar titers and yields as that progenitor strain. These data demonstrate that selection on muconic acid within an evolved population enables the isolation of individual clones with improved muconic acid performance, in addition to improved growth.

Whole Genome Sequencing of Evolved Clones

We sequenced the genome of the evolved isolates in an attempt to identify causal mutations underlying improved performance. Strain GB045 contained a total of four contiguous mutations relative to the parent strain CJ522 (Table 3). Two mutations, a 574 basepair deletion in PP 4373 (fleQ) and a replicative transposon insertion disrupting PP 1650 (gacS), likely disrupt the function of these two global regulators. FleQ is required for flagellar function in many Pseudomonads, including P. putida KT2440 (Blanco-Romero et al., 2018), and is itself downregulated by the GacS/GacA two-component system during stationary phase in many Pseudomonads. Disruption of GacS function was also observed to reduce lag time and improve growth in Pseudomonas sp.

TABLE 3

Mutations identified in evolved isolates

| Gene | Category | Locus | Affected Strains |
| --- | --- | --- | --- |
| lapA | insertion | | GB052-B9 |
| glyA-II | substitution | | GB045 |
| cyoB | substitution | | GB045 |
| edd | substitution | | GB052-A1 |
| gacS | insertion | | GB052-B9, GB052-A1, and GB045 |
| PP_3142:PP_3194 | deletion | 35553032-3675445 | GB045 |
| PP_4031:PP_4058 | deletion | 4542786-4577900 | GB052-B9 |
| fleQ | deletion | | GB045 |

PCL1171, suggesting the gacS disruption plays a role in the improved growth phenotype. The third mutation is a missense mutation in glyA-II (A34T) which encodes a serine hydromethyltransferase and is likely a hitchhiker mutation. Finally, we identified a large deletion in the GB045 genome, spanning a region of 130,000 base pairs (Table 3).

Sequencing of the clones isolated by sorting on muconate production revealed that mutations cluster into the two distinct A and B lineages, and are entirely unrelated to GB045. All strains in the first lineage (lineage A), including isolates GB205 and GB206 contain a characteristic transition mutation in the edd (PP_1010) and gap-1 (PP_1009) promoter region. Normally, transcription of these two operons, as well as the remainder of the Entner-Douderhoff pathway is tightly regulated by the repressor hexR. While the mutation does not appear to be located in either of the two known operators in this region, we used the σ70 promoter prediction software, BPROM, to analyze the sequence for new promoters. The mutation appears to activate a cryptic promoter for the edd operon by generating a new −10 sequence. In addition to the promoter mutation, lineage A also contains a transposon insertion into gacS identical to that observed in GB045, suggesting that the strains are related.

The second lineage comprised of GB207 (lineage B) contains a characteristic ~35 kb deletion. The deleted region includes an operon (PP_4043 to PP_4041) encoding several proteins involved in sugar metabolism: 6-phosphogluconate dehydrogenase (gntZ), glucose 6-phosphate 1-dehydrogenase (zwf-2), and sugar phosphate phosphohydrolase (spp). Lineage B also contains multiple transposn insertions into lapA (PP_0168), a large adhesion protein critical for biofilm formation in P. putida.

Rational Engineering for Enhanced Growth and Muconate Production in *P. putida* KT2440

Sequencing data from sorted clones suggested that glucose metabolism may serve as a logical target for improved strain engineering. When the production of 2-ketogluconate is inhibited, growth of the resulting strains suffers. Without 2-ketogluconate, any allosteric regulation relying on 2-ketogluconate as a ligand might be dysregulated in *P. putida*. 2-Ketogluconate has been reported to serve as the allosteric ligand for the GltR and PtxS regulators. Specifically, GltR has been characterized as an activator in *P. putida* KT2440 of glucose uptake porins and the gtsABCD operon in response to 2-ketogluconate. PtxS also allosterically responds to 2-ketogluconate but controls the expression of a variety of gene targets not directly related to glucose uptake. The transition mutation in the edd promoter in the sorted A lineage would affect the expression of gltR2, as this regulator is expressed in an operon under the control of the edd promoter. *P. putida* KT2440 contains two copies of GltR, with prior reports characterizing GltR2. We sought to delete both GltR copies to assay the effect on cell growth.

We returned to the unevolved parent strain CJ522 as the host for targeted engineering informed by the evolutionary results and prior literature. In CJ522, we generated the deletion of gltR1 but we were not successful in deleting gltR2, indicating that gltR2 is essential in the CJ522 background. In addition to gltR, WGS sequencing of evolved clones revealed mutations in the edd promoter which is transcriptionally regulated by HexR suggesting that avoiding HexR regulation may be advantageous. HexR has been shown to regulate the expression of several of the glucose metabolic genes, including gap1, edd, glk, gltR2, zwf1, pg1, and eda. Since HexR regulates so many of the glucose uptake genes and serves as a repressor, we deleted hexR from strain CJ522 generating strain GB062.

Figures 13A, 13B, 13C, 13D, 13E, 13F, 13G, 13H:
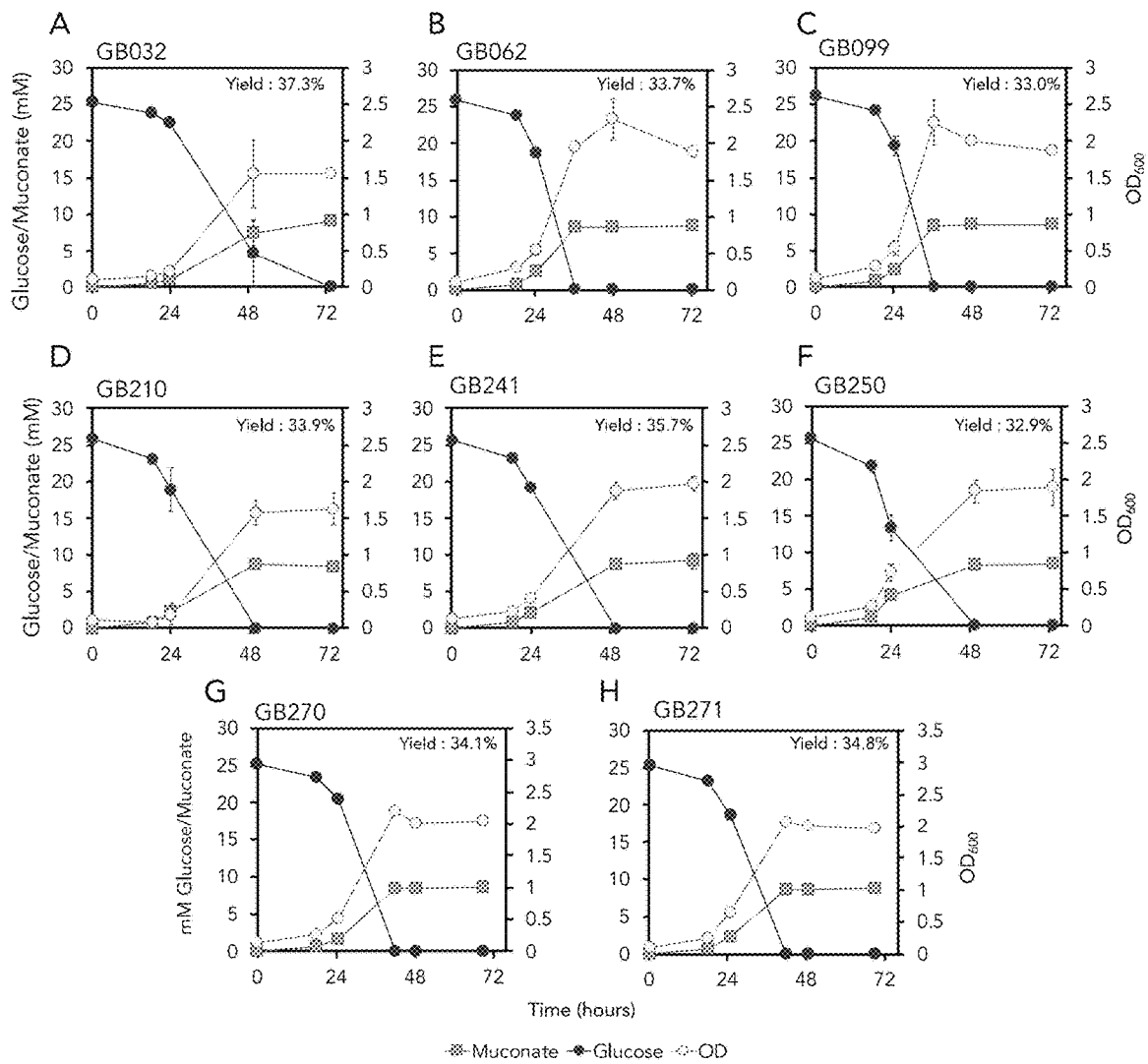
FIGS. 13A through 13H depict shake flask characterization of rationally engineered strains. (A) depicts production performance of GB032 (CJ522 ΔgltR1) (B) depicts GB062 (CJ522 ΔhexR), (C) depicts GB099 (CJ522 ΔgltR1 ΔhexR) (D) depicts GB210 (CJ522 ΔgacS) (E) depicts GB241 (ΔgntZ), (F) depicts GB250 (CJ522 ΔgacS ΔgntZ) (G) depicts GB270 (GB062 ΔgntZ) (H) depicts GB271 (GB062 ΔgacS ΔgntZ). Strains were cultivated in M9 minimal medium containing 25 mM glucose. Culture growth was evaluated by measuring the OD600. Glucose and muconic acid concentrations were analyzed by HPLC. Each value represents the average of biological triplicates, with error bars representing the standard deviation of the replicates.

In shake flask experiments, it was clear that GB062 could more effectively grow on glucose, as it enters stationary phase nearly 70 hours sooner than the parent strain CJ522 and reaches a similar titer and yield, improving the productivity without any reduction in yield (FIG. 13). Conversely, the deletion of gltR1 from CJ522 (generating strain GB032) only marginally improved strain growth and muconate production compared to CJ522 (FIG. 13). We sought to determine whether both hexR and gltR1 deletions in a CJ522 background could generate an additive or synergistic effect. Interestingly, the deletion of both regulators (strain GB099) did not improve performance beyond GB062 (FIG. 13), suggesting that HexR maintains epistatic dominance over GltR1, potentially because the deletion of hexR leads to a de-repression of gltR.

Without the deletion of glucose dehydrogenase, another group deleted hexR with the intent to improve flux to erythrose-4-phosphate. The deletion of here in the gcd context generated a two-fold benefit: (1) allowing for the activation of genes for glucose metabolism which may be repressed in the absence of 2-ketogluconate and (2) the improved carbon flux from glucose through the EDEMP cycle to erythrose-4-phosphate, one of the critical nodes denoting the committed step to the Shikimate pathway.

WGS of the sorted evolved clones suggested that additional targets may further enhance growth and muconate production of engineered strains. In lineage B, a large deletion was observed which included the deletion of the 6-phosphogluconate dehydrogenase (gntZ, PP_4043) which may pull excess carbon into the PPP and away from biomass. Lineage A contained conserved mutations in gacS, a sensor kinase of a two-component system conserved across Pseudomonads. Prior studies have shown that spontaneous gacS mutations arise leading to higher growth rates suggesting that this mutation observed in our evolved clones may contribute to the improved growth performance. We therefore deleted gntZ and gacS individually and in combination from both strains CJ522 and GB062 and characterized the resulting mutants for production in shake flasks (FIG. 13).

Transcriptomics Analysis of Engineered Strains

Figures 14A, 14B, 14C:
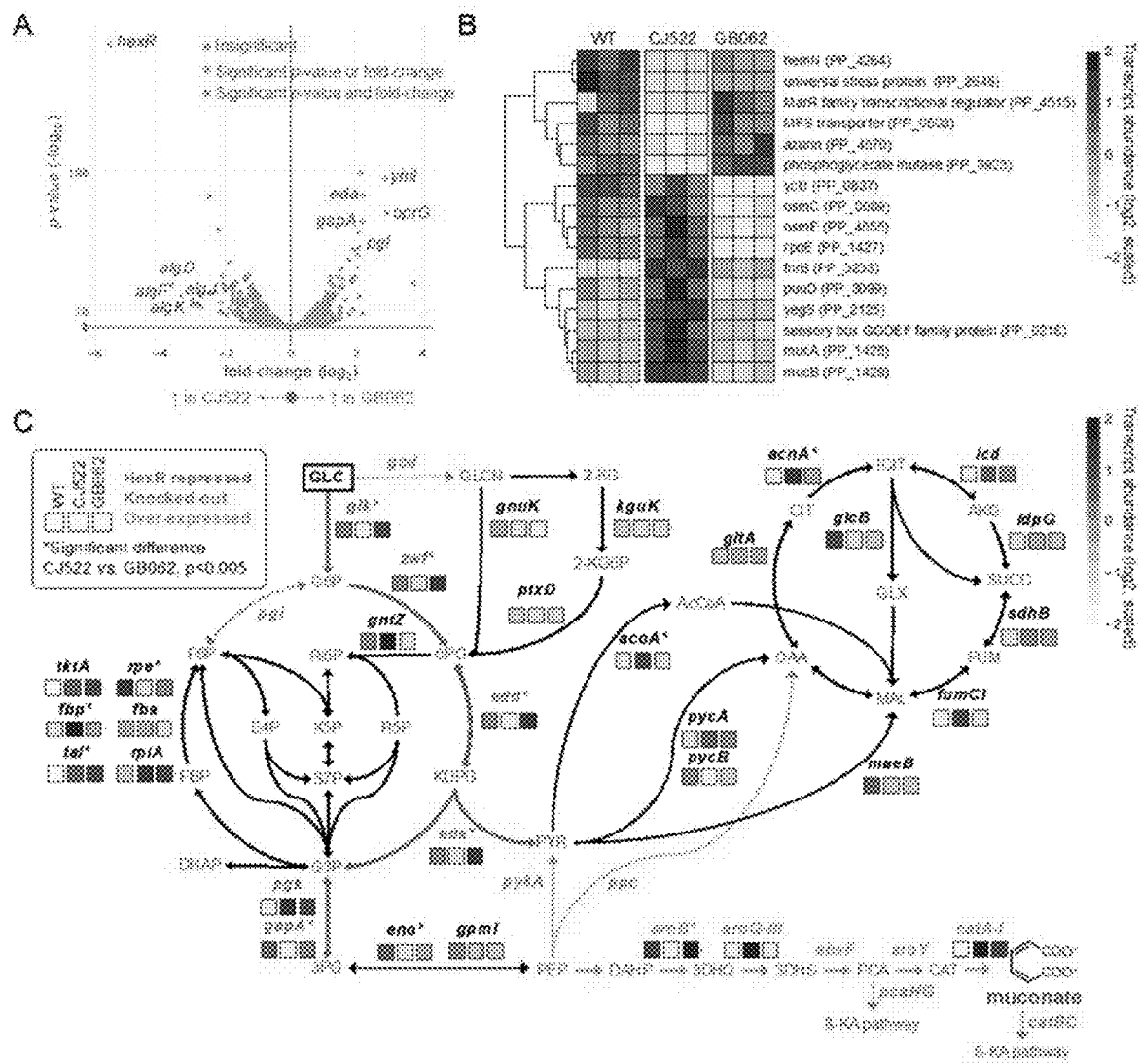
FIGS. 14A, 14B, and 14C depict that hexR deletion in GB062 relieves transcriptional repression of central carbon pathways. (A) Volcano plot of pairwise comparison between GB062 and CJ522 on glucose (p<0.005, fold-change>|1|). (B) Select hits from (A) plotted as a clustered heat-map with individual values from biological triplicate. (C) Metabolic pathway toward muconate production with heat-mapped transcript abundance overlaid for each gene. The average of biological triplicates is presented. Abbreviations are as follows: P: phosphate; GLC: glucose; GLCN: gluconate; 2-KG: 2-ketogluconate; 2-KG6P: 2-ketogluconate-6-P; G6P: glucose-6-P; 6PG: 6-phosphogluconate; KDPG: 2-keto-3-deoxy-6-phosphogluconate; G3P: glyceraldehyde-3-P; FBP: fructose-1,6-P2; F6P: fructose-6-P; XSP: xylose-5-P; S7P: sedoheptulose-7-P; E4P: erythrose-4-P; R5P: ribose-5-P; Ri5P: ribulose-5-P; 3PG: glycerate-3-P; PEP: phosphoenolpyruvate; DHAP: dihydroxyacetone-P; ICIT: isocitrate; CIT: citrate; AKG: alpha-ketoglutarate; SUCC: succinate; FUM: fumarate; MAL: malate; GLX; OAA: oxaloacetate; AcCoA: acetyl-Coenzyme A; PYR: pyruvate.
Figures 15A, 15B, 15C, 15D, 15E, 15F, 15G:
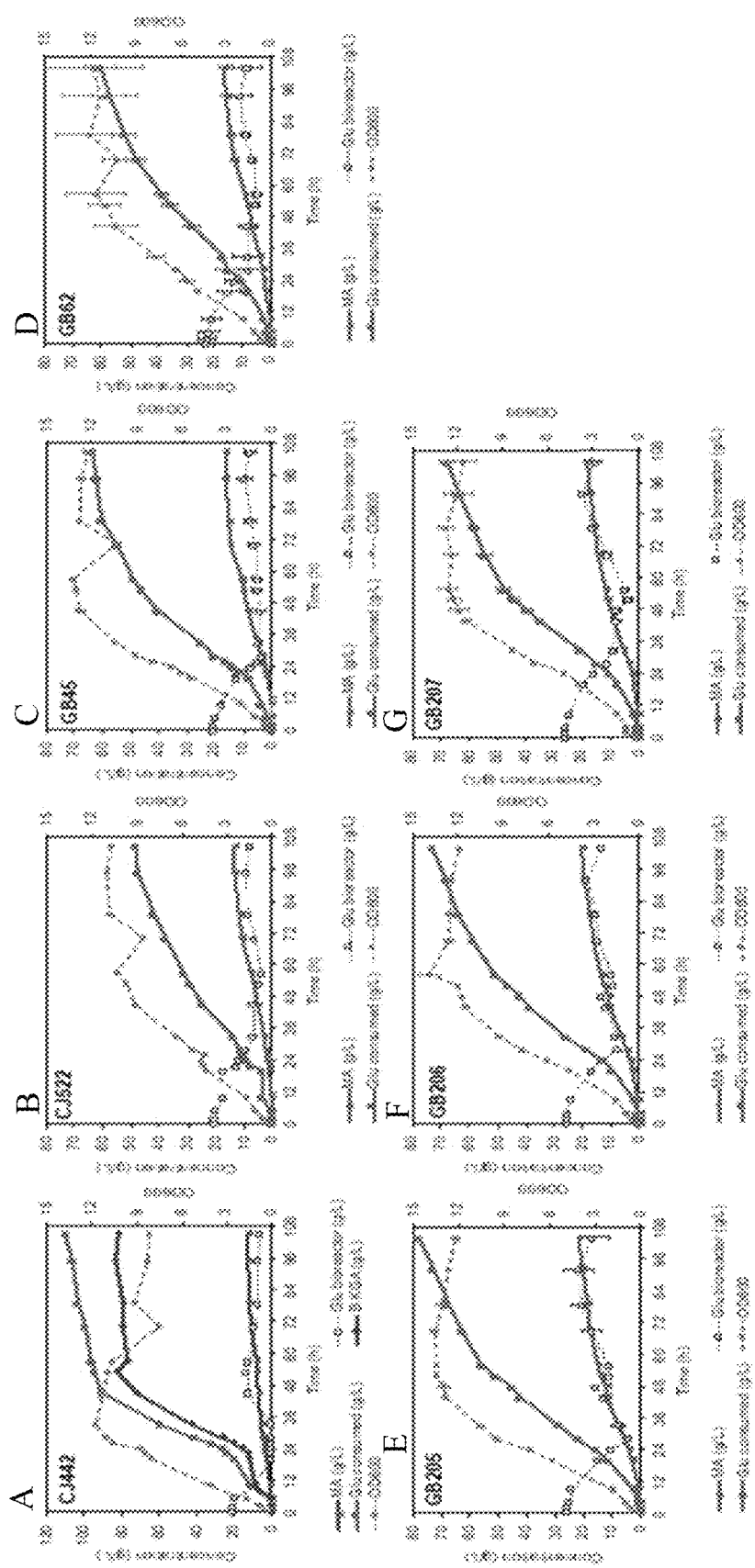
FIGS. 15A through 15G depict the results of shake flask experiments for strains CJ442, CJ522, GB45, GB62, GB205, GB206, and GB207, respectively, that show the levels of MA, Glu consumed, Glu in the bioreactor, B-KGA as well as cell density by OD600 for each engineered strain.

Since the singular deletion of hexR generated substantial performance improvements, we sought to investigate the effect of the hexR deletion. Transcriptomics were performed to assay the effect of the hexR deletion. The majority of variation in the expression of the 5,555 detected transcripts was driven by genotype, with wild-type separating strongly from both engineered strains by principal component analysis. A pairwise comparison of CJ522 and GB062 on glucose identified 1,074 differentially regulated genes with 993 up-regulated in GB062 and 81 up-regulated in CJ522 ($p<0.005$, fold-change $>|1|$). Hierarchical cluster analysis of hits identified several interesting expression clusters, with many hits related to various stress responses (FIG. 14). Several genes related to alginate production (mucA, mucB, alg suite) were down-regulated in GB062. Alginate is an anionic polysaccharide composed of ß-(1,4)-linked mannuronic and guluronic acids, and Pseudomad alginate biosynthesis has been studied in response to environmental stressors. Control of zwf expression is linked to alginate production in *P. aeruginosa*, but association with HexR activity in *P. putida* is unclear.

The HexR deletion in GB062 restored expression of glk, zwf, edd, eda, and gapA (FIG. 9C). Rpe, tal, eno, and aroB were also significantly up-regulated in GB062 whereas acoA and acnA were significantly down-regulated (FIG. 14). Together, transcriptomic data suggests that deletion of HexR in a muconate production background restores gene expression of HexR-repressed genes in the PPP and ED pathway genes, and may also contribute to disregulation of stress responses such as alginate production.

Bioreactor Cultivations Assess Strain Performance

Bioreactor cultivations were performed to characterize the performance of the improved strain GB062 compared to the parent strain CJ522, as well as the evolved clone GB045. In a bioreactor, GB062 outperformed both the parent strain CJ522 and the evolved clone GB045 in muconate productivity, titer, and yield. Strain GB062 produced 21.77 g/L muconate at a maximum productivity of 0.195 g/L/h compared to 15.4 g/L produced by CJ522 at a maximum productivity of 0.149 g/L/h. The yield of muconate produced by GB062 was also higher than that of the parent strain, at a yield of 45% (mol muconate/mol glucose) compared to the yield of 40.5% achieved by CJ522.

From one glucose molecule, CJ522-derived strains are engineered to allow the flux of one pyruvate to growth, and one pyruvate to PEP for muconate production, generating a maximum theoretical yield of 50%. Further, an erythrose-4-phosphate is condensed with the PEP to enter the shikimate pathway toward muconate. Therefore, a yield of 45% approaches the theoretical maximum.

As disclosed herein, various approaches were demonstrated to overcome a growth defect introduced by deleting the glucose dehydrogenase in *P. putida* KT2440 engineered for muconate production from glucose. Without this deletion, 2-ketogluconate accumulated substantially. We approached three methods to improve strain performance: evolution, biosensor-enabled selection, and rational engineering. Interestingly, all three avenues converged on a set of mutations which can improve the growth and muconate production of the resulting strains. Deletion of hexR conferred strain performance improvements. Mutations in the edd promoter observed in evolved population directed us to delete this regulator. The transcriptomics performed on the parent muconate-producing strain CJ522 compared to GB062 provide a comprehensive snapshot of the wide-ranging effects that this single gene deletion can introduce.

In the evolved populations, mutations in gacS appeared in several clones, suggesting that the order of these mutations in the evolved population was likely first the disruption of gacS, followed by the deletion in fleQ. We know this was probably the case due to the fact that only three of the four strains sequenced had deletions of fleQ but all four contained gacS disruptions. Interestingly, GacS may downregulate flagellar expression, so those mutations may be linked. Deletion of fleQ was performed with no growth enhancement observed. GacS has a wide range of regulatory targets.

TABLE 4

Strain construction details

| Strain | Genotype | Strain Construction Details |
|---|---|---|
| CJ200 | P. putida KT2440 ΔcatRBCA::Ptac:catA ΔpcaHG::Ptac:aroY:ecdB:asbF | Previously described. See: Johnson, C. W. et al. Enhancing muconic acid production from glucose and lignin-derived aromatic compounds via increased protocatechuate decarboxylase activity. Metabolic Engineering Communications 3, 111-119 (2016). |
| CJ385 | P. putida KT2440 ΔcatRBCA::Ptac:catA ΔpcaHG::Ptac:aroY:ecdB:asbF ΔpykA ΔpykF Δppc Δpgi-1 Δpgi-2 | pykA, pykF, ppc, pgi-1, and pgi-2 were deleted sequentially from CJ200. pykA was deleted with pCJ074 and this deletion was confirmed by diagnostic colony PCR amplification of a 1574 bp product, rather than the 3041 WT product, with primer pair oCJ408/oCJ409. pykF was deleted with pCJ075 and this deletion was confirmed by diagnostic colony PCR amplification of a 1625 bp product, rather than the 3037 WT product, with primer pair oCJ414/oCJ415. ppc was deleted with pCJ076 and this deletion was confirmed by diagnostic colony PCR amplification of a 1567 bp product, rather than the 4208 WT product, with primer pair oCJ420/oCJ421. pgi-1 was deleted with pCJ097 and this deletion was confirmed by diagnostic colony PCR amplification of a 2053 bp product, rather than the 3733 WT product, with primer pair oCJ504/oCJ505. pgi-2 was deleted with pCJ098 and this deletion was confirmedby diagnostic colony PCR amplification of a 2101 bp band, rather than a 3782 WT band, with primer pair oCJ511/oCJ512. |
| CJ442 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 | The Ptac:aroG-D146N:aroY:ecdB:asbF cassette was integrated into the pykA locus in CJ385 with pCJ117. Plasmid integration at the pykA locus was diagnosed by colony PCR amplification of a 845 bp product (5' junction) with primers oCJ408/oCJ055 and a 1,731 bp product (3' junction) with primers oCJ552/oCJ409, since this strain already contained a aroY:ecdB:asbF cassette that the plasmid could have recombined into instead. After confirming integration of the plasmid at the pykA locus and sucrose counter-selection, replacement of pykA with the Ptac:aroG-D146N:aroY:ecdB:asbFcassette was confirmed by diagnostic colony PCR amplification of a 5684 bp product, rather than the 1574 bp ΔpykA product, using primers oCJ408/oCJ409. |
| CJ522 | P. putida KT2440 ΔcatRBCA::Ptac:catA ΔpcaHG::Ptac:aroY:ecdB:asbF ΔpykA::aroG-D146N:aroY:ecdB:asbF ΔpykF Δppc Δpgi-1 Δpgi-2 Δgcd | gcd was deleted from CJ442 with pJE365. This strain was confirmed ot contain this deletion by diagnostic colony PCR amiplification of a 1502 bp product, rather than the 3887 bp WT product, with primer pair oCJ634/oCJ635. |
| CJ598 | P. putida KT2440 ΔpykA::Ptac:aroG-D146N:asbF ΔpykF Δppc Δpgi-1 Δpgi-2 ΔpcaHG::Ptac:ligABC Δgcd | pykA, pykF, ppc, pgi-1, and pgi-2 were deleted sequentially from CJ251 as described for CJ385. The Ptac:aroG-D146N:asbF cassette was then integrated into the pykA locus using plasmid pSN2 and this gene replacement was confirmed by diagnostic colony PCR amplification of a 3582 bp product, rather than the 1574 bp ΔpykA product, using primers oCJ408/oCJ409. gcd was deleted as described for CJ522. |
| CJ599 | P. putida KT2440 ΔpykA::Ptac:aroG-D146N:asbF ΔpykF Δppc Δpgi-1 Δpgi-2 ΔpcaHG::Ptac:praA Δgcd | pykA, pykF, ppc, pgi-1, and pgi-2 were deleted sequentially from CJ265 as described for CJ385. The Ptac:aroG-D146N:asbF cassette was then integrated into the pykA locus using plasmid pSN2 and this gene replacement was confirmed by diagnostic colony PCR amplification of a 3582 bp product, rather than the 1574 bp ΔpykA product, using primers oCJ408/oCJ409. gcd was deleted as described for CJ522. |

TABLE 5

Plasmid construction details

| Plasmid | Utility | Plasmid Construction Details |
|---|---|---|
| pCJ074 | Deletion of pykA in *P. putida* KT2440 and strains derived from it | The 5' targeting region was amplified from *P. putida* KT2440 genomic DNA with primer pair oCJ404/oCJ405 (804 bp) while the 3 targeting region was amplified with primer pair oCJ406/oCJ407 (806 bp) and these fragments were assembled into pK18mobsacB amplified with primer pair oCJ345/oCJ289 and digested with EcoRI and BamHI (5391 bp). |
| pCJ075 | Deletion of pykF in *P. putida* KT2440 and strains derived from it | The 5' targeting region was amplified from *P. putida* KT2440 genomic DNA with primer pair oCJ410/oCJ411 (798 bp) while the 3 targeting region was amplified with primer pair oCJ412/oCJ413 (812 bp) and these fragments were assembled into pK18mobsacB amplified with primer pair oCJ345/oCJ289 and digested with EcoRI and BamHI (5391 bp). |
| pCJ076 | Deletion of ppc in *P. putida* KT2440 and strains derived from it | The 5' targeting region was amplified from *P. putida* KT2440 genomic DNA with primer pair oCJ416/oCJ417 (809 bp) while the 3 targeting region was amplified with primer pair oCJ418/oCJ419 (814 bp) and these fragments were assembled into pK18mobsacB amplified with primer pair oCJ345/oCJ289 and digested with EcoRI and BamHI (5391 bp). |
| pCJ097 | Deletion of pgi-1 in *P. putida* KT2440 and strains derived from it | The 5' targeting region was amplified from *P. putida* KT2440 genomic DNA with primer pair oCJ499/oCJ500 (1050 bp) while the 3 targeting region was amplified with primer pair oCJ501/oCJ502 (1060 bp) and these fragments were assembled into pK18mobsacB amplified with primer pair oCJ345/oCJ289 and digested with EcoRI and BamHI (5391 bp). |
| pCJ098 | Deletion of pgi-2 in *P. putida* KT2440 and strains derived from it | The 5' targeting region was amplified from *P. putida* KT2440 genomic DNA with primer pair oCJ506/oCJ507 (1054 bp) while the 3 targeting region was amplified with primer pair oCJ508/oCJ509 (1056 bp) and these fragments were assembled into pK18mobsacB amplified with primer pair oCJ345/oCJ289 and digested with EcoRI and BamHI (5391 bp). |
| pCJ117 | Replacement of pykA with aroG-D146N:aroY:ecdB:asbF in *P. putida* KT2440 and strains derived from it | The *E. coli* aroG-D146N gene was codon optimzed and synthesized as a linear DNA, CJ_aroG-D146N_opt_Pp (1053 bp), by IDT. The aroY:ecdB:asbF casette was amplified from pCJ045 with primers oCJ553/oCJ606 (3046 bp). These fragments were then assembled and amplified as a single fragment with primer pair oCJ605/oCJ606 (4178 bp), which incorporated the tac promoter to drive expression of these genes. This fragment was then assembled into pCJ074 digested with NotI (6905). |
| pCJ125 | Deletion of galC and integration of the tac promoter upstream of galBD n *P. putida* KT2440 and strains derived from it | galB was amplified from *P. putida* KT2440 genomic DNA with primer pair oCJ626/oCJ627 (855 bp) and assembled into pCJ124 digested with SpeI (7,572 bp). |
| pJE365 | Deletion of gcd in *P. putida* KT2440 and strains derived from it | The 5' targeting region was amplified from *P. putida* KT2440 genomic DNA with primer pair pJE365_5'_F/pJE365_5'_R (751 bp) while the 3' targeting region was amplified from *P. putida* KT2440 genomic DNA with primer pair pJE365_3'_F/pJE365_3'_R (748 bp) and these fragments were assembled into pK18mobsacB linearized with by digestion with restriction enzymes XbaI and HindIII (5695 bp). |
| pSN2 | Replacement of pykA with the Ptac:aroG-D146N:asbF cassette in *P. putida* KT2440 and strains derived from it | pCJ117 was amplified linearly with oSN3 and oSN4 (8905 bp) to include aroG-D146N and AsbF but exclude aroY:ecdB and treated with NEB KLD Enzyme Mix (New England Biolabs), which includes kinase, ligase and DpnI enzymes to phosphorylate and circularize the PCR product and digest the template, according to the manufacturer's instructions. |

TABLE 6

Primer sequences and description

| Primer | Sequence (5'→3') | Description |
|---|---|---|
| oCJ289 SEQ ID NO: 1 | CTAACTCACATTAATTGCGTTGCGCTCACTG | pK18mobsacB around the world R |
| oCJ345 SEQ ID NO: 2 | GAATTCctgcagtctagaGGATCCctagcttcacgctgccgcaag | pK18mobsacB around the world F with EcoRI, XbaI, PstI, and BamHI sites |
| oCJ404 SEQ ID NO: 3 | gtgagcgcaacgcaattaatgtgagttagGAATTCaccggtaaagcggttgaacacctg | pykA upstream targeting F with pK18mobsacB overlap |

TABLE 6-continued

Primer sequences and description

| Primer | Sequence (5'→3') | Description |
|---|---|---|
| oCJ405 SEQ ID NO: 4 | aacgagtggaGCGGCCGCatagtgaagcgcagcgaaaggctac | pykA upstream targeting R with downstream targeting overlap |
| oCJ406 SEQ ID NO: 5 | gcgcttcactatGCGGCCGCtccactcgtttcacagcacaaggc | pykA downstream targeting F with upstream targeting overlap |
| oCJ407 SEQ ID NO: 6 | ccctgagtgcttgcggcagcgtgaagctagGGATCCcaccgagatcgaagcacgcg | pykA downstream targeting R with pK18mobsacB targeting overlap |
| oCJ408 SEQ ID NO: 7 | CAACCCATTTTCAGAGGC | Diagnostic: outside pykA upstream targeting region F |
| oCJ409 SEQ ID NO: 8 | AACACCACCATCATCGAC | Diagnostic: outside pykA downstream targeting region R |
| oCJ410 SEQ ID NO: 9 | agtgagcgcaacgcaattaatgtgagttagGAATTCgccacggtctacacctatgcc | pykF upstream targeting F with pK18mobsacB overlap |
| oCJ411 SEQ ID NO: 10 | aatcGCGGCCGCtcatgattgggcagtctcaaggatcagg | pykF upstream targeting R with downstream targeting overlap |
| oCJ412 SEQ ID NO: 11 | gagactgcccaatcatgaGCGGCCGCgattgccggggcgc | pykF downstream targeting F with upstream targeting overlap |
| oCJ413 SEQ ID NO: 12 | ccctgagtgcttgcggcagcgtgaagctagGGATCCcatgccgacgatgatcagcaacc | pykF downstream targeting R with pK18mobsacB targeting overlap |
| oCJ414 SEQ ID NO: 13 | ACAAGGCGCTGCTGAAATC | Diagnostic: outside pykF downstream targeting region F |
| oCJ415 SEQ ID NO: 14 | CGCATAGGGATTGACGAT | Diagnostic: outside pykF downstream targeting region R |
| oCJ416 SEQ ID NO: 15 | agtgagcgcaacgcaattaatgtgagttagGAATTCtcgctcaatccctgacataaccgc | ppc upstream targeting F with pK18mobsacB overlap |
| oCJ417 SEQ ID NO: 16 | gcttgcccGCGGCCGCgttgcatccctatcagcctcagc | ppc upstream targeting R with downstream targeting overlap |
| oCJ418 SEQ ID NO: 17 | gatagggatgcaacGCGGCCGCgggcaagcccgggtcatg | ppc downstream targeting F with upstream targeting overlap |
| oCJ419 SEQ ID NO: 18 | tgagtgcttgcggcagcgtgaagctagGGATCCgaacggtttcttccttgtcgtcgtcac | ppc downstream targeting R with pK18mobsacB targeting overlap |
| oCJ420 SEQ ID NO: 19 | CTCCTGATAACGACGATG | Diagnostic: outside ppc downstream targeting region F |
| oCJ421 SEQ ID NO: 20 | CTTGGTCTGGCTGTGGTA | Diagnostic: outside ppc downstream targeting region R |
| oCJ499 SEQ ID NO: 21 | gtgagcgcaacgcaattaatgtgagttagGAATTCtcacacttggcctgatcagggtttg | pgi-1 upstream targeting F with pK18mobsacB overlap |
| oCJ500 SEQ ID NO: 22 | gcagggGCGGCCGCgatacgggtaaagccagaacctatcaatcg | pgi-1 upstream targeting R with NotI and downstream targeting overlap |

TABLE 6-continued

Primer sequences and description

| Primer | Sequence (5'→3') | Description |
|---|---|---|
| oCJ501 SEQ ID NO: 23 | tggctttacccgtatcGCGGCCGCccctgcttgatactggcccg | pgi-1 downstream targeting F with NotI and upstream targeting overlap |
| oCJ502 SEQ ID NO: 24 | ccctgagtgcttgcggcagcgtgaagctagGGATCCtctgtggtaagggagcgctcc | pgi-1 downstream targeting R with pK18mobsacB targeting overlap |
| oCJ504 SEQ ID NO: 25 | GCTTGTCCAATGGCAGTG | Colony PCR: outside pgi-1 upstream targeting region F |
| oCJ505 SEQ ID NO: 26 | CGCAGCCAGCAAGATATAG | Colony PCR: outside pgi-1 downstream targeting region R |
| oCJ506 SEQ ID NO: 27 | agtgagcgcaacgcaattaatgtgagttagGAATTCggtgagggcaaacgcatcgg | pgi-2 upstream targeting F with pK18mobsacB overlap |
| oCJ507 SEQ ID NO: 28 | caagctcggaGCGGCCGCggtgcgtggtgagggcttg | pgi-2 upstream targeting R with NotI and downstream targeting overlap |
| oCJ508 SEQ ID NO: 29 | tcaccacgcaccGCGGCCGCtccgagcttgtgccggc | pgi-2 downstream targeting F with NotI and upstream targeting overlap |
| oCJ509 SEQ ID NO: 30 | ccctgagtgcttgcggcagcgtgaagctagGGATCCcggtggtatgcagcacccc | pgi-2 downstream targeting R with pK18mobsacB targeting overlap |
| oCJ511 SEQ ID NO: 31 | ACACGGGTTCAGTGCATG | Diagnostic: outside pgi-2 upstream targeting region F |
| oCJ512 SEQ ID NO: 32 | GAAGGTCATCGTTGCCTG | Diagnostic: outside pgi-2 downstream targeting region R |
| oCJ553 SEQ ID NO: 33 | gctaatgcggtcaaggcgcgtcggggctgaAGAGGAGGGAGAatgcagaaccc | aroY F with aroG-D146N overlap |
| oCJ605 SEQ ID NO: 34 | caggagtagcctttcgctgcgcttcactatgagctgttgacaattaatcatcggctcgtataatgtgtggaattgtgagcggataacaatttcacacAGGAGGACTTACatgaactatcagaatgatgacttgcgcatcaagg | aroG-D146N opt P.p. F with synthetic RBS, Ptac, and upstream ΔpykA overlap |
| oCJ606 SEQ ID NO: 35 | gcttgagccttgtgctgtgaaacgagtggaGTTTAAACtcaggaggttacgacctccagc | asbF opt P.p. R with PmeI and downstream ΔpykA overlap |
| oCJ634 SEQ ID NO: 36 | TGCGCTACAACCTTACCC | Diagnostic: outside gcd upstream targeting region F |
| oCJ635 SEQ ID NO: 37 | TAGGCTTTGACCTCGTCG | Diagnostic: outside gcd upstream targeting region R |
| pJE365_5'_F SEQ ID NO: 38 | agctcggtacccggggatcctctagaGAACCCTTCCAACCTCGAAT | gcd upstream targeting F with pK18mobsacB overlap |
| pJE365_5'_R SEQ ID NO: 39 | ATCTTGGTGCCCAGCGAatCGTAGGTTCTCCGTCAG | gcd upstream targeting R with NotI and downstream targeting overlap |
| pJE365_3'_F SEQ ID NO: 40 | CTGACGGAGAACCTACGatTCGCTGGGCACCAAGAT | gcd downstream targeting F with NotI and upstream targeting overlap |

TABLE 6-continued

Primer sequences and description

| Primer | Sequence (5'→3') | Description |
|---|---|---|
| pJE365_3'_R SEQ ID NO: 41 | gtaaaacgacggccagtgccaagcttGGGTATTCGACTTCGACCAG | gcd downstream targeting R with pK18mobsacB targeting overlap |
| oSN3 SEQ ID NO: 42 | GCCCAAAatgaagtacagcctgtgcaccatcag | asbF with synthetic RBS for KLD rxn F |
| oSN4 SEQ ID NO: 43 | TCCTCTacgtgggtggcgtcagccccgacgcgc | aroG-D146N with synthetic RBS for KLD rxn R |

TABLE 7

Fragment CJ_aroG-D146N_opt_Pp sequence and description

| Fragment | Sequence (5'-3') | Description |
|---|---|---|
| CJ_aroG-D146N_opt_Pp SEQ ID NO: 44 | atgaactatcagaatgatgacttgcgcatcaaggaaatcaaggagctgctgccgccggtggccctgttggaaaagttccggctaccgagaacgctgccaataccgtcgcccacgcacgcaaggccatccataaaatcctgaagggcaacgatgatcgcctgctggtggtgatcggtccttgtagcatccacgacccggtggcggccaaagagtacgccacccggttgctggcattgcgcgaggaactgaaggacgagctggaaatcgtcatgcgggtgtacttcgagaagccacggaccaccgtcggctggaagggcctgatcaacgacccgcacatggacaactcgttccagatcaacgacggcctgcgtatcgcccgcaagttgttgctggacatcaacgacagcggcctgccggcagccggcgagttcttgaacatgatcacgccgcagtacctggcggatctgatgtcgtggggcgccatcggcgcacgcaccaccgagagccaggtgcatcgtgaactggcctcggggctgtcctgccccgtgggctttaagaacggcaccgacgggaccattaaagtcgcaatcgatgcgatcaatgcggcgggcgccccgcactgcttcctgtccgtgaccaagtggggccacagcgccatcgtaaacacctcgggtaacggggactgccacatcatcctgcgtggtggcaaagagccgaactacagcgccaagcacgtggcggaggtgaaggaaggcctgaacaaagccggcctgccggcgcaggtgatgatcgatttcagccatgccaactccagcaagcaattcaaaaagcagatggatgtgtgcgccgacgtgtgccagcagatcgccggtgcgaaaaagccatcatcggggtaatggtggaatcgcatctggtggagggcaatcaatccctggaatcgggcgaaccccctggcctacggcaaaagcatcaccgatgcctgcatcggctgggaggacaccgacgccctgctgcgccaactcgctaatgcggtcaaggcgcgtcgggctga | The aroG gene from E. coli K-12 MG1655 incorporating the D146N mutation was optimized for expression in P. putida KT2440. |

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration

What is claimed is:

1. A non-naturally occurring *Pseudomonas* sp. comprising an endogenous genetic deletion that eliminates the expression of a pyruvate kinase encoded by pykF as well as genetic deletions of gcd and hexR genes, wherein the microorganism is capable of producing 3-deoxy-D-arabino-heptulosonate-7-phosphate and muconic acid;
  and wherein the muconic acid production is greater than that in the naturally occurring *Pseudomonas* sp.

2. The microorganism of claim 1, wherein the microorganism is selected from the group consisting of *P. putida*, *P. fluorescens*, and *P. stutzeri*.

3. The microorganism of claim 2, wherein the microorganism is *P. putida* KT2440.

4. The microorganism of claim 1, wherein the microorganism catabolizes at least one of a lignin depolymerization product, a cellulose depolymerization product, and a hemicellulose depolymerization product.

5. The microorganism of claim 4, wherein the lignin depolymerization product comprises an aromatic compound.

6. The microorganism of claim 4, wherein the cellulose depolymerization product comprises glucose.

* * * * *